US009056850B2

(12) United States Patent
Filliers et al.

(10) Patent No.: US 9,056,850 B2
(45) Date of Patent: Jun. 16, 2015

(54) PROCESS FOR THE PREPARATION OF COMPOUNDS USEFUL AS INHIBITORS OF SGLT

(75) Inventors: Walter Ferdinand Maria Filliers, Vremde (BE); Rudy Laurent Maria Broeckx, Turnhout (BE); Patrick Hubert J. Nieste, Westerlo (BE); Masanori Hatsuda, Osaka (JP); Masahiko Yoshinaga, Osaka (JP); Mitsuhiro Yada, Osaka (JP); Christopher Teleha, Fort Washington, PA (US)

(73) Assignees: Janssen Pharmaceutica N.V., Beerse (BE); Mitsubishi Tanabe Pharma Corporation, Osaka (JP)

(*) Notice: Subject to any disclaimer, the term of this patent is extended or adjusted under 35 U.S.C. 154(b) by 952 days.

(21) Appl. No.: 12/578,934

(22) Filed: Oct. 14, 2009

(65) Prior Publication Data
US 2010/0099883 A1    Apr. 22, 2010

Related U.S. Application Data

(60) Provisional application No. 61/106,231, filed on Oct. 17, 2008, provisional application No. 61/106,260, filed on Oct. 17, 2008.

(51) Int. Cl.
*C07D 409/04* (2006.01)
*C07D 333/12* (2006.01)
*C07D 409/10* (2006.01)

(52) U.S. Cl.
CPC .......... *C07D 333/12* (2013.01); *C07D 409/10* (2013.01)

(58) Field of Classification Search
CPC ..................... C07D 333/12; C07D 409/10
USPC .......................................................... 549/60
See application file for complete search history.

(56) References Cited

U.S. PATENT DOCUMENTS

| | | | |
|---|---|---|---|
| 2,799,241 A | 7/1949 | Wurster | |
| 4,160,861 A | 7/1979 | Cole et al. | |
| 4,584,369 A | 4/1986 | Klein et al. | |
| 5,149,838 A | 9/1992 | Humphrey et al. | |
| 5,292,461 A | 3/1994 | Juch et al. | |
| 5,401,435 A | 3/1995 | Burzio et al. | |
| 5,424,406 A | 6/1995 | Tsujihara et al. | |
| 5,610,294 A | 3/1997 | Lam et al. | |
| 5,731,292 A | 3/1998 | Tsujihara et al. | |
| 5,767,094 A | 6/1998 | Tsujihara et al. | |
| 5,780,483 A | 7/1998 | Widdowson et al. | |
| 5,830,873 A | 11/1998 | Tsujihara et al. | |
| 5,861,385 A | 1/1999 | Angerbauer et al. | |
| 5,945,533 A | 8/1999 | Kometani et al. | |
| 6,048,842 A | 4/2000 | Tsujihara et al. | |
| 6,069,238 A | 5/2000 | Hitchcock et al. | |
| 6,153,632 A | 11/2000 | Rieveley | |
| 6,277,833 B1 | 8/2001 | Angerbauer et al. | |
| 6,297,363 B1 | 10/2001 | Kubo et al. | |
| 6,414,126 B1 | 7/2002 | Ellsworth et al. | |
| 6,420,513 B2 | 7/2002 | Minami | |
| 6,448,415 B1 | 9/2002 | Lee et al. | |
| 6,475,521 B1 | 11/2002 | Timmins et al. | |
| 6,479,661 B1 | 11/2002 | Buchholz et al. | |
| 6,515,117 B2 | 2/2003 | Ellsworth et al. | |
| 6,562,791 B1 | 5/2003 | Maurya et al. | |
| 6,617,313 B1 | 9/2003 | Maurya et al. | |
| 6,627,611 B2 | 9/2003 | Tomiyama et al. | |
| 6,800,761 B1 | 10/2004 | Franc et al. | |
| 7,008,959 B2 | 3/2006 | Franc et al. | |
| 7,045,665 B2 | 5/2006 | Fujikura et al. | |
| 7,074,826 B2 | 7/2006 | Wechter et al. | |
| 7,084,123 B2 | 8/2006 | Fujikura et al. | |
| 7,202,350 B2 | 4/2007 | Imamura et al. | |
| 7,271,153 B2 | 9/2007 | Nishimura et al. | |
| 7,288,528 B2 | 10/2007 | Frick et al. | |
| 7,294,618 B2 | 11/2007 | Fushimi et al. | |
| 7,375,213 B2 | 5/2008 | Deshpande et al. | |
| 7,417,032 B2 | 8/2008 | Eckhardt et al. | |
| 7,511,022 B2 | 3/2009 | Beavers et al. | |
| 7,566,699 B2 | 7/2009 | Fushimi et al. | |
| 7,576,064 B2 | 8/2009 | Kikuchi et al. | |
| 7,666,845 B2 | 2/2010 | Cook et al. | |
| 7,932,379 B2 | 4/2011 | Deshpande et al. | |
| 7,943,582 B2 | 5/2011 | Nomura et al. | |
| 7,943,788 B2 | 5/2011 | Nomura et al. | |
| 2001/0041674 A1 | 11/2001 | Tomiyama et al. | |
| 2002/0032164 A1 | 3/2002 | Dale et al. | |
| 2002/0052326 A1 | 5/2002 | Washburn | |

(Continued)

FOREIGN PATENT DOCUMENTS

| | | |
|---|---|---|
| CA | 2494177 A1 | 2/2004 |
| EP | 0355750 A1 | 2/1990 |

(Continued)

OTHER PUBLICATIONS

Arakawa et al., "Improved diabetic syndrome in C57BL/Ks-db/db mice by oral administration of the Na+-glucose cotransporter inhibitor T-1095." Br. J. Pharmacol., 2001, vol. 132, pp. 578-586.

Kahn et al., "Normalization of blood glucose in diabetic rats with phlorizin treatment reverses insulin-resistant glucose transport in adipose cells without restoring glucose transporter gene expression.", J. Clin. Invest., 1991, vol. 87, pp. 561-570.

Klapars et al., "Copper-Catalyzed Halogen Exchange in Aryl Halides: An Aromatic Finkelstein Reaction.", J. Am. Chem. Soc., (2002), vol. 124(50), pp. 14844-14845.

Polshettiwar et al., "Pd-N-heterocycle carbene (NHR) organic silica: synthesis and application in carbon-carbon coupling reactions.", Tetrahedron, May 12, 2008, pp. 4637-4643, vol. 64(20), Elsevier Science Publishers, Amsterdam, NL, XP022607642.

Rossetti et al., "Correction of Hyperglycemia with Phlorizin Normalizes Tissue sensitivity to Insulin in Diabetic Rats.", J. Clin. Invest., 1987, vol. 79, pp. 1510-1515.

(Continued)

*Primary Examiner* — Taofiq A Solola

(57) ABSTRACT

The present invention is directed to a novel process for the preparation of compounds having inhibitory activity against sodium-dependent glucose transporter (SGLT) being present in the intestine or kidney.

31 Claims, No Drawings

(56) References Cited

U.S. PATENT DOCUMENTS

| | | |
|---|---|---|
| 2002/0111315 A1 | 8/2002 | Washburn et al. |
| 2003/0024914 A1 | 2/2003 | Aleshin |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0191121 A1 | 10/2003 | Miller et al. |
| 2004/0053855 A1 | 3/2004 | Fujikura et al. |
| 2004/0063646 A1 | 4/2004 | Fujikura et al. |
| 2004/0110936 A1 | 6/2004 | Ohsumi et al. |
| 2004/0116357 A1 | 6/2004 | Fushimi et al. |
| 2004/0132669 A1 | 7/2004 | Nishimura et al. |
| 2004/0138143 A1 | 7/2004 | Glombik et al. |
| 2004/0259819 A1 | 12/2004 | Frick et al. |
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124555 A1 | 6/2005 | Tomiyama et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2005/0256317 A1 | 11/2005 | Sato et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2008/0027122 A1 | 1/2008 | Nomura et al. |
| 2008/0119422 A1 | 5/2008 | Nomura et al. |
| 2008/0132563 A1 | 6/2008 | Kakinuma et al. |
| 2008/0146515 A1 | 6/2008 | Nomura et al. |
| 2008/0234366 A1 | 9/2008 | Bindra et al. |
| 2009/0124702 A1 | 5/2009 | Siva Satya Krishna Babu et al. |
| 2009/0233874 A1 | 9/2009 | Abdel-Magid et al. |
| 2011/0009347 A1 | 1/2011 | Liang et al. |
| 2011/0087017 A1 | 4/2011 | Farina et al. |
| 2011/0212905 A1 | 9/2011 | Nomura et al. |
| 2012/0058941 A1 | 3/2012 | Nomura et al. |
| 2012/0115799 A1 | 5/2012 | Wang et al. |

FOREIGN PATENT DOCUMENTS

| | | |
|---|---|---|
| EP | 0348184 B1 | 3/1993 |
| EP | 0579204 A2 | 1/1994 |
| EP | 0579204 A3 | 1/1994 |
| EP | 0625513 B1 | 9/1999 |
| EP | 1172362 A1 | 1/2002 |
| EP | 1338603 A1 | 8/2003 |
| EP | 1528066 A1 | 5/2005 |
| EP | 1845095 | 10/2007 |
| EP | 1956023 A1 | 3/2008 |
| GB | 2359554 A | 8/2001 |
| JP | 59039889 A | 3/1984 |
| JP | 63-233975 A | 9/1988 |
| JP | H03-503280 | 7/1991 |
| JP | 4-253974 A | 9/1992 |
| JP | 06256354 A | 9/1994 |
| JP | 07242526 A | 9/1995 |
| JP | 9-263549 A | 10/1997 |
| JP | 2000-34230 A | 2/2000 |
| JP | 2000-34239 A | 2/2000 |
| JP | 2001-288178 A | 10/2001 |
| JP | 2002167430 A | 6/2002 |
| JP | 2003-12686 A1 | 1/2003 |
| JP | 2003238417 A | 8/2003 |
| JP | 2003313168 A | 11/2003 |
| JP | 2007-230999 A | 9/2007 |
| WO | 89/05639 A | 6/1989 |
| WO | WO 93/09100 A1 | 5/1993 |
| WO | 93/21178 A1 | 10/1993 |
| WO | WO 94/14807 A1 | 7/1994 |
| WO | 96/13258 A1 | 5/1996 |
| WO | WO 97/17949 A1 | 5/1997 |
| WO | 97/25033 A1 | 7/1997 |
| WO | 98/42347 A1 | 10/1998 |
| WO | 99/65861 A1 | 12/1999 |
| WO | 99/67236 A | 12/1999 |
| WO | 00/28989 A1 | 5/2000 |
| WO | WO 00/27823 A1 | 5/2000 |
| WO | 00/74681 A1 | 12/2000 |
| WO | 01/27128 | 4/2001 |
| WO | 01/32157 A2 | 5/2001 |
| WO | 01/64669 A1 | 9/2001 |
| WO | 01/68660 A1 | 9/2001 |
| WO | 01/74834 A1 | 10/2001 |
| WO | 01/74835 A1 | 10/2001 |
| WO | WO 01/85167 A1 | 11/2001 |
| WO | WO 02/26706 A2 | 4/2002 |
| WO | 02/053573 A1 | 7/2002 |
| WO | 02/068439 A1 | 9/2002 |
| WO | 02/068440 A1 | 9/2002 |
| WO | 02/070020 A2 | 9/2002 |
| WO | 02/070020 A3 | 9/2002 |
| WO | 02/083066 A2 | 10/2002 |
| WO | 02/094262 A1 | 11/2002 |
| WO | WO 02/096357 A2 | 12/2002 |
| WO | 03/000712 A1 | 1/2003 |
| WO | 03/011880 A1 | 2/2003 |
| WO | 03/020737 A1 | 3/2003 |
| WO | 03/040121 A1 | 5/2003 |
| WO | 03/043621 A1 | 5/2003 |
| WO | 03/087104 A1 | 10/2003 |
| WO | 03/099836 A1 | 12/2003 |
| WO | 2004/007517 A1 | 1/2004 |
| WO | 2004/013118 A1 | 2/2004 |
| WO | 2004/014931 A1 | 2/2004 |
| WO | 2004/019958 A1 | 3/2004 |
| WO | 2004/052902 A1 | 6/2004 |
| WO | 2004/052903 A1 | 6/2004 |
| WO | 2004/063209 A2 | 7/2004 |
| WO | 2004/063209 A3 | 7/2004 |
| WO | 2004/064806 A | 8/2004 |
| WO | 2004/080990 A1 | 9/2004 |
| WO | WO 2004/076470 A2 | 9/2004 |
| WO | 2004/087727 A1 | 10/2004 |
| WO | 2004/099230 A1 | 11/2004 |
| WO | 2004/113359 A1 | 12/2004 |
| WO | WO 2005/009539 A2 | 2/2005 |
| WO | WO 2005/009954 A2 | 2/2005 |
| WO | WO 2005/012326 A1 | 2/2005 |
| WO | WO 2005/058845 A2 | 6/2005 |
| WO | 2006/010557 | 2/2006 |
| WO | 2006/080577 A1 | 8/2006 |
| WO | WO 2006/108842 A1 | 10/2006 |
| WO | 2007/025943 A2 | 3/2007 |
| WO | WO 2007/031548 A2 | 3/2007 |
| WO | WO 2007/087441 A2 | 8/2007 |
| WO | 2008/013322 A1 | 1/2008 |
| WO | 2008/020011 A1 | 2/2008 |
| WO | 2008/034859 A1 | 3/2008 |
| WO | WO 2008/034859 A1 | 3/2008 |
| WO | 2008/055870 A1 | 5/2008 |
| WO | 2008/055940 A2 | 5/2008 |
| WO | WO 2008/069327 A1 | 6/2008 |
| WO | WO 2008/070609 A1 | 6/2008 |
| WO | 2009/022010 A1 | 2/2009 |
| WO | 2009/023537 | 2/2009 |
| WO | 2009/026537 A1 | 2/2009 |

(56) References Cited

FOREIGN PATENT DOCUMENTS

| WO | WO 2009/035969 A1 | 3/2009 |
|---|---|---|
| WO | 2009/091082 A1 | 7/2009 |
| WO | 2009/121945 A2 | 10/2009 |

OTHER PUBLICATIONS

Rossetti et al., "Effect of Chronic Hyperglycemia on in Vivo Insulin Secretion in Partially Pancreatectomized Rats.", J. Clin Invest., 1987, vol. 80, pp. 1037-1044.

Rossetti et al., "Glucose Toxicity.", Diabetes Care, 1990, vol. 13(6), pp. 610-630.

Srogl et al., "Sulfonium salts. Participants par excellence in metal-catalyzed carbon-carbon bond-forming reactions.", Journal of the American Chemical Society, Jan. 1, 1997, pp. 12376-12377, vol. 119, American Chemical Society, US, XP002955770.

Tsujihara et al., "Na+-Glucose Cotransporter (SGLT) Inhibitors as Antidiabetic Agents. 4. Synthesis and Pharmacological Properties of 4'-Dehydroxyphlorizin Derivatives Substituted on the B Ring.", J. Med. Chem., 1999, vol. 42, pp. 5311-5324.

Ueta et al., "Long-term treatment with the Na+-glucose cotransporter inhibitor T-1095 causes sustained improvement in hyperglycemia and prevents diabetic neuropathy in Goto-kakizaki Rats.", Life Sciences, 2005, vol. 76, pp. 2655-2668.

Unger et al., "Hyperglycemia as an inducer as well as a consequence of impaired islet cell function and insulin resistance: implication for the management of diabetes.", Diabetologia, 1985, vol. 28, pp. 119-121.

Partial International Search Report relating to International Patent Application No. PCT/EP2009/063503, filed Oct. 15, 2009. Date of Mailing of Partial International Search Report: Dec. 3, 2010.

International Search Report relating to International Patent Application No. PCT/EP2009/063503, filed Oct. 15, 2009. Date of Mailing of International Search Report: Jun. 21, 2011.

Greene et al., "Protective Groups in Organic Synthesis.", 3rd Edition, 1999, pp. 119-121, XP002670712.

Hongu et al., "Na+-Glucose Cotransporter Inhibitors as Antidiabetic Agents. II. Synthesis and Structure-Activity Relationships of 4'-Dehydroxyphlorizin Derivatives.", Chem. Pharm. Bull., 1998, pp. 22-33, vol. 46(1).

Maatooq et al., "C-p-Hydroxybenzoylglycoflavones From *Citrullus colocynthis*.", Phytochemistry, Jan. 1997, pp. 187-190, vol. 44(1).

Unger et al., "Hyperglycemia as an inducer as well as a consequence of impaired islet cell function and insulin resistance: implications for the management of diabetes.", *Diabetologia*, 1985, pp. 119-121, vol. 28.

Zamani et al., "Synthesis and Structure Determination of Some New N-Glycosides of 4,5-Disubstituted-1,2,4-triazole-3-thiones.", *Journal of the Chinese Chemical Society*, 2002, pp. 1041-1044, vol. 49.

Greene et al., "Protective Groups in Organic Synthesis.", 3rd Edition, 1999, pp. 170.

Apsel et al., "General Entries to C-aryl glycosides. Formal synthesis of galtamycinone.", Tetrahedron Letters, 2003, pp. 1075-1077, vol. 44.

Kaelin et al., "General Strategies for the Synthesis of the Major Classes of C-aryl Glycosides.", J. Am. Chem. Soc., 2001, pp. 6937-6938, vol. 123.

Lee et al., "Recent Advances in Aryl C-Glycoside Synthesis.", Current Topics in Medicinal Chemistry, 2005, pp. 1333-1350, vol. 5.

Martin, S. F., "Unified Strategy for the Synthesis of C-aryl glycosides.", Pure Appl. Chem., 2003, pp. 63-70, vol. 75(1).

Greene et al., "Protective Groups in Organic Synthesis.", 3rd Edition, 1999, pp. 116-121.

Adachi et al., "T-1095, a Renal Na+-Glucose Transporter Inhibitor, Improves Hyperglycemia in Streptozotocin-Induced Diabetic Rats.", Metabolism, Aug. 2000, pp. 990-995, vol. 49(8).

Albertoni Borghese et al., "Inhibitors of sodium/glucose cotransport.", Drugs of The Future, Apr. 2009, pp. 297-305, vol. 34(4), Prous Science, XP007915342.

Ahmad et al., "Synthesis And Structure Determination of Some Oxadiazole-2-Thione and Triazole-3-Thione Galactosides.", Nucleosides, Nucleotides & Nucleic Acids, 2001, pp. 1671-1682, vol. 20(9).

Amishiro et al., "Synthesis and Antitumor Activity of Duocarmycin Derivatives: A-Ring Pyrrole Compounds Bearing 5-Membered Heteroarylacryloyl Groups," Chem. Pharm. Bull., Oct. 1999, pp. 1393-1403, vol. 47(10).

Appleton et al., "A Mild and Selective C-3 Reductive Alkylation of Indoles", Tetrahedron Letters, 1993, pp. 1529-1532, vol. 34(9).

Banker, Modern Pharmaceutics, Third Edition, Marcel Dekker, Inc., published 1996, p. 596.

Beck-Nielsen et al., "In Vivo Glucose Metabolism, Insulin Secretion and, Insulin Action in Europids with non-insulin-dependent Diabetes mellitus (NIDDM) and Their First-degree Relatives.", Diabetic Medicine, Sep. 1996, pp. S78-S84, vol. 13(9 Supp. 6).

Benhaddou et al., "Tetra-n-propylammonium tetra-oxoruthenate(VII): a reagent of choice for the oxidation of diversely protected glycopyranoses and glycofuranoses to lactones", Carbohydrate Research, 1994, pp. 243-250, vol. 260.

Bertolini et al., "A New Simple One-Pot Regioselective Preparation of Mixed Diesters of Carbonic Acid.", Journal of Organic Chemistry, 1998, pp. 6031-6034, vol. 63(17).

Blair et al., "Effect of Ring Fluorination on the Pharmacology of Hallucinogenic Tryptamines", J. Med. Chem., 2000, pp. 4701-4710, vol. 43.

Boehm et al., "Novel Inhibitors of DNA Gyrase: 3D Structure Based Biased Needle Screening, Hit Validation by Biophysical Methods, and 3D Guided Optimization. A Promising Alternative to Random Screening," J. Med. Chem., 2000, pp. 2664-2674, vol. 43(14).

Bookser, B.C., "2-Benzyloxymethyl-5-(tributylstannyptetrazole. A reagent for the preparation of 5-aryl- and 5-heteroaryl-1H-tetrazoles via the Stille reaction," Tetrahedron Letters, 2000, pp. 2805-2809, vol. 41.

Bouillon et al., "Synthesis of novel halopyridinylboronic acids and esters. Part 2: 2,4, or 5-Halopyridin-3-yl-boronic acids and esters," Tetrahedron, 2002, pp. 3323-3328, vol. 58.

Bouillon et al., "Synthesis of novel halopyridinylboronic acids and esters. Part 3: 2, or 3-Halopyridin-4-yl-boronic acids and esters," Tetrahedron, 2002, pp. 4369-4373, vol. 58.

Bouillon et al., "Synthesis of novel halopyridinylboronic acids and esters. Part 4: Halopyridin-2-yl-boronic acids and esters are stable, crystalline partners for classical Suzuki cross-coupling," Tetrahedron, 2003, pp. 10043-10049, vol. 59.

Braga et al., "Making crystals from crystals: a green route to crystal engineering and polymorphism.", Chem. Commun., 2005, pp. 3635-3645.

Brooks et al., "Boron Trichloride/Tetra-n-Butylammonium Iodide: A Mild, Selective Combination Reagent for the Cleavage of Primary Alkyl Aryl Ethers", J. Org. Chem., 1999, pp. 9719-9721, vol. 64.

CAS Reg. No. 487001-40-1, IPOrganisers, Entered STN Feb. 7, 2003, pp. 1-2.

Caumo et al., "Insulin Sensitivity from Meal Tolerance Tests in Normal Subjects: A Minimal Model Index.", J. of Clinical Endocrinology & Metabolism, 2000, pp. 4396-4402, vol. 85(11).

Cicchillo et al., "A convenient synthesis of glycosyl chlorides from sugar hemiacetals using triphosgene as the chlorine source," Carbohydrate Research, 2000, pp. 431-434, vol. 328.

Clayden et al., "Dearomatizing Cyclization of Arylsulfonylalkoxymethyl Lithiums: A Route to the Podophyllotoxin Skeleton," Organic Letters, 2003, pp. 831-834, vol. 5(6).

Comins et al., "Synthesis of 3-Substituted Indoles Via N-Acylindolium Ions", Tetrahedron Letters, 1986, pp. 1869-1872, vol. 27(17).

Cottet et al., "Recommendable Routes to Trifluoromethyl-Substituted Pyridine- and Quinolinecarboxylic Acids," Eur. J. Org. Chem., 2003, pp. 1559-1568.

Czernecki et al., "C-Glycosides. 7. Stereospecific C-Glycosylation of Aromatic and Heterocyclic Rings", J. Org. Chem., 1989, pp. 610-612, vol. 54.

(56) References Cited

OTHER PUBLICATIONS

De Las Heras et al., "Alkylating Nucleosides 1. Synthesis and Cytostatic Activity of N-Glycosyl(halomethyl)-1,2,3-triazoles. A New Type of Alkylating Agent," Journal of Medicinal Chemistry, 1979, pp. 496-501, vol. 22(5).

Deeg et al., "Pioglitazone and Rosiglitazone Have Different Effects on Serum Lipoprotein Particle Concentrations and Sizes in Patients With Type 2 Diabetes and Dyslipidemia.", Diabetes Care, Oct. 2007, pp. 2458-2464, vol. 30(10).

Deetjen et al., "Renal Handling of D-Glucose and Other Sugars", Textbook of Nephrology, 3rd Edition, 1995, pp. 90-94. vol. 1.

Devivar et al., "Benzimidazole Ribonucleosides: Design, Synthesis, and Antiviral Activity of Certain 2-(Alkylthio)- and 2-(Benzylthio)-5,6-dichloro-1-(β-D-ribofuranosyl)benzimidazolesl.", J.Med. Chem., 1994, pp. 2942-2949, vol. 37.

Dewynter et al., "Synthesis of Pseudomucleosides containing Chiral Sulfahydantoins as Aglycone (II)", Tetrahedron, 1996, pp. 993-1004, vol. 52(3).

Dillard et al., "Indole Inhibitors of Human Nonpancreatic Secretory Phospholipase A2. 1. Indole-3-acetamides", J. Med. Chem., 1996, pp. 5119-5136, vol. 39.

Dinneen, S.F., "The Postprandial State: Mechanisms of Glucose Intolerance.", Diabetic Medicine, Aug. 1997, pp. S19-S24, vol. 14, Issue S3.

Dondoni et al., "Stereoselective synthesis of C-glycosylphosphonates from their ketols. Reconsideration of an abandoned route", Tetrahedron: Asymmetry, 2000, pp. 305-317, vol. 11.

Dondoni et al., "Thiazole-Based Synthesis of Formyl C-Glycosides", J. Org. Chem., 1994, pp. 6404-6412, vol. 59.

Dudash et al., "Glycosylated dihydrochalcones as potent and selective sodium glucose co-transporter 2 (SGLT2) inhibitors," Bioorganic & Medicinal Chemistry Letters, 2004, pp. 5121-2125, vol. 14.

Dunn et al., "Analgetic and antiinflammatory 7-Aroylbenzofuran-5-ylacetic acids and 7-Aroylbenzothiophene-5-ylacetic Acids.", Journal of Med. Chem., 1986, pp. 2326-2329, vol. 29(1).

Eid et al., "Reaction of Some 1,2,4-Triazines with Acetobromoglucose", Arch. Pharm (Weinheim), 1990, pp. 243-245, vol. 323.

Ellsworth et al., "Aglycone exploration of C-arylglucoside inhibitors of renal sodium-dependent glucose transporter SGLT2," Bioorganic & Medicinal Chemistry Letters, 2008, pp. 4770-4773, vol. 18.

Ellsworth et al., "C-Arylglucoside synthesis: triisopropylsilane as a selective reagent for the reduction of an anomeric C-phenyl ketal," Tetrahedron: Asymmetry, 2003, pp. 3243-3247, vol. 14.

Emancipator, K., "Laboratory diagnosis and monitoring of diabetes mellitus.", Am J Clin Pathol., Nov. 1999, pp. 65-674, vol. 112(5).

Frahn et al., "Functionalized AB-Type Monomers for Suzuki Polycondensation," Synthesis, Nov. 1997, pp. 1301-1304.

Fresneda et al., "Synthesis of the indole alkaloids meridianins from the tunicate *Aplidium meridianum*" Tetrahedron, 2001, pp. 2355-2363, vol. 57.

Fuller et al., "Thienothiophenes. Part 2. Synthesis, metallation and bromine-lithium exchange reactions of thieno[3,2-b-thiophene and its polybromo derivatives," J. Chem. Soc., Perkin Trans. 1., 1997, pp. 3465-3470.

Ganesh et al., "Synthesis and biological evaluation of fluorescently labeled epothilone analogs for tubulin binding studies," Tetrahedron, 2003, pp. 9979-9984, vol. 59.

Gershell, L., "Type 2 diabetes market", Nature Reviews Drug Discovery, May 2005, pp. 367-368, vol. 4.

Gohier et al., "ortho-Metalation of Unprotected 3-Bromo and 3-Chlorobenzoic Acids with Hindered Lithium Dialkylamides," J. Org. Chem., 2003, pp. 2030-2033, vol. 68.

Goldberg R.B., "Prevention of Type 2 Diabetes.", Medical Clinics of North America, Jul. 1998, pp. 805-821, vol. 82(4).

Gong, H., et al., "Diasteroselective Ni-Catalyzed negishi Cross Coupling Approach to Saturated, Fully Oxygenated C-Alkyl and C-Aryl Glycosides.", Journal of The American Chemical Society, Sep. 10, 2008, pp. 12177-12183, vol. 130(36), XP002612364.

Goodman & Gilman'S the Pharmacological Basis of Therapeutics, 10th Edition, McGraw-Hill Medical Publishing Division, 2001, pp. 54-57.

Gronowitz et al., "Some Substitution Reactions of 1-(2-Thienyl)pyrazole and 1-(3'-Thienyl)pyrazole," Chemica Scripta., 1979, pp. 157-161, vol. 13.

Groop et al., "Characterization of the Prediabetic State.", American Journal of Hypertension, Sep. 1997, pp. 172S-180S, vol. 10(9Part2).

Gros et al., "Efficient and Regioselective Access to Bis-heterocycles via Palladium-Catalysed Coupling of Organostannanes and Organozincates Derived from C-6 Lithiated 2-Methoxypyridine," Synthesis, 1999, pp. 754-756, No. 5.

Haffner S.M., "Impaired Glucose Tolerance, Insulin Resistance and Cardiovascular Disease.", Diabetic Medicine, Aug. 1997, pp. S12-S18, vol. 14.

Haffner S.M., "The Prediabetic Problem: Development of Non-Insulin-Dependent Diabetes Mellitus and Related Abnormalities.", Journal of Diabetes and Its Complications, Mar.-Apr. 1997, pp. 69-76, vol. 11(2).

Han et al., "Dapagliflozin, a Selective SGLT2 Inhibitor, Improves Glucose Homeostasis in Normal and Diabetic Rats", Diabetes, Jun. 2008, pp. 1723-1729, vol. 57, New York.

Handlon, A. L., "Sodium glucose co-transporter 2 (SGLT2) inhibitors as potential antidiabetic agents," Expert Opin. Ther. Patents, 2005, pp. 1531-1540, vol. 15(11).

Hixon et al., "Sizing Materials By Crushing and Grinding.", Chemical Engineer, Nov. 1990, pp. 94-103.

Hofslokken et al., "Convenient Method for the ortho-Formylation of Phenols.", Acta Chemica Scandinavica, 1999, pp. 258-262, vol. 53.

Horton et al., "Synthetic Routes to Higher-Carbon Sugars. Reaction of Lactones with 2-Lithio-1,3-Dithiane", Carbohydrate Research, 1981, pp. 27-41, vol. 94.

Hu et al., "A New Approach Towards the Yellowing Inhibition of Mechanical Pulps. Part I: Selective Removal of alpha-Hydroxyl and alpha-Carbonyl Groups in Lignin Model Compounds", Holzforschung, 1999, pp. 43-48, vol. 53(1).

Huang-Minlon, "Reduction of Steroid Ketones and other Carbonyl Compounds by Modified Wolff-Kishner Method", J. Am. Chem. Soc., Oct. 1949, pp. 3301-3303, vol. 71.

Ibrahim et al., "Facile Approach for the Selective Glycodisation of Cyclic Asymmetric Amides and Thioamides", Carbohydrate Letters, 1996, pp. 425-432, vol. 1.

Ibrahim et al., "Selective Synthesis and Structure of 2-N- and 3-S-Glucosyl-1,2,4-Triazoles of Potential Biological Interest", Carbohydrate Letters, 1999, pp. 331-338, vol. 3(5).

Idris et al., "Sodium-glucose co-transporter-2 inhibitors: an emerging new class of oral antidiabetic drug.", Diabetes, Obesity and Metabolism, 2009, pp. 79-88, vol. 11(2), GB, XP007915350.

Isaji, M., "Sodium-glucose cotransporter inhibitor for diabetes," Current Opinion in Investigational Drugs, 2007, pp. 285-292, vol. 8(4).

Jain et al., "Polymorphism in Pharmacy.", Indian Drugs, 1986, pp. 315-329, vol. 23(6).

Kanai et al., "The Human Kidney Low Affinity Na+/Glucose Cotransporter SGLT2: Delineation of the Major Renal Reabsorptive Mechanism for D-Glucose", J. Clin. Invest., Jan. 1994, pp. 397-404, vol. 93.

Kasahara et al., "A missense mutation in the Na+/glucose cotransporter gene SGLT1 in a patient with congenital glucose-galactose malabsorption: normal trafficking but inactivation of the mutant protein," Biochimica et Biophysics Acta, 2001, pp. 141-147, vol. 1536.

Katz et al., "Quantitative Insulin Sensitivity Check Index: A Simple, Accurate Method for Assessing Insulin Sensitivity in Humans.", J. Of Clin. Endocrinology & Metabolism, 2000, pp. 2040-2410, vol. 85(7).

Ketcha et al., "Synthesis of Alyl-Substituted N-Protected Indoles via Acylation and Reductive Deoxygenation1" J. Org. Chem., 1989, pp. 4350-4356, vol. 54.

(56) References Cited

OTHER PUBLICATIONS

Khan et al, "Reactions of Phenyl-Substituted Heterocyclic Compounds—II. Nitrations and Brominations of 1-Phenylpyrazole Derivatives," Canadian Journal of Chemistry, 1963, pp. 1540-1547, vol. 41.
Kitagawa, K., et al., "Halogen-Magnesium Exchange via Trialkylmagnesates for the Preparation of Aryl- and Alkenylmagnesium Reagents", Angew. Chem. Int. Ed., 2000, pp. 2481-2493, vol. 39(14).
Knochel, P., et al., Organic Reactions, vol. 58, Chapter 2: Preparation and Application of Functionalized Organozinc Compounds by., pp. 417-490, Edited by L. E. Overman, et al., John Wiley & Sons, Inc., Publishers.
Lee et al., "Synthesis and in Vitro Activity of Novel Isoxazolyl Tetrahydropyridinyl Oxazolidinone Antibacterial Agents," Bioorganic & Medicinal Chemistry Letters, 2003, pp. 4117-4120, vol. 13.
Lieberman et al., "Pharmaceutical Dosage Forms.", Second Edition, 1990, Marcel Dekker Inc., pp. 462-472, vol. 2.
Lin et al., "Syntheses of Guanidinoglycosides with the Inventive use of Mitsunobu Conditions and 1, 8-Diazabicyclo[5.4.0]undec-7-ene.", Synthesis, 2003, pp. 255-261, No. 2.
Link et al., "A method for preparing C-glycosides related to phlorizin" Tetrahedron Letters, 2000, pp. 9213-9217, vol. 41.
Lipscombe et al., "Trends in diabetes prevalence, incidence, and mortality in Ontario, Canada 1995-2005: a population-based study", Lancet, 2007, vol. 369, pp. 750-756.
Mackenzie et al., "Biophysical Characteristics of the Pig Kidney Na+/Glucose Cotransporter SGLT2 Reveal a Common Mechanism for SGLT1 and SGLT2", J. Biol. Chem., 1996, vol. 271, pp. 32678-32683, No. 5.
Manis et al., "Metabolism of 4,4'-Methylenebis(2-chloroaniline) by Canine Liver and Kidney Slices.", Drug Metabolism and Disposition, 1986, pp. 166-174, vol. 14(2).
Marsenic, O. MD, "Glucose Control by the Kidney: An Emerging Target in Diabetes.", Am. J. of Kidney Diseases, May 2009, pp. 875-883, vol. 53(5).
Matsuda et al., "Insulin Sensitivity Indices Obtained From Oral Glucose Tolerance Testing: Comparison with the euglycemic insulin clamp," Diabetes Care, Sep. 1999, pp. 1462-1470, vol. 22(9).
Matthews et al., "Homeostasis model assessment: insulin resistance and—cell function from fasting plasma glucose and insulin concentrations in man," Diabetolgia, 1985, pp. 412-419, vol. 28.
Meanwell et al., "Regiospecific Functionalization of 1,3-Dihydro-2H-benzimidazol-2-one and Structurally Related Cyclic Urea Derivates.", J. Org. Chemistry, 1995, pp. 1565-1582, vol. 60(6).
Meng et al., "Discovery of Dapagliflozin: a Potent, Selective Renal Sodium-Dependent Glucose Cotransporter 2 (SGLT2) Inhibitor for the Treatment of Type 2 Diabetes", J. Med. Chem., 2008, pp. 1145-1149, vol. 51(5).
Messaoudi et al, "Synthesis and biological evaluation of oxindoles and benzimidazolinones derivatives," European Journal of Medicinal Chemistry, 2004, pp. 453-458, vol. 39.
Mewshaw et al., "New Generation Dopaminergic Agents. 7. Heterocyclic Bioisosteres that Exploit the 3-Oh-Phenoxyethylamine D2 Template", Bioorganic & Medicinal Chemistry Letters, 1999, pp. 2593-2598, vol. 9.
Miyaura et al., "Palladium-Catalyzed Cross-Coupling Reactions of Organoboron Compounds.", Chem. Rev., 1995, pp. 2457-2583, vol. 95(7).
Mongin, F., et al., "Deprotonation of furans using lithium magnesates", Tetrahedron Lett., 2005, pp. 7989-7992, vol. 46.
Nishimura et al, "Tissue-specific mRNA Expression Profiles of Human ATP-binding Cassette and Solute Carrier Transporter Superfamilies," Drug Metab. Pharmacokinet., 2005, pp. 452-477, vol. 20(6).
Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2010, pp. 6355-6360, vol. 53(17), American Chemical Society, US, XP007915324.
Nomura, S., "Renal Sodium-Dependent Glucose Cotransporter 2 (SGLT2) Inhibitors for New Anti-Diabetic Agent," Current Topics in Medicinal Chemistry, 2010, pp. 411-418, vol. 10(4).
Ohsumi et al. "Pyrazole-O-Glucosides as Novel Na+-Glucose Cotransporter (SGLT) Inhibitors" Bioorganic & Medicinal Chemistry Letters, 2003, pp. 2269-2272, vol. 13.
Oku et al., "T-1095, an Inhibitor of Renal Na+-Glucose Cotransporters, May Provide a Novel Approach to Treating Diabetes", Diabetes, Sep. 1999, pp. 1794-1800, vol. 48.
Orjales et al. "New 2-Piperazinylbenzimidazole Derivatives as 5-HT-3 Antagonists. Synthesis and Pharmacological Evaluation," J. Med. Chem., 1997, pp. 586-593, vol. 40.
Parker et al., "Reductive Aromatization of Quinols: Synthesis of the C-Arylglycoside Nucleus of the Paulacandins and Chaetiacandin," Organic Letters, 2000, pp. 497-499, vol. 2(4).
Parrott, E.L., "Milling of pharmaceutical solids.", Journal of Pharmaceutical Sciences, Jun. 1974, pp. 813-829, vol. 63(6).
Patani et al., "Bioisosterism: A Rational Approach in Drug Design", Chem. Rev., American Chemical Society, 1996, pp. 3147-3176, vol. 96.
Peng et al., "Post-transcriptional Regulaton of Na+/Glucose Cotransporter (SGTL1) Gene Expression in LLC-PK1 Cells.", Journal of Biological Chemistry, 1995, pp. 20536-20542, vol. 270(35).
Perry's Chemical Engineers Handbook, Sixth Edition, 1984, pp. 21-13 to 21-19.
Pharmaceutical Sciences, Remington, 17th Ed., pp. 1585-1594 (1985).
Ramlo-Halsted B.A. & Edelman S.V., "The Natural History of Type 2 Diabetes Mellitus: Implications for Clinical Practice.", Primary Care, Dec. 1999, pp. 771-789, vol. 26(4).
Raynaud et al., "Revised Concept for the Estimation of Insulin Sensitivity From a Single Sample.", Diabetes Care, Jun. 1999, pp. 1003-1004, vol. 22(6).
Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.
Schultheiss et al., "Pharmaceutical Cocrystals and Their Physicochemical Properties.", Crystal Growth and Design, Jun. 3, 2009, pp. 2950-2967, vol. 9(6), XP55011939.
Shan et al., "The role of cocrystals in pharmaceutical science.", Drug Discovery Today, May 1, 2008, pp. 440-446, vol. 13(9-10), Elsevier, Rahway, NJ, US, XP022649919.
Silverman, R. B., "The Organic Chemistry of Drug Design and Drug Action," Academic Press, 1992, pp. 19-23.
Somei et al., "The First and Simple Total Synthesis of Cappariloside Ai," Heterocycles, 2000, pp. 1573-1578, vol. 53(7).
Stoner et al., "Benzylation via Tandem Grignard Reaction—Lodotrimethylsilane (TMSI) Mediated.Reduction," Tetrahedron, 1995, pp. 11043-11062, vol. 51(41).
Stumvoll et al., "Use of the Oral Glucose Tolerance Test to Assess Insulin Release and Insulin Sensitivity.", Diabetes Care, Mar. 2000, pp. 295-301, vol. 23(3).
Tanaka et al. "Solid-Phase Synthesis of—Mono-Substituted Ketones and an Application to the Synthesis of a Library of Phlorizin Derivatives", Synlett, 2002, pp. 1427-1430, No. 9.
Thornber, C.T., "Isosterism and Molecular Modification in Drug Design.", Chem. Society Review, 1979, pp. 563-580, vol. 8.
Tilak et al, "Carcinogenesis by Thiophene Isosters of Polycyclic Hydrocarbons," Tetrahedron, 1960, pp. 76-95, vol. 9.
Tsujihara et al., Bio Clinica, 1998, pp. 324-328, vol. 13(4), English language Abstract.
Turk et al., "Glucose/galactose malabsorption caused by a defect in the Na+/glucose cotransporter," Nature, Mar. 1991, pp. 354-356, vol. 350.
Vippagunta et al., "Crystalline Solids" Advanced Drug Delivery Reviews, 2001, pp. 3-26, vol. 48.

(56) References Cited

OTHER PUBLICATIONS

Vishweshwar et al., "Pharmaceutical co-crystals.", Journal of Pharmaceutical Sciences, Mar. 1, 2006, pp. 499-516, vol. 95(3), American Pharmaceutical Association, Washington, US.
Wallace et al., "Use and Abuse of Homa Modeling.", Diabetes Care, Jun. 2004, pp. 1487-1495, vol. 27(6).
Wang et al, "Selective monolithiation of 2,5-dibromopyridine with butyllithium," Tetrahedron Letters, 2000, pp. 4335-4338, vol. 41.
Wareham et al., "Is There Really an epidemic of diabetes?", Diabetologia, 2005, pp. 1454-1455, vol. 48.
Washburn, W. N., "Evolution of sodium glucose co-transporter 2 inhibitors as anti-diabetic agents," Expert Opin. Ther. Patents, 2009, pp. 1485-1499, vol. 19(11).
Watanabe et al., "Cyclopentyl Methyl Ether as a New and Alternative Process Solvent.", Organic Process Research and Development, 2007, pp. 251-258, vol. 11.
Wild et al., "Global Prevalence of Diabetes: Estimates for the year 2000 and projections for 2030," Diabetes Care, May 2004, pp. 1047-1053, vol. 27(5).
Wolff, M. E., vol. 1: Principles and Practice, Burger's Medicinal Chemistry and Drug Discovery, 5th Edition, 1995, pp. 975-977.
Wright, E.M., "Renal Na+-glucose cotransporters," Am J Physiol Renal Physiol, 2001, pp. F10-F18, vol. 280.
Wurster D.E., "Air-suspension Technique of Coating Drug Particles A Preliminary Report.", Journal of the American Pharmaceutical Association, Aug. 1959, pp. 451-454, vol. 48(8).
Wurster, D.E., "Preparation of compressed tablet granulations by the air-suspension technique II.", Journal of the American Pharmaceutical Association, 1960, pp. 82-84, vol. 49(2).
Yang et al., "Convergent C-Glycolipid Synthesis via the Ramberg-Backlund Reaction: Active Antiproliferative Glycolipids", Org. Lett. 1999, pp. 2149-2151, vol. 1913).
Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives," J. Med. Chem., 2000, pp. 2929-2937, vol. 43.
Zhou, F. Y., "The Synthesis and Characterization of 1-Benzyl-3-N-(Beta-D-glucosie-1-yl)-4-fluorouracil", Hecheng Huaxue, 2001, pp. 272-274, vol. 9(3).
Zhdanov, Y. et al., "Application of organozinc compounds in the synthesis of carbon—carbon derivatives of sugars.", Database CA (online), Chemical Abstract Service, Columbus, Ohio, USA, XP002612365.
Translation—Zhdanov, Y. et al., "Application of organozinc compounds in the synthesis of carbon—carbon derivatives of sugars.", Database CA (online), Chemical Abstract Service, Columbus, Ohio, USA, XP002612365.
Knochel, P., et al., Organic Reactions, vol. 58, Chapter 2: Preparation and Application of Functionalized Organozinc Compounds, 2001, pp. 417-490, Edited by L. E. Overman, et al., John Wiley & Sons, Inc., Publishers.
Zhdanov, Y. et al., "Application of organozinc compounds in the synthesis of carbon—carbon derivatives of sugars.", 2001, Database CA (online), Chemical Abstracts Service, Columbus, Ohio, USA, XP002612365.
Translation—Zhdanov, Y. et al., "Application of organozinc compounds in the synthesis of carbon—carbon derivatives of surgars.", 2001, Database CA (online), Chemical Abstracts Service, Columbus, Ohio, USA, XP002612365.
Jianqun, et al., "Recent advances in palladium catalysts for aryl chlorides coupling reaction", Industrial Catalysis, Jul. 31, 2005, pp. 29-44, vol. 13(7).
Zhiyin, et al., "Cross-coupling reaction of Grignard reagent with thiophenyl halides by using nickel phoshine as catalyst and the synthesis of α-terthienyl", Huaxue Shiji, Dec. 31, 1995, pp. 289-290, vol. 17(5).
First Office Action relating to China Patent Application No. 201310358939.0, Issued on May 29, 2014.
Asahara et al. Handbook of Solvents, K.K. Kodansha., Sep. 1, 1985, Sixth Printing, pp. 47-51, Tokyo, JP.
Byrn et al., "Pharmaceutical Solids: A Strategic Approach to Regulatory Considerations.", Pharml. Res., 1995, pp. 945-954, vol. 12(7).
Bavin, M., "Process Development: Polymorphism in Process Development.", Chemistry & Industry, 1989, pp. 527-529, vol. 16.
Kozikowski et al., "Organometallics in Organic Synthesis. Applications of a New Diorganozinc Reaction to the Synthesis of C-Glycosyl Compounds With Evidence for an Oxonium-Ion Mechanism.", Carbohydrate Research, 1987, pp. 109-124, vol. 171.
Schmidt et al., "Synthese von Pyrazol-, Pyrazolo[3,4-d]pyrimidin- und 1H-1,2,4-Triazolgluconucleosiden aus Glucosehydrazonen," Liebigs Ann. Chem., 1981, pp. 2309-2317.
Brandsma et al., "Nickel- and Palladium-Catalyzed Cross-Coupling Reactions With Organometallic Intermediates.", Application of Transition Metal Catalysts in Organic Synthesis, 1999, Chapter 11, pp. 227-230, 243-246, 250-252, 258, 261, 273, Springer-Verlag Berlin Heidelberg, Germany.
Kravovskiy et al., "A LiCl-Mediated Br/Mg-exchange reaction for produce functionalized aryl- and heteroarylymagnesium connections starting from organic bromides.", Angew. Chem., 2004, pp. 3396-3399, vol. 116.
Kravovskiy et al., "Highly efficient reagents for the bromine—magnesium exchange.", Angew. Chem., 2006, pp 165-169, vol. 118.

PROCESS FOR THE PREPARATION OF COMPOUNDS USEFUL AS INHIBITORS OF SGLT

CROSS REFERENCE TO RELATED APPLICATIONS

This application claims the benefit of U.S. Provisional Application No. 61/106,231, filed on Oct. 17, 2008 and U.S. Provisional Application No. 61/106,260, filed on Oct. 17, 2008, which are incorporated by reference herein in their entirety.

FIELD OF THE INVENTION

The present invention is directed to a novel process for the preparation of compounds having inhibitory activity against sodium-dependent glucose transporter (SGLT) being present in the intestine or kidney.

BACKGROUND OF THE INVENTION

Diet therapy and exercise therapy are essential in the treatment of diabetes mellitus. When these therapies do not sufficiently control the conditions of patients, insulin or an oral antidiabetic agent is additionally used for the treatment of diabetes. At the present, there have been used as an antidiabetic agent biguanide compounds, sulfonylurea compounds, insulin resistance improving agents and α-glucosidase inhibitors. However, these antidiabetic agents have various side effects. For example, biguanide compounds cause lactic acidosis, sulfonylurea compounds cause significant hypoglycemia, insulin resistance improving agents cause edema and heart failure, and α-glucosidase inhibitors cause abdominal bloating and diarrhea. Under such circumstances, it has been desired to develop novel drugs for treatment of diabetes mellitus having no such side effects.

Recently, it has been reported that hyperglycemia participates in the onset and progressive impairment of diabetes mellitus, i.e., glucose toxicity theory. Namely, chronic hyperglycemia leads to decrease of insulin secretion and further to decrease of insulin sensitivity, and as a result, the blood glucose concentration is increased so that diabetes mellitus is self-exacerbated [Unger, R. H., et al., "Hyperglycemia as an inducer as well as a consequence of impaired islet cell function and insulin resistance: implication for the management of diabetes", *Diabetologia*, 1985, vol. 28, pp 119-121; Rossetti, L., et al., "Glucose Toxicity", *Diabetes Care*, 1990, vol. 13, no. 6, pp 610-630;]. Therefore, by treating hyperglycemia, the aforementioned self-exacerbating cycle is interrupted so that the prophylaxis or treatment of diabetes mellitus is made possible.

As one of the methods for treating hyperglycemia, it is considered to excrete an excess amount of glucose directly into urine so that the blood glucose concentration is normalized. For example, by inhibiting sodium-dependent glucose transporter being present at the proximal convoluted tubule of kidney, the re-absorption of glucose at the kidney is inhibited, by which the excretion of glucose into urine is promoted so that the blood glucose level is decreased. In fact, it is confirmed that by continuous subcutaneous administration of phlorizin having SGLT inhibitory activity to diabetic animal models, hyperglycemia is normalized and the blood glucose level thereof can be kept normal for a long time so that the insulin secretion and insulin resistance are improved [Rossetti, L., et al., "Correction of Hyperglycemia with Phlorizin Normalizes Tissue sensitivity to Insulin in Diabetic Rats", *J. Clin. Invest.*, 1987, vol. 79, pp 1510-1515; Rossetti, L., et al., "Effect of Chronic Hyperglycemia on in Vivo Insulin Secretion in Partially Pancreatectomized Rats", *J. Clin Invest.*, 1987, vol. 80, pp 1037-1044; Kahn, B. B., et al., "Normalization of blood glucose in diabetic rats with phlorizin treatment reverses insulin-resistant glucose transport in adipose cells without restoring glucose transporter gene expression", *J. Clin. Invest.*, 1991, vol. 87, pp 561-570]

In addition, by treating diabetic animal models with SGLT inhibitory agents for a long time, insulin secretion response and insulin sensitivity of the animals are improved without incurring any adverse affects on the kidney or imbalance in blood levels of electrolytes, and as a result, the onset and progress of diabetic nephropathy and diabetic neuropathy are prevented [Tsujihara, K., et al., "Na+-Glucose Cotransporter (SGLT) Inhibitors as Antidiabetic Agents. 4. Synthesis and Pharmacological Properties of 4'-Dehydroxyphlorizin Derivatives Substituted on the B Ring", *J. Med. Chem.*, 1999, vol. 42, pp 5311-5324; Arakawa, K., et al., "Improved diabetic syndrome in C57BL/Ks-db/db mice by oral administration of the Na+-glucose cotransporter inhibitor T-1095, *Br. J. Pharmacol.*, 2001, vol. 132, pp 578-586; Ueta, K., et al., "Long-term treatment with the Na+-glucose cotransporter inhibitor T-1095 causes sustained improvement in hyperglycemia and prevents diabetic neuropathy in Goto-kakizaki Rats", *Life Sciences*, 2005, vol. 76, pp 2655-2668] [From the above, SGLT inhibitors may be expected to improve insulin secretion and insulin resistance by decreasing the blood glucose level in diabetic patients and further prevent the onset and progress of diabetes mellitus and diabetic complications.

Nomura, S., et al., United States Patent Application Publication No. 2005/0233988, published Oct. 20, 2005, discloses SGLT inhibitors and preparation methods thereof.

SUMMARY OF THE INVENTION

The present invention is directed to a process for the preparation of compounds of formula (I)

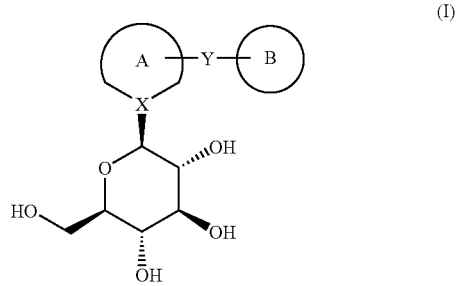

wherein Ring A and Ring B are one of the following:

(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or (3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;

Y is —$(CH_2)_n$—; wherein n is 1 or 2;

provided that in Ring A, X is part of an unsaturated bond;

or a pharmaceutically acceptable salt or solvate thereof; comprising

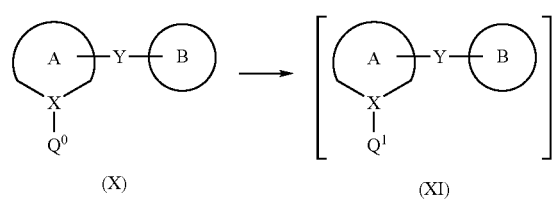

(X)    (XI)

reacting a compound of formula (X) wherein $Q^0$ is bromo or iodo, with a complex of di($C_{1-4}$alkyl)magnesium with lithium chloride or a complex of $C_{1-4}$alkyl magnesium chloride with lithium chloride or a complex of $C_{1-4}$alkyl magnesium bromide with lithium chloride; in an organic solvent or mixture thereof; at a temperature in the range of from about ambient temperature to about −78° C.; to yield the corresponding compound of formula (XI), wherein $Q^1$ is the corresponding MgCl or MgBr;

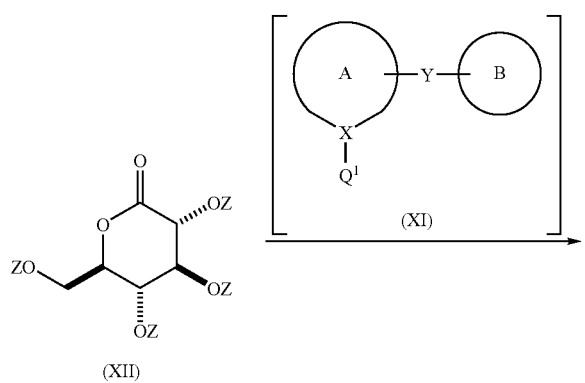

(XII)

reacting the compound of formula (XI) with a compound of formula (XII), wherein Z is an oxygen protecting group; in an organic solvent or mixture thereof; at a temperature in the range of from about ambient temperature to about −78° C.; to yield the corresponding compound of formula (XIII);

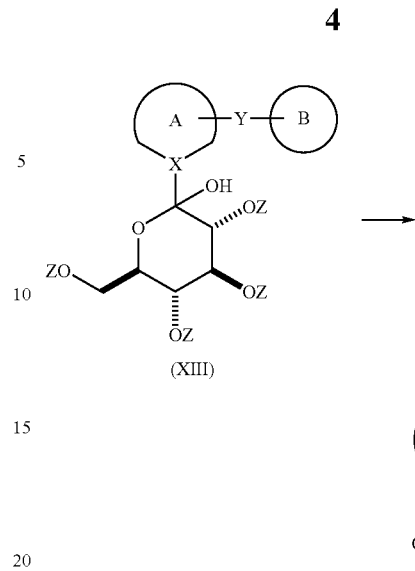

(XIII)

(XIV)

reacting the compound of formula (XIII) with a Lewis acid; in the presence of a silane reagent; in an organic solvent or mixture thereof; at a temperature in the range of from about 0° C. to about reflux; to yield the corresponding compound of formula (XIV);

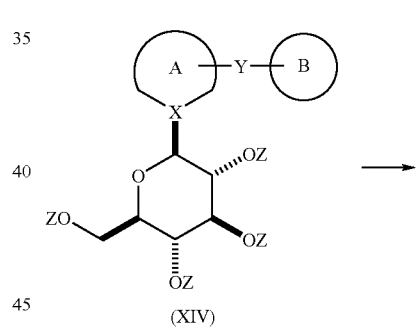

(XIV)

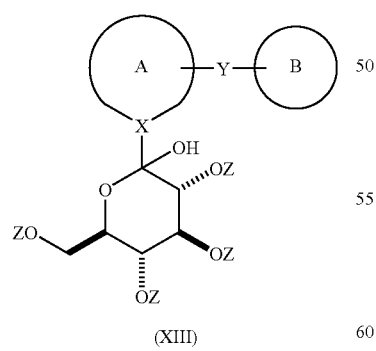

(XIII)

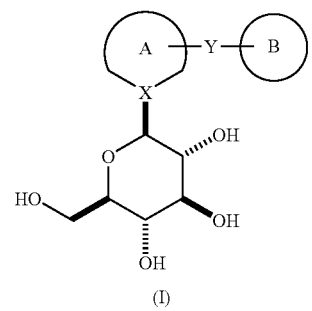

(I)

de-protecting the compound of formula (XIV); to yield the corresponding compound of formula (I).

In an embodiment, the present invention is directed to a novel process for the preparation of compounds of formula (IA')

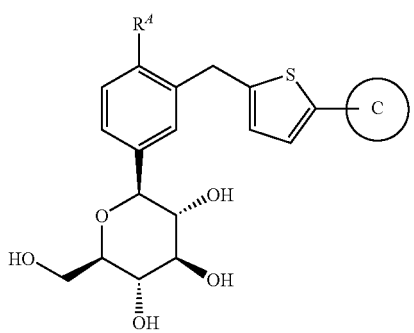
(IA′)

wherein
$R^A$ is halogen or lower alkyl;

Ring C is phenyl substituted with 1-3 substituents selected from the group consisting of halogen, cyano, lower alkyl, halo-lower alkyl, lower alkoxy, halo-lower alkoxy, methylenedioxy, ethyleneoxy, mono- or di-lower alkylamino, carbamoyl, and mono- or di-lower alkylcarbamoyl;

or heterocyclyl substituted by 1-3 substituents selected from the group consisting of halogen, cyano, lower alkyl, halo-lower alkyl, lower alkoxy, halo-lower alkoxy, mono- or di-lower alkylamino, carbamoyl, and mono- or di-lower alkylcarbamoyl;

and pharmaceutically acceptable salts thereof; comprising steps of:

reacting a compound of formula (L) wherein $X^0$ is selected from the group consisting of Cl, Br, I and Cl·LiCl or a compound of formula (LI) with a compound of formula (LII), wherein $R^1$ is tri-lower alkyl silyl; to yield the corresponding compound of formula (LIII);

(LIII)

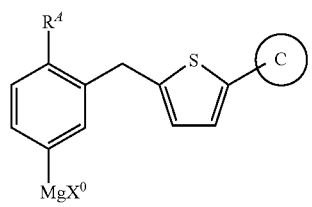
(L)

or

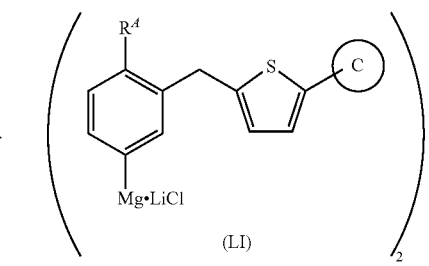
(LI)

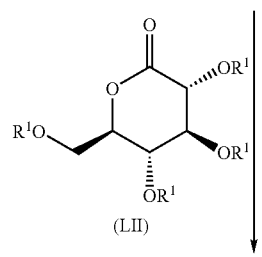
(LII)

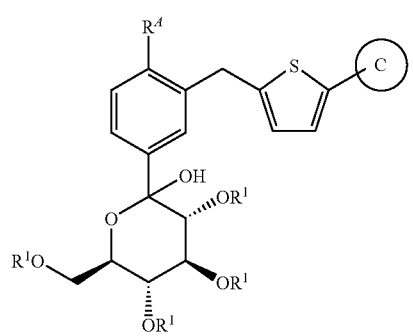
(LIII)

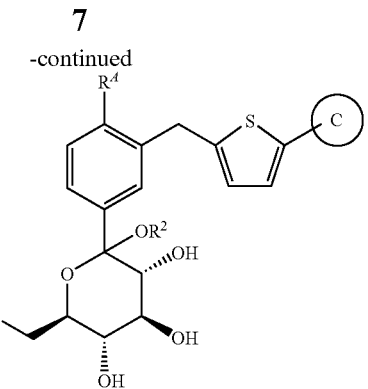

(LV)

reacting the compound of formula (LIII) with an alcohol of formula (LIV), wherein $R^2$ is lower alkyl; in the presence of an acid; to yield the corresponding compound of formula (LV);

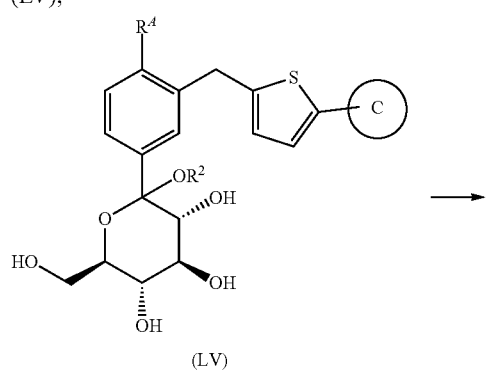

(LV)

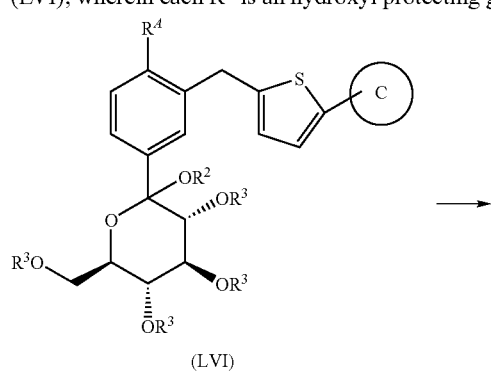

(LVI)

protecting the hydroxyl groups on the compound of formula (LV); to yield the corresponding compound of formula (LVI); wherein each $R^3$ is an hydroxyl protecting group;

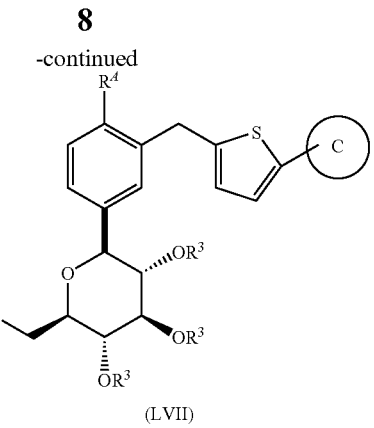

(LVII)

reducing the compound of formula (LVI); to yield the corresponding compound of formula (LVII);

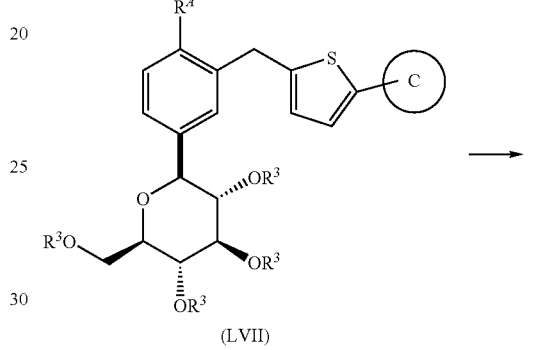

(LVII)

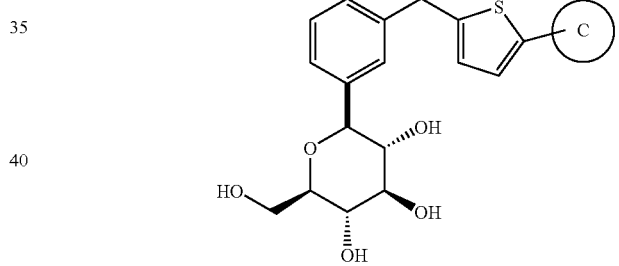

(IA')

removing the protecting groups on the hydroxyls of the compound of formula (LVII); to yield the corresponding compound of formula (IA').

In an embodiment, the present invention is directed to a process for the preparation of a compound of formula (I-S)

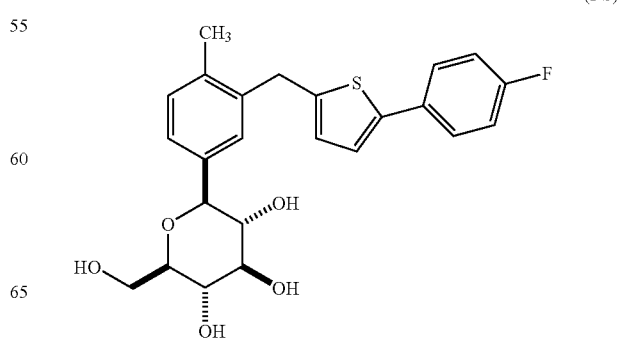

(I-S)

or solvate thereof; (also known as 1-(β-D-glucopyranosyl)-4-methyl-3-[5-(4-fluorophenyl)-2-thienylmethyl]benzene); comprising

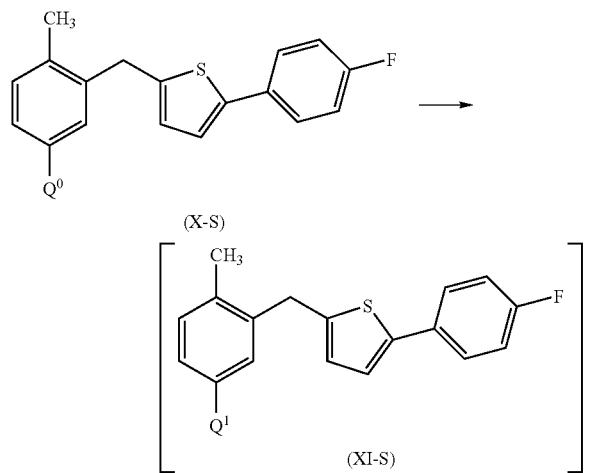

(X-S)

(XI-S)

reacting a compound of formula (X-S) wherein $Q^0$ is bromo or iodo, with a complex of di($C_{1-4}$alkyl)magnesium with lithium chloride or a complex of $C_{1-4}$alkyl magnesium chloride with lithium chloride or a complex of $C_{1-4}$alkyl magnesium bromide with lithium chloride; in an organic solvent or mixture thereof; at a temperature in the range of from about ambient temperature to about −78° C.; to yield the corresponding compound of formula (XI-S), wherein $Q^1$ is the corresponding MgCl or MgBr;

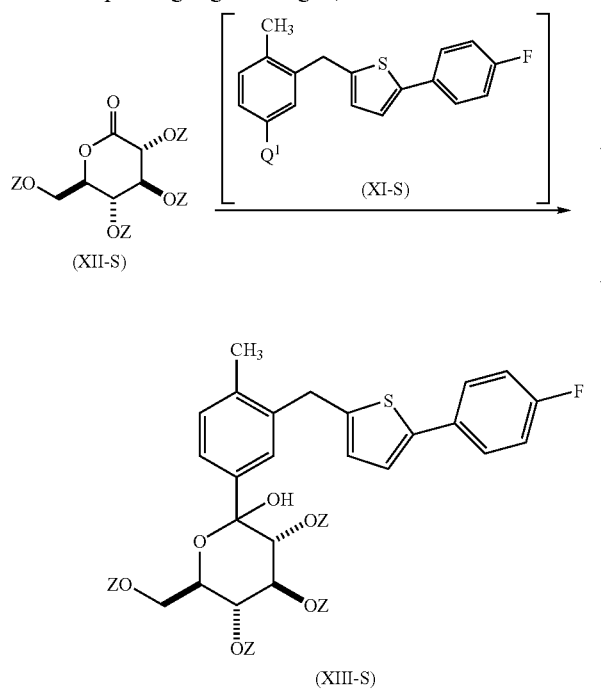

(XII-S)

(XI-S)

(XIII-S)

reacting the compound of formula (XI-S) with a compound of formula (XII-S), wherein Z is an oxygen protecting group; in an organic solvent or mixture thereof; at a temperature in the range of from about ambient temperature to about −78° C.; to yield the corresponding compound of formula (XIII-S);

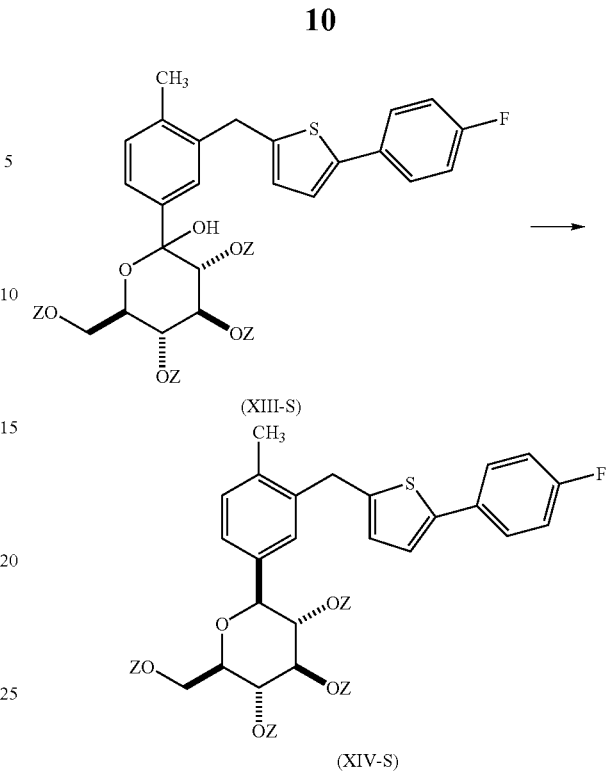

(XIII-S)

(XIV-S)

reacting the compound of formula (XIII-S) with a Lewis acid; in the presence of a silane reagent; in an organic solvent or mixture thereof; at a temperature in the range of from about 0° C. to about reflux; to yield the corresponding compound of formula (XIV-S);

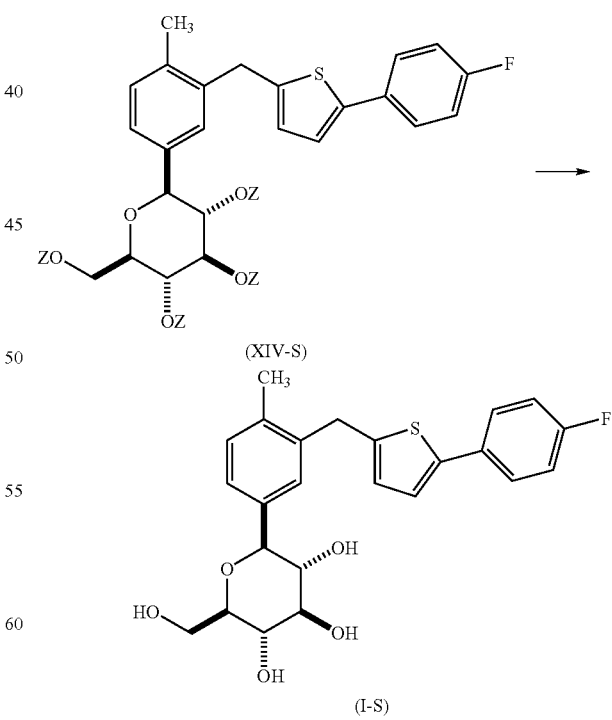

(XIV-S)

(I-S)

de-protecting the compound of formula (XIV-S); to yield the corresponding compound of formula (I-S).

In another embodiment, the present invention is directed to a process for the preparation of a compound of formula (I-K)

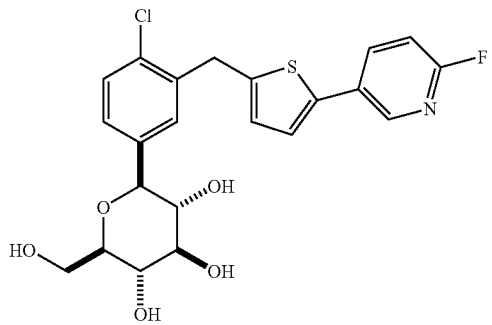

(I-K)

or pharmaceutically acceptable salt or solvate thereof; (also known as 1-(β-D-glucopyranosyl)-4-chloro-3-[5-(4-fluoro-3-pyridyl)-2-thienylmethyl]benzene); comprising

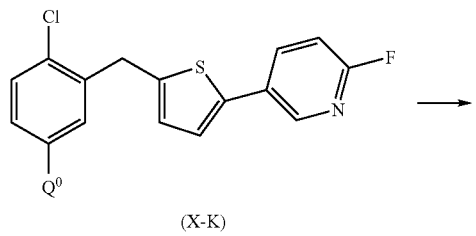

(X-K)

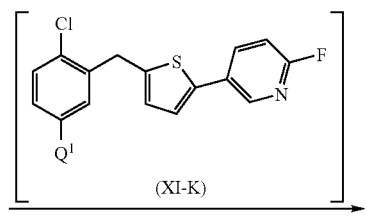

(XI-K)

reacting a compound of formula (X-K) wherein $Q^0$ is bromo or iodo with a complex of di($C_{1-4}$alkyl)magnesium with lithium chloride or a complex of $C_{1-4}$alkyl magnesium chloride with lithium chloride or a complex of $C_{1-4}$alkyl magnesium bromide with lithium chloride; in an organic solvent or mixture thereof; at a temperature in the range of from about ambient temperature to about −78° C.; to yield the corresponding compound of formula (XI-K), wherein $Q^1$ is the corresponding MgCl or MgBr;

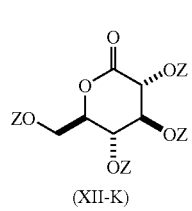

(XII-K)

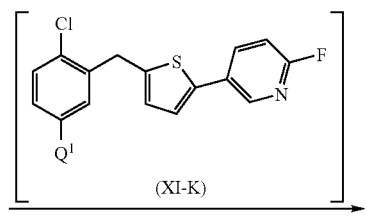

(XI-K)

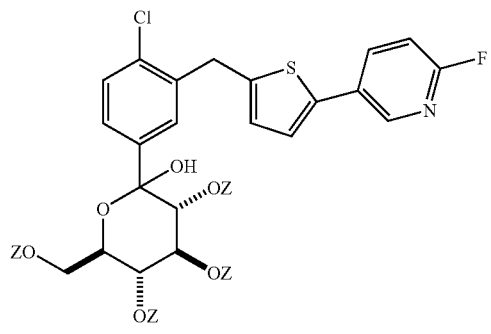

(XIII-K)

reacting the compound of formula (XI-K) with a compound of formula (XII-K), wherein Z is an oxygen protecting group; in an organic solvent or mixture thereof; at a temperature in the range of from about ambient temperature to about −78° C.; to yield the corresponding compound of formula (XII)-K);

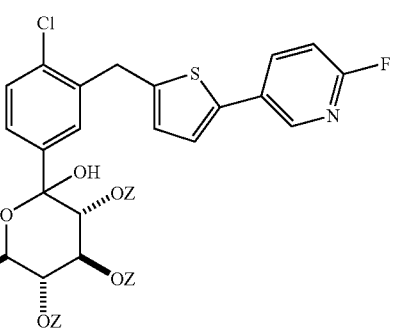

(XIII-K)

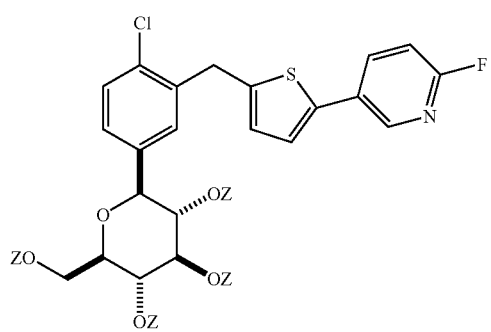

(XIV-K)

reacting the compound of formula (XIII-K) with a Lewis acid; in the presence of a silane reagent; in an organic solvent or mixture thereof; at a temperature in the range of from about 0° C. to about reflux; to yield the corresponding compound of formula (XIV-K);

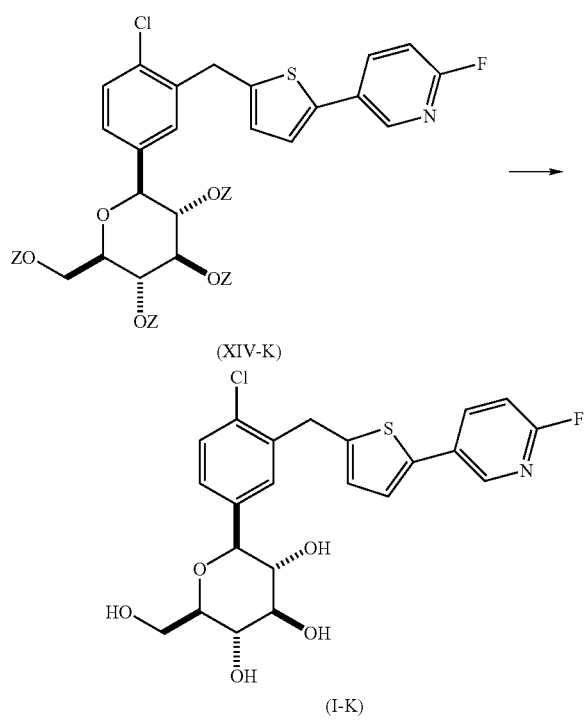

(XIV-K)

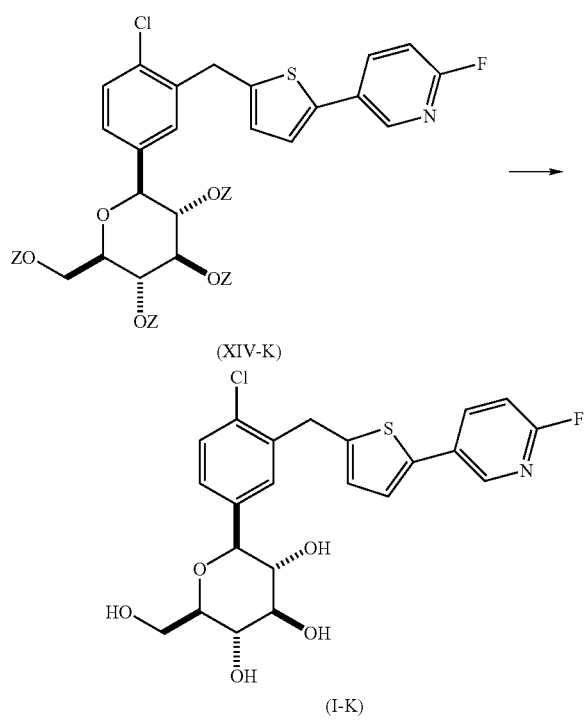

(I-K)

de-protecting the compound of formula (XIV-K); to yield the corresponding compound of formula (I-K).

The present invention is further directed to processes for the preparation of compounds of formula (X-S) and compounds of formula (X-K), as described in more detail in Scheme 4 and 5, which follow herein.

The present invention is further directed to a product prepared according to any of the processes described herein.

Illustrative of the invention is a pharmaceutical composition comprising a pharmaceutically acceptable carrier and the product prepared according to any of the processes described herein. An illustration of the invention is a pharmaceutical composition made by mixing the product prepared according to any of the processes described herein and a pharmaceutically acceptable carrier. Illustrating the invention is a process for making a pharmaceutical composition comprising mixing the product prepared according to any of the processes described herein and a pharmaceutically acceptable carrier.

Exemplifying the invention are methods of treating a disorder mediated by SGLT (including treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension) comprising administering to the subject in need thereof a therapeutically effective amount of any of the compounds or pharmaceutical compositions described above.

Further exemplifying the invention are methods of treating type 1 and type 2 diabetes mellitus, comprising administering to a subject in need of treatment a therapeutically effective amount of any of the compounds or pharmaceutical compositions described above, alone or in combination with at least one antidiabetic agent, agent for treating diabetic complications, anti-obesity agent, antihypertensive agent, antiplatelet agent, anti-atherosclerotic agent and/or hypolipidemic agent.

DETAILED DESCRIPTION OF THE INVENTION

The present invention is directed to a process for the preparation of compounds of formula (I)

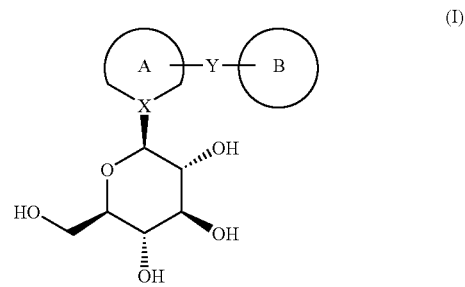

(I)

wherein X, Y, Ring A and Ring B are as herein defined; and pharmaceutically acceptable salts or solvates thereof; as described in more detail herein. The compounds of the formula (I) exhibits an inhibitory activity against sodium-dependent glucose transporter being present in the intestine and the kidney of mammalian species, and is useful in the treatment of diabetes mellitus or diabetic complications such as diabetic retinopathy, diabetic neuropathy, diabetic nephropathy, obesity, and delayed wound healing. In an embodiment, the present invention is directed to a process for the preparation of a compound of formula (I-S), as described in more detail herein. In another embodiment, the present invention is directed to a process for the preparation of a compound of formula (I-K), as described in more detail herein.

The present invention is further directed to a process for the preparation of compounds of formula (IA')

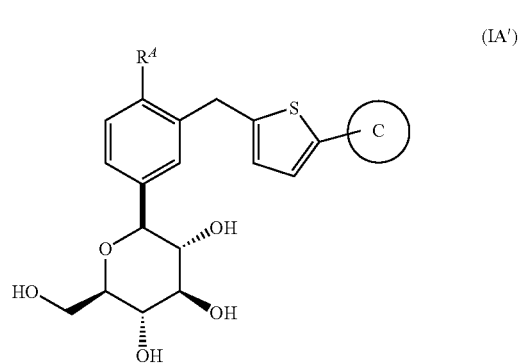

(IA')

wherein $R^4$ and Ring C are as herein defined; and pharmaceutically acceptable salts thereof. The compounds of formula (IA') are known to possess activity as inhibitors of sodium-dependent glucose transporters, and show excellent blood glucose lowering effect. The compounds of formula (IA') may therefore be useful for the treatment or prevention of diabetes mellitus, diabetic complications (e.g., diabetic retinopathy, diabetic neuropathy, and diabetic nephropathy), and related diseases such as obesity.

The present invention is further directed to processes for the preparation of compounds of formula (X-S) and compounds of formula (X-K), which compounds are intermediates useful in the synthesis of the compounds of formula (I), more particularly, in the synthesis of the compound of formula (I-S) and compound of formula (I-K).

The term "halogen", shall include chlorine, bromine, fluorine and iodine. When referring to substituents on the compound of formula (I), the term "halogen atom" or "halo" shall mean chlorine, bromine and fluorine, and chlorine and fluorine are preferable.

The term "alkyl group" means a straight or branched saturated monovalent hydrocarbon chain having 1 to 12 carbon atoms. The straight chain or branched chain alkyl group having 1 to 6 carbon atoms is preferable, and the straight chain or branched chain alkyl group having 1 to 4 carbon atoms is more preferable. Examples thereof are methyl group, ethyl group, propyl group, isopropyl group, butyl group, t-butyl group, isobutyl group, pentyl group, hexyl group, isohexyl group, heptyl group, 4,4-dimethylpentyl group, octyl group, 2,2,4-trimethylpentyl group, nonyl group, decyl group, and various branched chain isomers thereof. Further, the alkyl group may optionally and independently be substituted by 1 to 4 substituents as listed below, if necessary.

The term "lower alkyl" means a straight or branched saturated monovalent hydrocarbon chain having 1 to 6 carbon atoms. Preferably, "lower alkyl" means a straight or branched carbon chain having 1 to 4 carbon atoms. Most preferably, "lower alkyl" means a straight carbon chain having one or two carbon atoms. Examples of "lower alkyl" include methyl, ethyl, propyl, isopropyl, butyl, t-butyl, isobutyl, pentyl, hexyl and various branched chain isomers thereof.

The term "alkylene group" or "alkylene" means a straight or branched divalent saturated hydrocarbon chain having 1 to 12 carbon atoms. The straight chain or branched chain alkylene group having 1 to 6 carbon atoms is preferable, and the straight chain or branched chain alkylene group having 1 to 4 carbon atoms is more preferable. Examples thereof are methylene group, ethylene group, propylene group, trimethylene group, etc. If necessary, the alkylene group may optionally be substituted in the same manner as the above-mentioned "alkyl group". Where alkylene groups as defined above attach at two different carbon atoms of the benzene ring, they form an annelated five, six or seven membered carbocycle together with the carbon atoms to which they are attached, and may optionally be substituted by one or more substituents defined below.

The term "alkenyl group" means a straight or branched monovalent hydrocarbon chain having 2 to 12 carbon atoms and having at least one double bond. Preferable alkenyl group is a straight chain or branched chain alkenyl group having 2 to 6 carbon atoms, and the straight chain or branched chain alkenyl group having 2 to 4 carbon atoms is more preferable. Examples thereof are vinyl group, 2-propenyl group, 3-butenyl group, 2-butenyl group, 4-pentenyl group, 3-pentenyl group, 2-hexenyl group, 3-hexenyl group, 2-heptenyl group, 3-heptenyl group, 4-heptenyl group, 3-octenyl group, 3-nonenyl group, 4-decenyl group, 3-undecenyl group, 4-dodecenyl group, 4,8,12-tetradecatrienyl group, etc. The alkenyl group may optionally and independently be substituted by 1 to 4 substituents as mentioned below, if necessary.

The term "alkenylene group" means a straight or branched divalent hydrocarbon chain having 2 to 12 carbon atoms and having at least one double bond. The straight chain or branched chain alkenylene group having 2 to 6 carbon atoms is preferable, and the straight chain or branched chain alkenylene group having 2 to 4 carbon atoms is more preferable. Examples thereof are vinylene group, propenylene group, butadienylene group, etc. If necessary, the alkylene group may optionally be substituted by 1 to 4 substituents as mentioned below, if necessary. Where alkenylene groups as defined above attach at two different carbon atoms of the benzene ring, they form an annelated five, six or seven membered carbocycle (e.g., a fused benzene ring) together with the carbon atoms to which they are attached, and may optionally be substituted by one or more substituents defined below.

The term "alkynyl group" means a straight or branched monovalent hydrocarbon chain having at least one triple bond. The preferable alkynyl group is a straight chain or branched chain alkynyl group having 2 to 6 carbon atoms, and the straight chain or branched chain alkynyl group having 2 to 4 carbon atoms is more preferable. Examples thereof are 2-propynyl group, 3-butynyl group, 2-butynyl group, 4-pentynyl group, 3-pentynyl group, 2-hexynyl group, 3-hexynyl group, 2-heptynyl group, 3-heptynyl group, 4-heptynyl group, 3-octynyl group, 3-nonynyl group, 4-decynyl group, 3-undecynyl group, 4-dodecynyl group, etc. The alkynyl group may optionally and independently be substituted by 1 to 4 substituents as mentioned below, if necessary.

The term "cycloalkyl group" means a monocyclic or bicyclic monovalent saturated hydrocarbon ring having 3 to 12 carbon atoms, and the monocyclic saturated hydrocarbon group having 3 to 7 carbon atoms is more preferable. Examples thereof are a monocyclic alkyl group and a bicyclic alkyl group such as cyclopropyl group, cyclobutyl group, cyclopentyl group, cyclohexyl group, cycloheptyl group, cyclooctyl group, cyclodecyl group, etc. These groups may optionally and independently be substituted by 1 to 4 substituents as mentioned below, if necessary. The cycloalkyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the condensed unsaturated hydrocarbon ring may be optionally and independently be substituted by 1 to 4 substituents as mentioned below.

The term "cycloalkylidene group" means a monocyclic or bicyclic divalent saturated hydrocarbon ring having 3 to 12 carbon atoms, and the monocyclic saturated hydrocarbon group having 3 to 6 carbon atoms is preferable. Examples thereof are a monocyclic alkylidene group and a bicyclic alkylidene group such as cyclopropylidene group, cyclobutylidene group, cyclopentylidine group, cyclohexylidene group, etc. These groups may optionally and independently be substituted by 1 to 4 substituents as mentioned below, if necessary. Besides, the cycloalkylidene group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkenyl group" means a monocyclic or bicyclic monovalent unsaturated hydrocarbon ring having 4 to 12 carbon atoms and having at least one double bond. The preferable cycloalkenyl group is a monocyclic unsaturated hydrocarbon group having 4 to 7 carbon atoms. Examples thereof are monocyclic alkenyl groups such as cyclopentenyl group, cyclopentadienyl group, cyclohexenyl group, etc. These groups may optionally and independently be substituted by 1 to 4 substituents as mentioned below, if necessary. Besides, the cycloalkenyl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring and the unsaturated hydrocarbon ring may be optionally and independently be substituted by 1 to 4 substituents as mentioned below.

The term "cycloalkynyl group" means a monocyclic or bicyclic unsaturated hydrocarbon ring having 6 to 12 carbon atoms, and having at least one triple bond. The preferable cycloalkynyl group is a monocyclic unsaturated hydrocarbon group having 6 to 8 carbon atoms. Examples thereof are monocyclic alkynyl groups such as cyclooctynyl group, cyclodecynyl group. These groups may optionally be substituted by 1 to 4 substituents as mentioned below, if necessary. Besides, the cycloalkynyl group may optionally and independently be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "aryl group" means a monocyclic or bicyclic monovalent aromatic hydrocarbon group having 6 to 10 carbon atoms. Examples thereof are phenyl group, naphthyl group (including 1-naphthyl group and 2-naphthyl group). These groups may optionally and independently be substituted by 1 to 4 substituents as mentioned below, if necessary. Besides, the aryl group may optionally be condensed with a saturated hydrocarbon ring or an unsaturated hydrocarbon ring (said saturated hydrocarbon ring and unsaturated hydrocarbon ring may optionally contain an oxygen atom, a nitrogen atom, a sulfur atom, SO or $SO_2$ within the ring, if necessary), and the condensed saturated hydrocarbon ring or the unsaturated hydrocarbon ring may be optionally and independently be substituted by 1 to 4 substituents as mentioned below.

The term "unsaturated monocyclic heterocyclic ring" means an unsaturated hydrocarbon ring containing 1-4 heteroatoms independently selected from a nitrogen atom, an oxygen atom and a sulfur atom, and the preferable one is a 4-to 7-membered saturated or unsaturated hydrocarbon ring containing 1-4 heteroatoms independently selected from a nitrogen atom, an oxygen atom and a sulfur atom. Examples thereof are pyridine, pyrimidine, pyrazine, furan, thiophene, pyrrole, imidazole, pyrazole, oxazole, isoxazole, 4,5-dihydrooxazole, thiazole, isothiazole, thiadiazole, triazole, tetrazole, etc. Among them, pyridine, pyrimidine, pyrazine, furan, thiophene, pyrrole, imidazole, oxazole, and thiazole can be preferably used. The "unsaturated monocyclic heterocyclic ring" may optionally and independently be substituted by 1-4 substituents as mentioned below, if necessary.

The term "unsaturated fused heterobicyclic ring" means hydrocarbon ring comprised of a saturated or a unsaturated hydrocarbon ring condensed with the above mentioned unsaturated monocyclic heterocyclic ring where said saturated hydrocarbon ring and said unsaturated hydrocarbon ring may optionally contain an oxygen atom, a nitrogen atom, a sulfur atom, SO, or $SO_2$ within the ring, if necessary. The "unsaturated fused heterobicyclic ring" includes, for example, benzothiophene, indole, tetrahydrobenzothiophene, benzofuran, isoquinoline, thienothiophene, thienopyridine, quinoline, indoline, isoindoline, benzothiazole, benzoxazole, indazole, dihydroisoquinoline, etc. Further, the "heterocyclic ring" also includes possible N- or S-oxides thereof.

The term "heterocyclyl" means a monovalent group of the above-mentioned unsaturated monocyclic heterocyclic ring or unsaturated fused heterobicyclic ring and a monovalent group of the saturated version of the above-mentioned unsaturated monocyclic heterocyclic or unsaturated fused heterobicyclic ring. If necessary, the heterocyclyl may optionally and independently be substituted by 1 to 4 substituents as mentioned below.

In an embodiment of the present invention, in compounds of formula (IA'), the term "heterocyclyl" refers to a monovalent group of an unsaturated hydrocarbon ring containing 1-4 heteroatoms independently selected from a nitrogen atom, an oxygen atom and a sulfur atom, and the preferable one is a 4- to 7-membered saturated or unsaturated hydrocarbon ring containing 1-4 heteroatoms independently selected from a nitrogen atom, an oxygen atom and a sulfur atom. Examples of "heterocyclyl" include pyridyl, pyrimidyl, pyrazinyl, furyl, thienyl, pyrrolyl, imidazolyl, pyrazolyl, oxazolyl, isoxazolyl, 4,5-dihydrooxazolyl, thiazolyl, isothiazolyl, thiadiazolyl, triazolyl, and tetrazolyl. Preferable examples of "heterocyclyl" include pyridyl, pyrimidyl, pyrazinyl, furyl, thienyl, pyrrolyl, imidazolyl, oxazolyl, and thiazolyl.

The term "alkanoyl group" means a formyl group and ones formed by binding an "alkyl group" to a carbonyl group.

The term "alkoxy group" means ones formed by binding an "alkyl group" to an oxygen atom.

The term "lower alkoxy" refers to the above lower alkyl group linked to an oxygen atom. Preferably, "lower alkoxy" means a straight or branched alkyl-oxy group having 1 to 4 carbon atoms. Examples of "lower alkoxy" include methoxy, ethoxy, propoxy, isopropoxy, butoxy, t-butoxy, isobutoxy, pentyloxy, hexyloxy and various branched chain isomers thereof.

The substituent for the above each group includes, for example, a halogen atom (fluorine, chlorine, bromine), a nitro group, a cyano group, an oxo group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a hetero-cyclylcarbonyl group, an alkoxy-carbonyl group, an alkenyloxy-carbonyl group, an alkynyloxy-carbonyl group, a cycloalkyloxy-carbonyl group, a cycloalkenyloxy-carbonyl group, a cyclo-alkynyl-oxycarbonyl group, an aryloxycarbonyl group, a hetero-cyclyloxycarbonyl group, an alkanoyloxy group, an alkenyl-carbonyloxy group, an alkynyl-carbonyloxy group, a cycloalkyl-carbonyloxy group, a cycloalkenyl-carbonyloxy group, a cycloalkynyl-carbonyloxy group, an arylcarbonyloxy group, a hetero-cyclylcarbonyloxy group, an alkylthio group, an alkenyl-thio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxy-carbonyl-amino group, a mono- or di-arylcarbonyl-amino group, an alkylsulfinylamino group, an alkyl-sulfonyl-amino group, an arylsulfinylamino group, an arylsulfonylamino group, a carbamoyl group, a mono- or di-alkyl-carbamoyl group, a mono- or di-arylcarbamoyl group, an alkylsulfinyl group, an alkenyl-sulfinyl group, an alkynyl-sulfinyl group, a cycloalkyl-sulfinyl group, a cycloalkenylsulfinyl group, a cycloalkynyl-sulfinyl group, an arylsulfinyl group, a heterocyclyl-sulfinyl group, an alkyl-sulfonyl group, an alkenylsulfonyl group, an alkynylsulfonyl group, a cycloalkylsulfonyl group, a cycloalkenyl-sulfonyl group, a cycloalkynylsulfonyl group, an aryl-sulfonyl group, and a heterocyclylsulfonyl group. Each group as mentioned above may optionally be substituted by these substituents.

Further, the terms such as a haloalkyl group, a halo-lower alkyl group, a haloalkoxy group, a halo-lower alkoxy group, a halophenyl group, or a haloheterocyclyl group mean an alkyl group, a lower alkyl group, an alkoxy group, a lower alkoxy group, a phenyl group or a heterocyclyl group (hereinafter, referred to as an alkyl group, etc.) being substituted by one or more halogen atoms, respectively. Preferable ones are an alkyl group, etc. being substituted by 1 to 7 halogen atoms, and more preferable ones are an alkyl group, etc. being substituted by 1 to 5 halogen atoms. Similarly, the terms such as a hydroxyalkyl group, a hydroxy-lower alkyl group, a hydroxy-alkoxy group, a hydroxy-lower alkoxy group and a hydroxyphenyl group mean an alkyl group, etc., being substituted by one or more hydroxy groups. Preferable ones are an alkyl group, etc., being substituted by 1 to 4 hydroxy groups, and more preferable ones are an alkyl group, etc., being substituted by 1 to 2 hydroxy groups. Further, the terms such as an alkoxyalkyl group, a lower alkoxyalkyl group, an alkoxy-lower alkyl group, a lower alkoxy-lower alkyl group, an alkoxyalkoxy group, a lower alkoxyalkoxy group, an alkoxy-lower alkoxy group, a lower alkoxy-lower alkoxy group, an alkoxyphenyl group, and a lower alkoxyphenyl group means an alkyl group, etc., being substituted by one or more alkoxy groups. Preferable ones are an alkyl group, etc., being substituted by 1 to 4 alkoxy groups, and more preferable ones are an alkyl group, etc., being substituted by 1 to 2 alkoxy groups.

The terms "arylalkyl" and "arylalkoxy" as used alone or as part of another group refer to alkyl and alkoxy groups as described above having an aryl substituent.

The term "lower" used in the definitions for the formulae in the present specification means a straight or branched carbon chain having 1 to 6 carbon atoms, unless defined otherwise. More preferably, it means a straight or branched carbon chain having 1 to 4 carbon atoms.

The term "prodrug" means an ester or carbonate, which is formed by reacting one or more hydroxy groups of the compound of the formula I with an acylating agent substituted by an alkyl, an alkoxy or an aryl by a conventional method to produce acetate, pivalate, methylcarbonate, benzoate, etc. Further, the prodrug includes also an ester or amide, which is similarly formed by reacting one or more hydroxy groups of the compound of the formula I with an α-amino acid or a δ-amino acid, etc. using a condensing agent by a conventional method.

The pharmaceutically acceptable salt of the compound of the formula I includes, for example, a salt with an alkali metal such as lithium, sodium, potassium, etc.; a salt with an alkaline earth metal such as calcium, magnesium, etc.; a salt with zinc or aluminum; a salt with an organic base such as ammonium, choline, diethanolamine, lysine, ethylenediamine, t-butylamine, t-octylamine, tris(hydroxymethyl)aminomethane, N-methyl glucosamine, triethanolamine and dehydroabietylamine; a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

The compound of the present invention also includes a mixture of stereoisomers, or each pure or substantially pure isomer. For example, the present compound may optionally have one or more asymmetric centers at a carbon atom containing any one of substituents. Therefore, the compound of the formula I may exist in the form of enantiomer or diastereomer, or a mixture thereof. When the present compound (I) contains a double bond, the present compound may exist in the form of geometric isomerism (cis-compound, trans-compound), and when the present compound (I) contains an unsaturated bond such as carbonyl, then the present compound may exist in the form of a tautomer, and the present compound also includes these isomers or a mixture thereof. The starting compound in the form of a racemic mixture, enantiomer or diastereomer may be used in the processes for preparing the present compound. When the present compound is obtained in the form of a diastereomer or enantiomer, they can be separated by a conventional method such as chromatography or fractional crystallization.

In addition, the present compound (I) includes an intramolecular salt, hydrate, solvate or polymorph thereof.

Examples of the optionally substituted unsaturated monocyclic heterocyclic ring of the present invention include an unsaturated monocyclic heterocyclic ring which may optionally be substituted by 1-5 substituents selected from the group consisting of a halogen atom, a nitro group, a cyano group, an oxo group, a hydroxyl group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, and a heterocyclylsulfonyl group wherein each substituent may optionally be further substituted by these substituents.

Examples of the optionally substituted unsaturated fused heterobicyclic ring of the present invention include an unsaturated fused heterobicyclic ring which may optionally be substituted by 1-5 substituents selected from the group consisting of a halogen atom, a nitro group, a cyano group, an oxo group, a hydroxy group, a mercapto group, a carboxyl group, a sulfo group, an alkyl group, an alkenyl group, an alkynyl group, a cycloalkyl group, a cycloalkylidene-methyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenyl-carbonyl group, a cycloalkynyl-carbonyl group, an arylcarbonyl group, a heterocyclylcarbonyl group, an alkoxycarbonyl group, an alkenyloxycarbonyl group, an alkynyloxy-carbonyl group, a cycloalkyloxycarbonyl group, a cycloalkenyloxy-carbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cyclo-alkylcarbonyloxy group, a cycloalkenylcarbonyloxy group, a cyclo-alkynylcarbonyloxy group, an arylcarbonyloxy group, a heterocyclyl-carbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoyl-amino group, a mono- or di-alkoxycarbonylamino group, a mono- or di-arylcarbonylamino group, an alkylsulfinylamino group, an alkyl-sulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cyclo-alkenylsulfinyl group, a cycloalkynyl-sulfinyl group, an arylsulfinyl group, a heterocyclylsulfinyl group, an alkylsulfonyl group, an alkenylsulfonyl group, an alkynylsulfonyl group, a cycloalkylsulfonyl group, a cyclo-alkenylsulfonyl group, a cycloalkynylsulfonyl group, an arylsulfonyl group, and a heterocyclylsulfonyl group, wherein each substituent may optionally be further substituted by these substituents.

Examples of the optionally substituted benzene ring of the present invention include a benzene ring which may optionally be substituted by 1-5 substituents selected from the group consisting of a halogen atom, a nitro group, a cyano group, a hydroxy group, a mercapto group, a carboxyl group, a sulfo group, an alkyl group, an alkenyl group, an alkynyl group, a cycloalkyl group, a cycloalkylidenemethyl group, a cycloalkenyl group, a cycloalkynyl group, an aryl group, a heterocyclyl group, an alkoxy group, an alkenyloxy group, an alkynyloxy group, a cycloalkyloxy group, a cycloalkenyloxy group, a cycloalkynyloxy group, an aryloxy group, a heterocyclyloxy group, an alkanoyl group, an alkenylcarbonyl group, an alkynylcarbonyl group, a cycloalkylcarbonyl group, a cycloalkenylcarbonyl group, a cycloalkynylcarbonyl group, an arylcarbonyl group, a heterocyclylcarbonyl group, an alkoxycarbonyl group, an alkenyloxycarbonyl group, an alkynyloxycarbonyl group, a cycloalkyloxycarbonyl group, a cycloalkenyloxycarbonyl group, a cycloalkynyloxycarbonyl group, an aryloxycarbonyl group, a heterocyclyloxycarbonyl group, an alkanoyloxy group, an alkenylcarbonyloxy group, an alkynylcarbonyloxy group, a cycloalkylcarbonyloxy group, a cycloalkenylcarbonyloxy group, a cycloalkynylcarbonyloxy group, an arylcarbonyloxy group, a heterocyclylcarbonyloxy group, an alkylthio group, an alkenylthio group, an alkynylthio group, a cycloalkylthio group, a cycloalkenylthio group, a cycloalkynylthio group, an arylthio group, a heterocyclylthio group, an amino group, a mono- or di-alkylamino group, a mono- or di-alkanoylamino group, a mono- or di-alkoxycarbonylamino group, a mono- or di-arylcarbonylamino group, an alkylsulfinylamino group, an alkylsulfonylamino group, an arylsulfinylamino group, an arylsulfonylamino group, a carbamoyl group, a mono- or di-alkylcarbamoyl group, a mono- or di-arylcarbamoyl group, an alkylsulfinyl group, an alkenylsulfinyl group, an alkynylsulfinyl group, a cycloalkylsulfinyl group, a cycloalkenylsulfinyl group, a cycloalkynylsulfinyl group, an arylsulfinyl group, a heterocyclylsulfinyl group, an alkylsulfonyl group, an alkenylsulfonyl group, an alkynylsulfonyl group, a cycloalkylsulfonyl group, a cycloalkenylsulfonyl group, a cycloalkynylsulfonyl group, an arylsulfonyl group, a heterocyclylsulfonyl group, an alkylene group, an alkyleneoxy group, an alkylenedioxy group, and an alkenylene group wherein each substituent may optionally be further substituted by these substituents.

Moreover, examples of the optionally substituted benzene ring include a benzene ring substituted with an alkylene group to form an annelated carbocycle together with the carbon atoms to which they are attached, and also includes a benzene ring substituted with an alkenylene group to form an annelated carbocycle such as a fused benzene ring together with the carbon atoms to which they are attached.

Preferable examples of the optionally substituted unsaturated monocyclic heterocyclic ring include an unsaturated monocyclic heterocyclic ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted unsaturated fused heterobicyclic ring include an unsaturated fused heterobicyclic ring which may optionally be substituted by 1-3 substituents independently selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, and an oxo group.

Preferable examples of the optionally substituted benzene ring include a benzene ring which may optionally be substituted by 1-3 substituents selected from the group consisting of a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryl group, an aryloxy group, an arylalkoxy group, a cyano group, a nitro group, an amino group, a mono- or di-alkylamino group, an alkanoylamino group, an alkoxycarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, an arylsulfonyl group, a heterocyclyl group, an alkylene group, an alkyleneoxy group, an alkylenedioxy group, and an alkenylene group.

In another preferable embodiment of the present invention, the optionally substituted unsaturated monocyclic heterocyclic ring is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group;

the optionally substituted unsaturated fused heterobicyclic ring is an unsaturated fused heterobicyclic ring which may optionally be substituted by 1-3 substituents selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkylthio group, an alkylsulfonyl group, an alkylsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkanoyl group, an alkylsulfonylamino group, a phenyl group, a phenoxy group, a phenylsulfonylamino group, phenylsulfonyl group, a heterocyclyl group, and an oxo group; and the optionally substituted benzene ring is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, an alkoxycarbonylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a hydroxy group, a cyano group, an alkyl group, a haloalkyl group, an alkoxy group, a haloalkoxy group, an alkanoyl group, an alkylthio group, an alkylsulfonyl group, a mono- or di-alkylamino group, a carboxyl group, an alkoxycarbonyl group, a phenyl group, an alkyleneoxy group, an alkylenedioxy group, an oxo group, a carbamoyl group, and a mono- or di-alkylcarbamoyl group.

In a preferable embodiment, the optionally substituted unsaturated monocyclic heterocyclic ring is an unsaturated monocyclic heterocyclic ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, and an oxo group;

the optionally substituted unsaturated fused heterobicyclic ring is an unsaturated fused heterobicyclic ring which may optionally be substituted by 1-3 substituents independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxy group, an alkoxycarbonyl group, a carbamoyl group, a mono- or di-alkylcarbamoyl group, a phenyl group, a heterocyclyl group, and an oxo group; and the optionally substituted benzene ring is a benzene ring which may optionally be substituted by 1-3 substituents, independently selected from the group consisting of a halogen atom, a cyano group, an alkyl group, an alkoxy group, an alkanoyl group, a mono- or di-alkylamino group, an alkanoylamino group, an alkoxycarbonylamino group, a carboxyl group, an alkoxycarbonyl group, a carbamoyl group, a mono- or di-alkylcarbamoyl group, a phenyl group, a heterocyclyl group, an alkylene group, and an alkenylene group;

wherein each of the above-mentioned substituents on the unsaturated monocyclic heterocyclic ring, the unsaturated fused heterobicyclic ring and the benzene ring may further be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In another preferable embodiment, (1) Ring A is an unsaturated monocyclic heterocyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alkylsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group;

(2) Ring A is a benzene ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, an alkanoylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group, and an alkenylene group, and Ring B is an unsaturated monocyclic heterocyclic ring or an unsaturated fused heterobicyclic ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group; or (3) Ring A is an unsaturated fused heterobicyclic ring which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, and an oxo group, and Ring B is an unsaturated monocyclic heterocyclic ring, an unsaturated fused heterobicyclic ring, or a benzene ring, each of which may optionally be substituted by 1-3 substituents, independently selected from the group consisting of a halogen atom, a hydroxy group, a cyano group, a nitro group, an alkyl group, an alkenyl group, an alkynyl group, a cycloalkyl group, a cycloalkylidenemethyl group, an alkoxy group, an alkanoyl group, an alkylthio group, an alkylsulfonyl group, an alklsulfinyl group, an amino group, a mono- or di-alkylamino group, a sulfamoyl group, a mono- or di-alkylsulfamoyl group, a carboxyl group, an alkoxycarbonyl group, a carbamoyl group, a mono- or di-alkylcarbamoyl group, an alkylsulfonylamino group, a phenyl group, a phenoxy group, a phenylsulfonylamino group, a phenylsulfonyl group, a heterocyclyl group, an alkylene group and an oxo group;

wherein each of the above-mentioned substituents on Ring A and Ring B may optionally be substituted by 1-3 substituents, independently selected from the group consisting of a halogen atom, a cyano group, an alkyl group, a haloalkyl group, an alkoxy group, a haloalkoxy group, an alkanoyl group, a mono- or di-alkylamino group, a carboxyl group, a hydroxy group, a phenyl group, an alkylenedioxy group, an alkyleneoxy group, an alkoxycarbonyl group, a carbamoyl group and a mono- or di-alkylcarbamoyl group.

In a more preferable embodiment of the present invention, Ring A and Ring B are (1) Ring A is an unsaturated monocyclic heterocyclic ring which may optionally be substituted by a halogen atom, a lower alkyl group, a halo-lower alkyl group, a lower alkoxy group, or an oxo group, and Ring B is (a) a benzene ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; (b) an unsaturated monocyclic heterocyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mono- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group;

(2) Ring A is a benzene ring which may optionally be substituted by a halogen atom, a lower alkyl group, a halo-lower alkyl group, a lower alkoxy group, a phenyl group, or a lower alkenylene group, and Ring B is (a) an unsaturated monocyclic heterocyclic ring which may optionally be substituted by a halogen atom; a cyano group; a lower alkyl group; a halo-lower alkyl group; a phenyl-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, a mono- or di-lower alkylamino group, or a carbamoyl group; or a heterocyclyl group optionally substituted by a halogen atom, a cyano group, a lower alkyl group, a halo-lower alkyl group, a lower alkoxy group, a mono- or di-lower alkylamino group or a carbamoyl group; (b) an unsaturated fused heterobicyclic ring which may optionally be substituted by a group selected from a halogen atom, cyano group, a lower alkyl group, a halo-lower alkyl group, a phenyl-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; or (3) Ring A is an unsaturated fused heterobicyclic ring which may optionally be substituted by a halogen atom, a lower alkyl group, a halo-lower alkyl group, a lower alkoxy group, or an oxo group, and Ring B is (a) a benzene ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group; (b) an unsaturated monocyclic heterocyclic ring which may optionally be substituted by a halogen atom; a cyano group; a lower alkyl group; a halo-lower alkyl group; a lower alkoxy group; a halo-lower alkoxy group; a mono- or di-lower alkylamino group; a phenyl group optionally substituted by a halogen atom, a cyano group, a lower alkyl group, a halo-lower alkyl group, a lower alkoxy group, or a mono- or di-lower alkylamino group; or a heterocyclyl group optionally substituted by a halogen atom, a cyano group, a lower alkyl group, a halo-lower alkyl group, a lower alkoxy group, or a mono- or di-lower alkylamino group; or (c) an unsaturated fused heterobicyclic ring which may optionally be substituted by a group selected from a halogen atom, cyano group, a lower alkyl group, a halo-lower alkyl group, a lower alkoxy group, a halo-lower alkoxy group, a mo- or di-lower alkylamino group, a phenyl group which may be substituted with a halogen atom, cyano group, a lower alkyl group, a halo-lower alkyl group, a lower alkoxy group, or a mono- or di-lower alkylamino group; and a heterocyclyl group which may optionally be substituted with a group selected from a halogen atom, cyano group, a lower alkyl group, a halo-lower alkyl group, a lower alkoxy group, or a mono- or di-lower alkylamino group.

In another more preferable embodiment, Y is —CH$_2$— and is linked at the 3-position of Ring A, with respect to X being the 1-position, Ring A is a benzene ring which is substituted by 1-3 substituents selected from the group consisting of a lower alkyl group, a halo-lower alkyl group, a halogen atom, a lower alkoxy group, a phenyl group, and a lower alkenylene group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a phenyl-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxy phenyl group, a lower alkylenedioxyphenyl group, a lower alkyleneoxy phenyl group, a mono- or di-lower alkylaminophenyl group, a carbamoyl phenyl group, a mono- or di-lower alkylcarbamoylphenyl group, a heterocyclyl group, a haloheterocyclyl group, a cyanoheterocyclyl group, a lower alkylheterocyclyl group, a lower alkoxyheterocyclyl group, a mono- or di-lower alkylaminoheterocyclyl group, a carbamoylheterocyclyl group, and a mono- or di-lower alkylcarbamoyl group.

In another more preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is a benzene ring which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a heterocyclyl group, a haloheterocyclyl group, a cyanoheterocyclyl group, a lower alkylheterocyclyl group, and a lower alkoxyheterocyclyl group.

Further, in another preferable embodiment, Y is —CH$_2$— and is linked at the 3-position of Ring A, with respect to X being the 1-position, Ring A is an unsaturated monocyclic heterocyclic ring which may be substituted by 1-3 substituents selected from the group consisting of a lower alkyl group, a halogen atom, a lower alkoxy group, and an oxo group, and Ring B is an unsaturated monocyclic heterocyclic ring or an unsaturated fused heterobicyclic ring, each of which may be substituted by 1-3 substituents selected from the group consisting of a lower alkyl group, a halo-lower alkyl group, a halogen atom, a lower alkoxy group, a halo-lower alkoxy group, a phenyl group, a halophenyl group, a cyanophenyl group, a lower alkylphenyl group, a halo-lower alkylphenyl group, a lower alkoxyphenyl group, a halo-lower alkoxyphenyl group, a heterocyclyl group, a haloheterocyclyl group, a cyanoheterocyclyl group, a lower alkylheterocyclyl group, and a lower alkoxyheterocyclyl group.

In a more preferable embodiment of the present invention, X is a carbon atom and Y is —CH$_2$—.

Further, in another preferable embodiment, Ring A and Ring B are:

(1) Ring A is a benzene ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, a phenyl group, and a lower alkenylene group, and Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group, a halo-lower alkoxy group, or a carbamoyl group; a heterocyclyl group optionally substituted by a halogen atom, a cyano group, a lower alkyl group, a halo-lower alkyl group, a lower alkoxy group, a halo-lower alkoxy group or a carbamoyl group; and an oxo group, (2) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, and Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; a lower alkylene group, (3) Ring A is an unsaturated monocyclic heterocyclic ring which may optionally be substituted by 1-3 substituents, independently selected from the group consisting of a halogen atom, a lower alkyl group optionally substituted by a halogen atom or a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group;

(4) Ring A is an unsaturated fused heterobicyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is a benzene ring which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and a lower alkylene group, or (5) Ring A is an unsaturated monocyclic heterocyclic ring which may optionally be substituted by 1-3 substituents, independently selected from the group consisting of a halogen atom, a lower alkyl group optionally substituted by a lower alkoxy group, a lower alkoxy group optionally substituted by a halogen atom or a lower alkoxy group, a cycloalkyl group, a cycloalkoxy group, and an oxo group, Ring B is an unsaturated monocyclic heterocyclic ring or an unsaturated fused heterobicyclic ring, each of which may optionally be substituted by 1-3 substituents, independently selected from the group consisting of a halogen atom; a lower alkyl group optionally substituted by a halogen atom, a lower alkoxy group or a phenyl group; a lower alkoxy group optionally substituted by a halogen atom or a lower alkoxy group; a cycloalkyl group; a cycloalkoxy group; a phenyl group optionally substituted by a halogen atom, a cyano group, a lower alkyl group, a halo-lower alkyl group, a lower alkoxy group or a halo-lower alkoxy group; a heterocyclyl group optionally substituted by a halogen atom, a cyano group, a lower alkyl group, a halo-lower alkyl group, a lower alkoxy group or a halo-lower alkoxy group; and an oxo group.

In another preferable embodiment of the present invention, Y is linked at the 3-position of Ring A, with respect to X being the 1-position, Ring A is a benzene ring which may optionally be substituted by a halogen atom, a lower alkyl group optionally substituted by a halogen atom, a lower alkoxy group, or a phenyl group, and Ring B is an unsaturated monocyclic heterocyclic ring or an unsaturated fused heterobicyclic ring which may optionally be substituted by 1-3 substituents, independently selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and an oxo group.

In another more preferable embodiment of the present invention, Y is linked at the 3-position of Ring A, with respect to X being the 1-position, Ring A is an unsaturated monocyclic heterocyclic ring which may optionally be substituted by a substituent selected from a halogen atom, a lower alkyl group, and an oxo group, and Ring B is a benzene ring which may optionally be substituted by a substituent selected from the group consisting of a halogen atom; a lower alkyl group optionally substituted by a halogen atom or a phenyl group; a lower alkoxy group; a phenyl group optionally substituted by a halogen atom, a cyano group, a lower alkyl group, a halo-lower alkyl group, or a lower alkoxy group; a heterocyclyl group optionally substituted by a halogen atom, a cyano group, a lower alkyl group, a halo-lower alkyl group, or a lower alkoxy group; and a lower alkylene group.

Preferable examples of unsaturated monocyclic heterocyclic ring include a 5- or 6-membered unsaturated heterocyclic ring containing 1 or 2 hetero atoms independently selected from a nitrogen atom, an oxygen atom, and a sulfur atom. More specifically, preferred are furan, thiophene, oxazole, isoxazole, triazole, tetrazole, pyrazole, pyridine, pyrimidine, pyrazine, dihydroisoxazole, dihydropyridine, and thiazole. Preferable unsaturated fused heterobicyclic ring includes a 9- or 10-membered unsaturated fused heterobicyclic ring containing 1 to 4 hetero atoms independently selected from a nitrogen atom, an oxygen atom, and a sulfur atom. More specifically, preferred are indoline, isoindoline, benzothiazole, benzoxazole, indole, indazole, quinoline, isoquinoline, benzothiophene, benzofuran, thienothiophene, and dihydroisoquinoline.

In a more preferred embodiment of the present invention, Ring A is a benzene ring which may optionally be substituted by a substituent selected from the group consisting of a halogen atom, a lower alkyl group, a halo-lower alkyl group, a lower alkoxy group, and a phenyl group, and Ring B is a heterocyclic ring selected from the group consisting of thiophene, furan, benzofuran, benzothiophene, and benzothiazole, wherein the heterocyclic ring may optionally be substituted by a substituent selected from the following group: a halogen atom, a cyano group, a lower alkyl group, a halo-lower alkyl group, a phenyl-lower alkyl group, a lower alkoxy group, a halo-lower alkoxy group, a phenyl group, a halophenyl group, a lower alkylphenyl group, a lower alkoxyphenyl group, a thienyl group, a halothienyl group, a pyridyl group, a halopyridyl group, and a thiazolyl group.

In yet another preferred embodiment, Y is —CH$_2$—, Ring A is an unsaturated monocyclic heterocyclic ring or an unsaturated fused heterobicyclic ring selected from the group consisting of thiophene, dihydroisoquinoline, dihydroisoxazole, triazole, pyrazole, dihydropyridine, dihydroindole, indole, indazole, pyridine, pyrimidine, pyrazine, quinoline, and a isoindoline, wherein the heterocyclic ring may optionally substituted by a substituent selected from the following group: a halogen atom, a lower alkyl group, and an oxo group, and Ring B is a benzene ring which may optionally be substituted by a substituent selected from the following group: a halogen atom, a lower alkyl group, a halo-lower alkyl group, a lower alkoxy group, and a halo-lower alkoxy group.

In a further preferred embodiment of the present invention, Ring A is a benzene ring which is substituted by a halogen atom or a lower alkyl group, and Ring B is thienyl group which is substituted by phenyl group or a heterocyclyl group in which said phenyl group and heterocyclyl group is substituted by 1-3 substituents selected from a halogen atom, a cyano group, a lower alkyl group, a halo-lower alkyl group, a lower alkoxy group, and a halo-lower alkoxy group.

Further, in another aspect of the present invention, preferable examples of the compound of the formula I include a compound wherein Ring A is

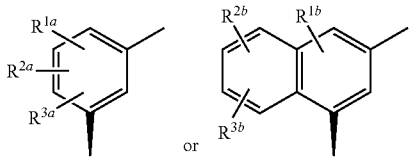

wherein $R^{1a}$, $R^{2a}$, $R^{3a}$, $R^{1b}$, $R^{2b}$ and $R^{3b}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, a phenyl group, a phenylalkoxy group, a cyano group, a nitro group, an amino group, a mono- or di-alkylamino group, an alkanoylamino group, a carboxyl group, an alkoxycarbonyl group, a carbamoyl group, a mono- or di-alkylcarbamoyl group, an alkanoyl group, an alkylsulfonylamino group, a phenylsulfonylamino group, an alkylsulfinyl group, an alkylsulfonyl group, or a phenylsulfonyl group, and Ring B is

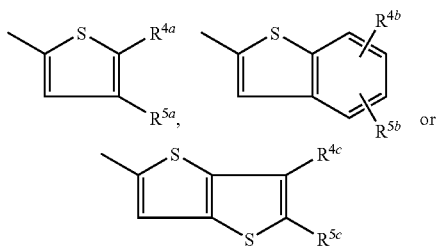

wherein $R^{4a}$ and $R^{5a}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonyl-amino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, an alkylenedioxy group, an alkyleneoxy group, a mono- or di-alkylamino group, a carbamoyl group, or a mono- or di-alkylcarbamoyl group; or a heterocyclyl group optionally substituted by a halogen atom, a cyano group, an alkyl group, a haloalkyl group, an alkoxy group, a haloalkoxy group, a carbamoyl group, or a mono- or di-alkylcarbamoyl group, or $R^{4a}$ and $R^{5a}$ are bonded to each other at the terminals thereof to form an alkylene group; and $R^{4b}$, $R^{5b}$, $R^{4c}$ and $R^{5c}$ are each independently a hydrogen atom; a halogen atom; a hydroxy group; an alkoxy group; an alkyl group; a haloalkyl group; a haloalkoxy group; a hydroxyalkyl group; an alkoxyalkyl group; a phenylalkyl group; an alkoxyalkoxy group; a hydroxyalkoxy group; an alkenyl group; an alkynyl group; a cycloalkyl group; a cycloalkylidenemethyl group; a cycloalkenyl group; a cycloalkyloxy group; a phenyloxy group; a phenylalkoxy group; a cyano group; a nitro group; an amino group; a mono- or di-alkylamino group; an alkanoylamino group; a carboxyl group; an alkoxycarbonyl group; a carbamoyl group; a mono- or di-alkylcarbamoyl group; an alkanoyl group; an alkylsulfonylamino group; a phenylsulfonyl-amino group; an alkylsulfinyl group; an alkylsulfonyl group; a phenylsulfonyl group; a phenyl group optionally substituted by a halogen atom, a cyano group, an alkyl group, a haloalkyl group, an alkoxy group, a haloalkoxy group, a methylenedioxy group, an ethyleneoxy group, or a mono- or di-alkylamino group; or a heterocyclyl group optionally substituted by a halogen atom, a cyano group, an alkyl group, a haloalkyl group, an alkoxy group or a haloalkoxy group.

More preferred is a compound wherein $R^{1a}$, $R^{2a}$, $R^{3a}$, $R^{1b}$, $R^{2b}$, and $R^{3b}$ are each independently a hydrogen atom, a halogen atom, a lower alkyl group, a halo-lower alkyl group, a lower alkoxy group, or a phenyl group;

$R^{4a}$ and $R^{5a}$ are each independently a hydrogen atom; a halogen atom; a lower alkyl group; a halo-lower alkyl group; a phenyl-lower alkyl group; a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, or $R^{4a}$ and $R^{5a}$ are bonded to each other at the terminals thereof to form a lower alkylene group; and $R^{4b}$, $R^{5b}$, $R^{4c}$ and $R^{5c}$ are each independently a hydrogen atom, a halogen atom, a lower alkyl group, a halo-lower alkyl group, a lower alkoxy group, or a halo-lower alkoxy group.

Further preferred is a compound in which Ring B is

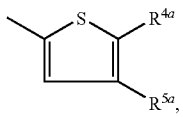

wherein $R^{4a}$ is a phenyl group optionally substituted by a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, or a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, or $R^{4a}$ and $R^{5a}$ are bonded to each other at the terminals thereof to form a lower alkylene group.

Further more preferred is a compound in which Ring A is

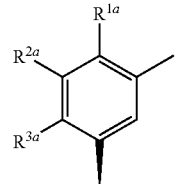

wherein $R^{1a}$ is a halogen atom, a lower alkyl group, or a lower alkoxy group, and $R^{2a}$ and $R^{3a}$ are hydrogen atoms; and Ring B is

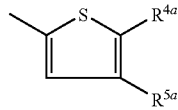

wherein $R^{4a}$ is a phenyl group optionally substituted by a substituent selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; or a heterocyclyl group optionally substituted by a halogen atom, a cyano group, a lower alkyl group, a lower alkoxy group, a carbamoyl group, or a mono- or di-lower alkylcarbamoyl group, and $R^{5a}$ is a hydrogen atom, and Y is —$CH_2$—.

In more preferable embodiment, $R^{4a}$ is a phenyl group optionally substituted by a halogen atom, a cyano group, a lower alkyl group, a halo-lower alkyl group, a lower alkoxy group, or a halo-lower alkoxy group; or a heterocyclyl group optionally substituted by a halogen atom, a cyano group, a lower alkyl group, or a lower alkoxy group.

In another preferable embodiment of the present invention, a preferable compound can be represented by the following formula IA:

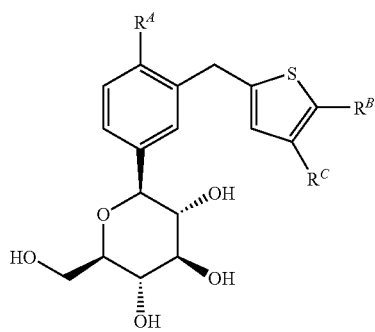

wherein $R^A$ is a halogen atom, a lower alkyl group or a lower alkoxy group; $R^B$ is a phenyl group optionally substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group optionally substituted by 1-3 substituents selected from a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group; and $R^C$ is hydrogen atom; or $R^B$ and $R^C$ taken together are a fused benzene ring which may be substituted by a halogen atom, a lower alkyl group, a halo-lower alkyl group, a lower alkoxy group or a halo-lower alkoxy group.

In a preferable embodiment, $R^A$ is a halogen atom or a lower alkyl group, $R^C$ is hydrogen atom, and $R^B$ is phenyl group substituted by 1-3 substituents selected from a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group. The chemical structure of such compounds are represented by the following formula (IA'):

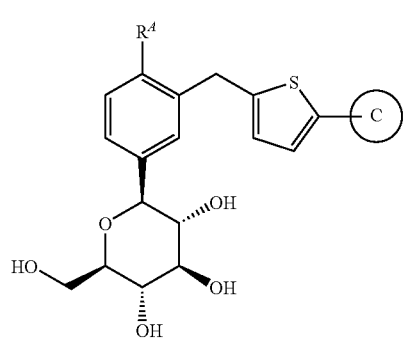

wherein $R^A$ is a halogen atom, or a lower alkyl group, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, a methylenedioxy group, an ethyleneoxy group, a mono- or di-lower alkylamino group, a carbamoyl group, and a mono- or di-lower alkylcarbamoyl group; or a heterocyclyl group substituted by 1-3 substituents selected from the group consisting of a halogen atom, a cyano group, a lower alkyl group, a halo-lower alkyl group, a lower alkoxy group, a halo-lower alkoxy group, a mono- or di-lower alkylamino group, a carbamoyl group, and a mono- or di-lower alkylcarbamoyl group.

In a more preferable embodiment, Ring C is a phenyl group substituted by 1-3 substituents selected from the group consisting of a halogen atom, a cyano group, a lower alkyl group, a halo-lower alkyl group, a lower alkoxy group, a halo-lower alkoxy group, and a mono- or di-lower alkylamino group; or a heterocyclyl group substituted by a substituent selected from the group consisting of a halogen atom, a cyano group, a lower alkyl group, a halo-lower alkyl group, a lower alkoxy group, and a halo-lower alkoxy group.

Among them, a compound in which Ring C is a phenyl group substituted by a halogen atom, a cyano group, a lower alkyl group, a halo-lower alkyl group, a lower alkoxy group or a halo-lower alkoxy group; or a heterocyclyl group substituted by a halogen atom, a cyano group, a lower alkyl group, or a lower alkoxy group is preferred.

A preferred heterocyclyl group includes a 5- or 6-membered heterocyclyl group containing 1 or 2 hetero atoms independently selected from the group consisting of a nitrogen atom, an oxygen atom, and a sulfur atom, or a 9- or 10-membered heterocyclyl group containing 1 to 4 hetero atoms independently selected from the group consisting of a nitrogen atom, an oxygen atom, and a sulfur atom. Specifically, a thienyl group, a pyridyl group, a pyrimidyl group, a pyrazinyl group, pyrazolyl group, a thiazolyl group, a quinolyl group, a tetrazolyl group and an oxazolyl group are preferred.

In a further preferable embodiment, Ring C is a phenyl group substituted by a halogen atom or a cyano group, or a pyridyl group substituted by a halogen atom.

In another preferable embodiment of the present invention, preferred is a compound in which Ring A is

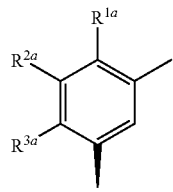

wherein $R^{1a}$ is a halogen atom, a lower alkyl group, or a lower alkoxy group, and $R^{2a}$ and $R^{3a}$ are hydrogen atoms; and Ring B is

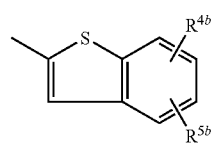

wherein $R^{4b}$ and $R^{5b}$ are each independently a hydrogen atom, a halogen atom, a lower alkyl group, a halo-lower alkyl group, a lower alkoxy group, or a halo-lower alkoxy group.

In another aspect of the present invention, preferable examples of the compound I include a compound represented by the following formula IB:

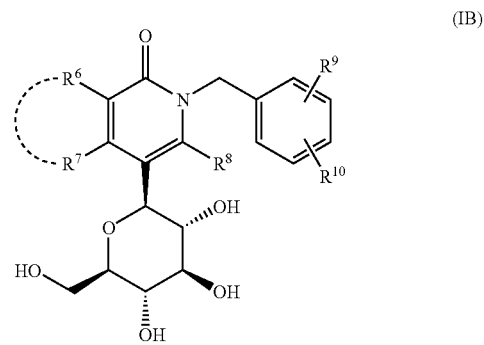

(IB)

wherein $R^8$, $R^9$ and $R^{10}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group; and a group represented by:

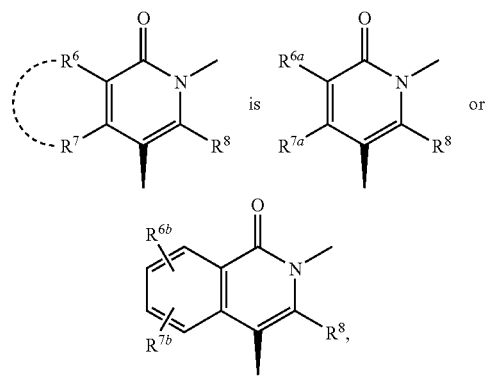

wherein $R^{6a}$ and $R^{7a}$ are each independently a hydrogen atom, a halogen atom, a hydroxy group, an alkoxy group, an alkyl group, a haloalkyl group, a haloalkoxy group, a hydroxyalkyl group, an alkoxyalkyl group, an alkoxyalkoxy group, an alkenyl group, an alkynyl group, a cycloalkyl group, a cycloalkylidenemethyl group, a cycloalkenyl group, a cycloalkyloxy group, an aryloxy group, an arylalkoxy group, a cyano group, a nitro group, an amino group, a mono- or di-alkylamino group, an alkylcarbonylamino group, a carboxyl group, an alkoxycarbonyl group, a carbamoyl group, a mono- or di-alkylcarbamoyl group, an alkanoyl group, an alkylsulfonylamino group, an arylsulfonylamino group, an alkylsulfinyl group, an alkylsulfonyl group, or an arylsulfonyl group and $R^{6b}$ and $R^{7b}$ are each independently a hydrogen atom, a halogen atom, an alkyl group, a haloalkyl group, or an alkoxy group.

Among the compounds represented by the formula IB, more preferred is a compound in which $R^8$, $R^9$ and $R^{10}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, and a group represented by:

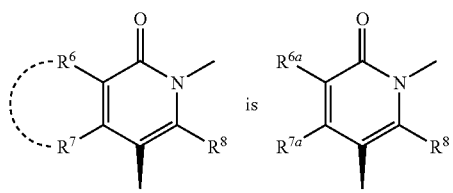

wherein $R^{6a}$, $R^{7a}$ are each independently a hydrogen atom, a halogen atom, a lower alkyl group, a cycloalkyl group, a hydroxy-lower alkyl group, a halo-lower alkyl group, a lower alkoxy-lower alkyl group, a lower alkoxy group, a cycloalkoxy group, a halo-lower alkoxy group, or a lower alkoxy-lower alkoxy group, or a group represented by:

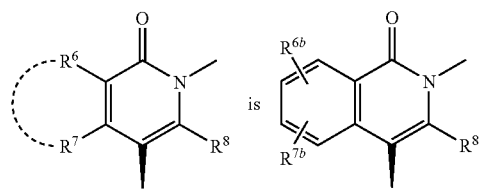

wherein $R^{6b}$ and $R^{7b}$ are each independently a hydrogen atom, a halogen atom, a lower alkyl group, a halo-lower alkyl group, or a lower alkoxy group.

In another aspect of the present invention, preferable examples of the compound I include a compound represented by the following formula IC:

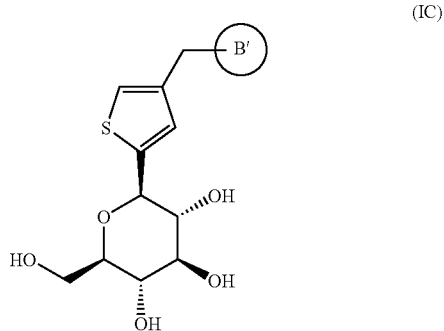

wherein Ring B' is an optionally substituted benzene ring, an optionally substituted unsaturated monocyclic heterocyclic ring, or an optionally substituted unsaturated fused heterobicyclic ring.

Preferable examples of Ring B' include a benzene ring and a heterocyclic ring, both of which may have a substituent(s) selected from the group consisting of a halogen atom; a cyano group; a lower alkyl group optionally substituted by a halogen atom; a lower alkoxy group optionally substituted by a halogen atom; a lower alkanoyl group; a mono- or di-lower alkylamino group; a lower alkoxycarbonyl group; a carbamoyl group; a mono- or di-lower alkylcarbamoyl group; a phenyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; a heterocyclyl group optionally substituted by a substituent(s) selected from a halogen atom, a cyano group, a lower alkyl group optionally substituted by a halogen atom, a lower alkoxy group optionally substituted by a halogen atom, a lower alkanoyl group, a mono- or di-lower alkylamino group, a lower alkoxycarbonyl group, a carbamoyl group, or a mono- or di-lower alkylcarbamoyl group; an alkylene group; and an oxo group.

More preferable examples of Ring B' include a benzene ring which may be substituted by a substituent selected from the group consisting of a halogen atom; a cyano group; a lower alkyl group optionally substituted by a halogen atom; a lower alkoxy group optionally substituted by a halogen atom; a mono- or di-lower alkylamino group; a phenyl group optionally substituted by a halogen atom, a cyano group, a lower alkyl group optionally substituted by a halogen atom, a lower alkoxy group optionally substituted by a halogen atom; a heterocyclyl group optionally substituted by a halogen atom, a cyano group, a lower alkyl group optionally substituted by a halogen atom, a lower alkoxy group optionally substituted by a halogen atom.

Preferred compound of the present invention may be selected from the following group:

1-(β-D-glucopyranosyl)-4-chloro-3-(6-ethylbenzo[b]thiophen-2-ylmethyl)benzene;
1-(β-D-glucopyranosyl)-4-chloro-3-[5-(5-thiazolyl)-2-thienylmethyl]benzene;
1-(β-D-glucopyranosyl)-4-chloro-3-(5-phenyl-2-thienylmethyl)benzene;
1-(β-D-glucopyranosyl)-4-methyl-3-[5-(4-fluorophenyl)-2-thienylmethyl]benzene;
1-(β-D-glucopyranosyl)-4-chloro-3-[5-(2-pyrimidinyl)-2-thienylmethyl]benzene;
1-(β-D-glucopyranosyl)-4-methyl-3-[5-(2-pyrimidinyl)-2-thienylmethyl]benzene;
1-(β-D-glucopyranosyl)-4-chloro-3-[5-(3-cyanophenyl)-2-thienylmethyl]benzene;
1-(β-D-glucopyranosyl)-4-chloro-3-[5-(4-cyanophenyl)-2-thienylmethyl]benzene;
1-(β-D-glucopyranosyl)-4-methyl-3-[5-(6-fluoro-2-pyridyl)-2-thienylmethyl]benzene;
1-(β-D-glucopyranosyl)-4-chloro-3-[5-(6-fluoro-2-pyridyl)-2-thienylmethyl]benzene;
1-(β-D-glucopyranosyl)-4-methyl-3-[5-(3-difluoromethylphenyl)-2-thienylmethyl]benzene;
1-(β-D-glucopyranosyl)-4-methyl-3-[5-(3-cyanophenyl)-2-thienylmethyl]benzene;
1-(β-D-glucopyranosyl)-4-methyl-3-[5-(4-cyanophenyl)-2-thienylmethyl]benzene;
1-(β-D-glucopyranosyl)-4-chloro-3-[5-(6-fluoro-3-pyridyl)-2-thienylmethyl]benzene;
1-(β-D-glucopyranosyl)-4-fluoro-3-(5-(3-cyanophenyl)-2-thienylmethyl)benzene;
the pharmaceutically acceptable salt thereof; and the prodrug thereof.

Particularly Preferred compounds of the present invention include:

1-(β-D-glucopyranosyl)-4-methyl-3-[5-(3-cyano-phenyl)-2-thienylmethyl]benzene, or a pharmaceutically acceptable salt thereof, or a prodrug thereof;

1-(β-D-glucopyranosyl)-4-methyl-3-[5-(4-cyano-phenyl)-2-thienylmethyl]benzene, or a pharmaceutically acceptable salt thereof, or a prodrug thereof;

1-(β-D-glucopyranosyl)-4-methyl-3-[5-(4-fluoro-phenyl)-2-thienylmethyl]benzene, or a pharmaceutically acceptable salt thereof, or a prodrug thereof;

1-(β-D-glucopyranosyl)-4-chloro-3-[5-(3-cyano-phenyl)-2-thienylmethyl]benzene, or a pharmaceutically acceptable salt thereof, or a prodrug thereof;

1-(β-D-glucopyranosyl)-4-methyl-3-[5-(6-fluoro-2-pyridyl)-2-thienylmethyl]benzene, or a pharmaceutically acceptable salt thereof, or a prodrug thereof;

1-(β-D-glucopyranosyl)-4-chloro-3-[5-(6-fluoro-2-pyridyl)-2-thienylmethyl]benzene, or a pharmaceutically acceptable salt thereof, or a prodrug thereof;

1-(β-D-glucopyranosyl)-4-chloro-3-[5-(6-fluoro-3-pyridyl)-2-thienylmethyl]benzene, or a pharmaceutically acceptable salt thereof, or a prodrug thereof; and 1-(β-D-glucopyranosyl)-4-fluoro-3-(5-(3-cyanophenyl)-2-thienylmethyl)benzene, or a pharmaceutically acceptable salt thereof, or a prodrug thereof.

Abbreviations used in the specification, particularly the Schemes and Examples, are as follows

| | |
|---|---|
| Ac = | Acetyl |
| BF₃•OEt₂ = | Boron trifluoride diethyl etherate |
| BF₃•THF = | Complex of boron trifluoride and tetrahydrofuran |
| t-Bu₃P•HBF₄ = | Tri-(t-butyl)phosphine tetrafluoroboric acid adduct |
| DCE = | Dichloroethane |
| DCM = | Dichloromethane |
| DMAP = | 4-Dimethylaminopyrdine |
| DME = | 1,2-Dimethoxyethane |
| DMF = | N,N-Dimethylformamide |
| dppb = | 1,4-Bis(diphenylphosphino)butane |
| dppe = | 1,2-Bis(diphenylposhino)ethane |
| dppf = | 1,1'-Bis(diphenylphosphino)ferrocene |
| dppp = | 1,3-Bis(diphenylposhino)propane |
| Et = | Ethyl |
| EtOAc = | Ethyl acetate |
| Et₃SiH = | Triethylsilane |
| HPLC = | High Performance Liquid Chromatography |
| i-Pr₃SiH = | Triisopropylsilane |
| Me = | Methyl |
| 2-Me-THF = | 2-Methyl Tetrahydrofuran |
| Ms = | Methanesulfonyl |
| MTBE = | Methyl-t-butyl Ether |
| Ni(COD)₂ = | Bis(1,5-cyclooctadiene)nickel(0) |
| NiCl₂(dppe) = | Nickel 1,2-bis(diphenylphosphino)ethane dichloride |
| NiCl₂(dppf) = | Nickel 1,1'-bis(diphenylphosphino)ferrocene dichloride |
| NiCl₂(dppp) = | Nickel 1,3-bis(diphenylphosphino)propane dichloride |
| Ni(OAc)₂/dppe = | Nickel acetate and 1,2-bis(diphenylphosphino)ethane |
| NMM = | N-Methylmorpholine |
| Pd/C = | Palladium on carbon |
| PdCl₂(PPh₃)₂ | Bis(triphenylphosphine)palladium(II)dichloride |
| Pd(OAc)₂ = | Palladium acetate |
| Pd(OAc)₂/dppp = | Palladium acetate and 1,3-bis(diphenylphosphino)propane complex |
| Pd(OAc)₂/Et₃SiH = | Palladium acetate and triethylsilane complex |
| Pr = | Propyl |
| RaNi = | RANEY ® nickel (aluminum nickel alloy) |
| TFA = | Trifluoroacetic acid |
| THF = | Tetrahydrofuran |
| TMDSO = | Tetramethyldidiloxane |
| TMS = | Trimethylsilyl |
| TOF = | Turnover frequency (the number of reactant moles converted to the desired product per mole of catalyst used per hour) |

As used herein, unless otherwise noted, the term "isolated form" shall mean that the compound is present in a form which is separate from any solid mixture with another compound(s), solvent system or biological environment. In an embodiment, the present invention is directed to a process for the preparation of a compound of formula (I), wherein the compound of formula (I) is prepared as an isolated form. In another embodiment, the present invention is directed to a process for the preparation of a compound of formula (IA'), wherein the compound of formula (IA') is prepared as an isolated form. In another embodiment, the present invention is directed to a process for the preparation of a compound of formula (I-S), wherein the compound of formula (I-S) is prepared as an isolated form. In another embodiment, the present invention is directed to a process for the preparation of a compound of formula (I-K), wherein the compound of formula (I-S) is prepared as an isolated form.

As used herein, unless otherwise noted, the term "substantially pure" shall mean that the mole percent of impurities in the isolated compound is less than about 5 mole percent, preferably less than about 2 mole percent, more preferably, less than about 0.5 mole percent, most preferably, less than about 0.1 mole percent.

In an embodiment, the present invention is directed to a process for the preparation of a compound of formula (I), wherein the compound of formula (I) is substantially pure. In another embodiment, the present invention is directed to a process for the preparation of a compound of formula (IA'), wherein the compound of formula (IA') is substantially pure. In another embodiment, the present invention is directed to a process for the preparation of a compound of formula (I-S), wherein the compound of formula (I-S) is substantially pure. In another embodiment, the present invention is directed to a process for the preparation of a compound of formula (I-K), wherein the compound of formula (I-K) is substantially pure.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent.

In an embodiment, the present invention is directed to a process for the preparation of a compound of formula (I), wherein the compound of formula (I) is substantially free of corresponding salt forms. In another embodiment, the present invention is directed to a process for the preparation of a compound of formula (IA'), wherein the compound of formula (IA') is substantially free of corresponding salt forms. In another embodiment, the present invention is directed to a process for the preparation of a compound of formula (I-S), wherein the compound of formula (I-S) is substantially free of corresponding salt forms. In another embodiment, the present invention is directed to a process for the preparation of a compound of formula (I-K), wherein the compound of formula (I-K) is substantially free of corresponding salt forms.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

The compound of formula (I) of the present invention exhibits an excellent inhibitory activity against sodium-dependent glucose transporter, and an excellent blood glucose lowering effect. Therefore, the compound of the present invention is useful for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension. In particular, the compound of the present invention is useful in the treatment or the prophylaxis of diabetes mellitus (type 1 and type 2 diabetes mellitus, etc.), diabetic complications (such as diabetic retinopathy, diabetic neuropathy, diabetic nephropathy) or obesity, or is useful in the treatment of postprandial hyperglycemia.

The compound of formula (I) of the present invention or a pharmaceutically acceptable salt thereof may be administered either orally or parenterally, and can be used in the form of a suitable pharmaceutical preparation. Suitable pharmaceutical preparation for oral administration includes, for example, solid preparation such as tablets, granules, capsules, powders, etc., or solution preparations, suspension preparations, or emulsion preparations, etc. Suitable pharmaceutical preparation for parenteral administration includes, for example, suppositories; injection preparations and intravenous drip preparations using distilled water for injection, physiological saline solution or aqueous glucose solution; or inhalant preparations.

The dosage of the present compound of formula (I) or a pharmaceutically acceptable salt thereof may vary according to the administration routes, ages, body weight, conditions of a patient, or kinds and severity of a disease to be treated, and it is usually in the range of about 0.01 to about 300 mg/kg/day, or any amount or range therein, preferably in the range of about 0.1 to about 50 mg/kg/day, or any amount or range therein, preferably in the range of about 0.1 to about 30 mg/kg/day, or any amount or range therein.

The compound of the formula I may be used, if necessary, in combination with one or more of other antidiabetic agents, one or more agents for treating diabetic complications, and/or one or more agents for treatment of other diseases. The present compound and these other agents may be administered in the same dosage form, or in a separate oral dosage form or by injection.

The other antidiabetic agents include, for example, antidiabetic or antihyperglycemic agents including insulin, insulin secretagogues, or insulin sensitizers, or other antidiabetic agents having an action mechanism different from SGLT inhibition, and 1, 2, 3 or 4 of these other antidiabetic agents may preferably be used. Concrete examples thereof are biguanide compounds, sulfonylurea compounds, α-glucosidase inhibitors, PPARγ agonists (e.g., thiazolidinedione compounds), PPARα/γ dual agonists, dipeptidyl peptidase IV (DPP4) inhibitors, mitiglinide compounds, and/or nateglinide compounds, and insulin, glucagon-like peptide-1 (GLP-1), PTP1B inhibitors, glycogen phosphorylase inhibitors, RxR modulators, and/or glucose 6-phosphatase inhibitors.

The agents for treatment of other diseases include, for example, an anti-obesity agent, an antihypertensive agent, an antiplatelet agent, an anti-atherosclerotic agent and/or a hypolipidemic agent.

The SGLT inhibitors of the formula I may be used in combination with agents for treatment of diabetic complications, if necessary. These agents include, for example, PKC inhibitors and/or ACE inhibitors.

The dosage of those agents may vary according to ages, body weight, and conditions of patients, and administration routes, dosage forms, etc.

These pharmaceutical compositions may be orally administered to mammalian species including human beings, apes, dogs, etc., for example, in the dosage form of tablet, capsule, granule or powder, or parenterally administered in the form of injection preparation, or intranasally, or in the form of transdermal patch.

One skilled in the art will recognize that, where not otherwise specified, the reaction step(s) is performed under suitable conditions, according to known methods, to provide the desired product.

One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates-groups of the formula —C(O)O—R wherein R is for example methyl, ethyl, t-butyl, benzyl, phenylethyl, $CH_2$=CH—$CH_2$—, and the like; amides-groups of the formula —C(O)—R' wherein R' is for example methyl, phenyl, trifluoromethyl, and the like; N-sulfonyl derivatives-groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" shall mean a group which may be attached to a oxygen atom to protect said oxygen atom from participating in a reaction and which may be readily removed following the reaction. Suitable oxygen protecting groups include, but are not limited to, acetyl, benzoyl, t-butyl-dimethylsilyl, trimethylsilyl (TMS), MOM, THP, and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize that in any of the processes described herein, reactive substituents on the compounds of formula (I), such as hydroxy groups, oxo groups, carboxy groups, and the like, are preferably protected and subsequently de-protected, according to known methods, at suitable points along the synthesis route.

The present invention is directed to a process for the preparation of compounds of formula (I) as outlined in Scheme 1, below.

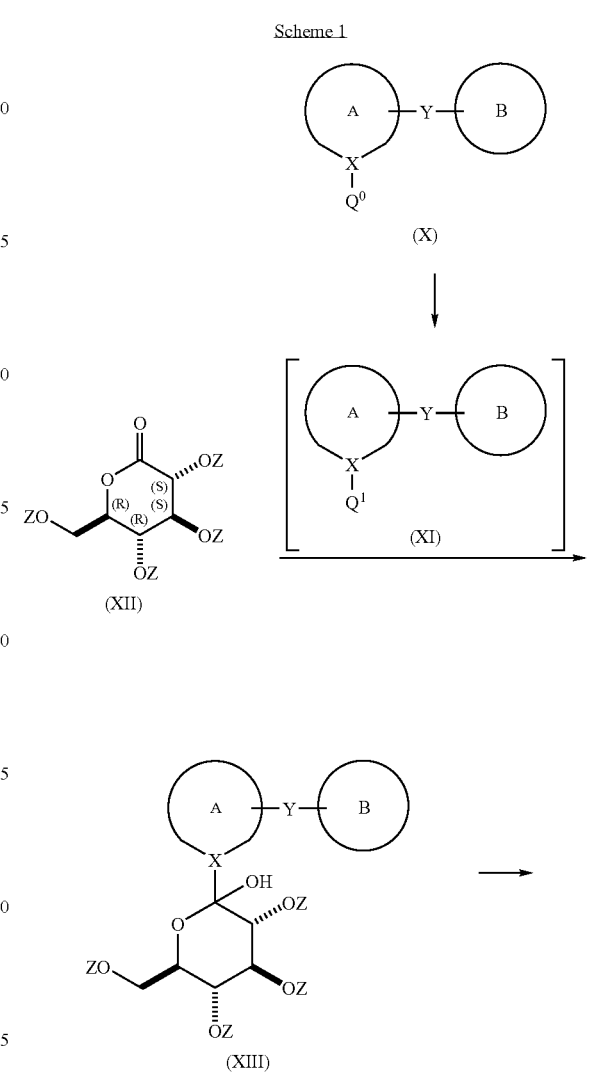

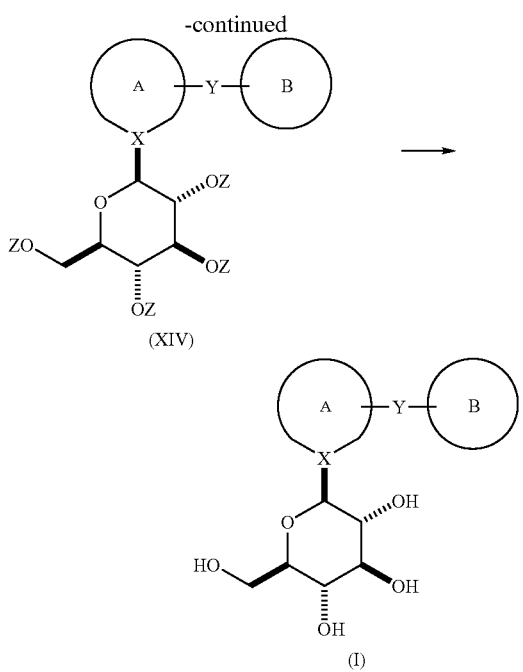

Accordingly, a suitably substituted compound of formula (X), wherein $Q^0$ is bromo or iodo, a known compound or compound prepared by known methods, is reacted with a complex of di($C_{1-4}$alkyl) magnesium with lithium chloride such as di(sec-butyl)magnesium with lithium chloride, and the like; or a complex $C_{1-4}$alkyl magnesium chloride with lithium chloride or a complex of $C_{1-4}$alkyl magnesium bromide with lithium chloride; wherein the $C_{1-4}$alkyl is preferably isopropyl or sec-butyl, more preferably sec-butyl, a known compound or compound prepared by known methods; wherein the complex of di($C_{1-4}$alkyl)magnesium with lithium chloride or the complex of $C_{1-4}$alkyl magnesium chloride with lithium chloride or the complex of $C_{1-4}$alkyl magnesium bromide with lithium chloride is preferably present in an amount in the range of from about 1.0 to 1.5 molar equivalents (relative to the moles of the compound of formula (X)), or any range therein, more preferably, in an amount of about 1.2 molar equivalents;

in an organic solvent or mixture thereof, such as toluene, THF, hexane, pentane, MTBE, 1,4-dioxane, and the like, preferably a mixture of THF and toluene; at a temperature in the range of from about ambient temperature to about −78° C., or any range therein, preferably at a temperature in the range of from about 2° C. to about 5° C.; to yield the corresponding compound of formula (XI), wherein $Q^1$ is the corresponding MgCl or MgBr.

The compound of formula (XI) is reacted with a suitably substituted compound of formula (XII), wherein Z is a suitably selected oxygen protecting group, for example Z may selected from the group consisting of acetyl, benzyl, benzoyl, pivaloyl, and isobutyryl, preferably Z is acetyl; a known compound or compound prepared by known methods;

wherein the compound of formula (XII) is preferably present in an amount in the range of from about 1.0 to about 2.0 molar equivalents, or any range therein, more preferably in an amount in the range of from about 1.0 to about 1.3 molar equivalents, or any range therein;

in an organic solvent or mixture thereof, such as toluene, THF, hexane, pentane, MTBE, 1,4-dioxane, and the like, preferably a mixture of toluene and THF; at a temperature in the range of from about ambient temperature to about −78° C., or any range therein, preferably at about −35° C.; to yield the corresponding compound of formula (XIII).

Preferably, the compound of formula (XI) is added to a mixture of the compound of formula (XII) in an organic solvent or mixture thereof, to yield the compound of formula (XIII).

The compound of formula (XIII) is reacted with a suitably selected Lewis acid, such as $BF_3.OEt_2$, $BF_3.THF$, aluminum chloride, zinc chloride, iron chloride, and the like, preferably, $BF_3.THF$ or aluminum chloride, more preferably aluminum chloride; wherein the Lewis acid is preferably present in an amount in the range of from about 0.5 to about 10.0 molar equivalents, or any range therein, more preferably, in an amount in the range of from about 0.5 to about 2.5 molar equivalents, or any range therein, most preferably about 0.8 molar equivalents;

in the presence of a suitably selected silane reagent such as triisopropylsilane, triethylsilane, tetramethyldisiloxane, and the like, preferably triethylsilane or tetramethyldisiloxane, more preferably tetramethyldisiloxane; wherein the silane reagent is preferably present in an amount in the range of from about 1.0 to about 10.0 molar equivalents, or any range therein, more preferably, in an amount in the range of from about 1.0 to about 6.0 molar equivalents, or any range therein, most preferably about 1.0 molar equivalent; wherein, in an embodiment of the present invention, the ratio of the aluminum chloride to the tetramethyldisiloxane is about 1:1.25;

in an organic solvent or mixture thereof such as DCM, DCE, acetonitrile, toluene, and the like, or in a mixture of said organic solvents, preferably in acetonitrile; preferably at a temperature in the range of from about 0° C. to about reflux, or any range therein, more preferably at about 45° C.; to yield the corresponding compound of formula (XIV).

The compound of formula (XIV) is preferably slurried or dissolved in a solvent, more preferably slurried; and then filtered, preferably filtered at an elevated temperature, to remove impurities and/or byproducts.

The compound of formula (XIV) is de-protected according to known methods. For example, the compound of formula (XIV) is reacted with a suitably selected base such as LiOH, NaOH, $NaOCH_3$, and the like, preferably $NaOCH_3$; wherein the base is preferably present in an amount in the range of from about 0.1 to about 2.0 molar equivalent, or any range therein, more preferably from about 0.5 to about 1.5 molar equivalents, or any range therein, most preferably about 1.0 molar equivalents; in an organic solvent or mixture thereof, such as methanol, ethanol, THF, and the like, preferably in methanol; preferably at about room temperature; to yield the corresponding compound of formula (I).

One skilled in the art will further recognize that, depending on the particular protecting group, Z, other reagents may be used in the de-protection step including, but not limited to, Pd/C, $Pd(OH)_2$, $PdCl_2$, $Pd(OAc)_2/Et_3SiH$, and RaNi. These reagents can be employed using various solvent systems and/or additional acid or base combinations known to one of ordinary skill.

The compound of formula (I) is preferably isolated and/or recrystallized, according to known methods.

In an embodiment, the present invention is directed to a process for the preparation of a compound of formula (I-S), as outlined in Scheme 2, below.

Scheme 2

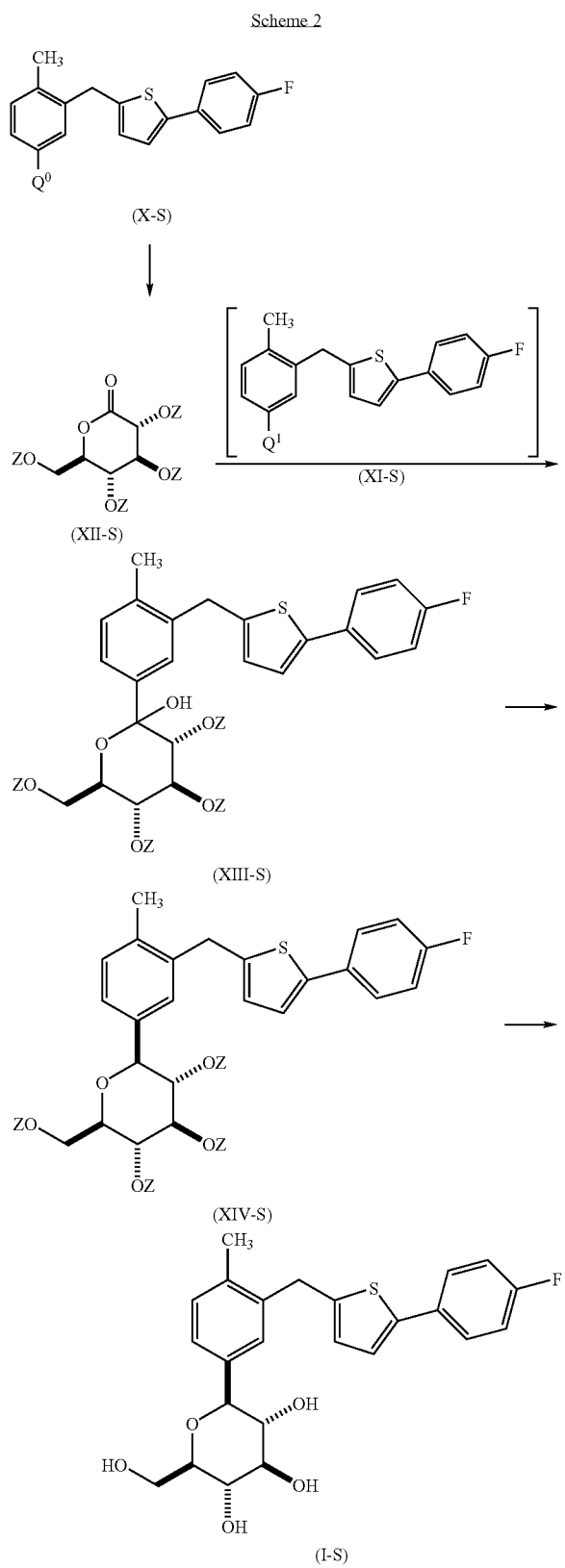

Accordingly, a suitably substituted compound of formula (X-S), wherein $Q^0$ is bromo or iodo, a known compound or compound prepared by known methods, is reacted with a complex of di($C_{1-4}$alkyl) magnesium with lithium chloride such as di(sec-butyl)magnesium with lithium chloride, and the like; or a complex $C_{1-4}$alkyl magnesium chloride with lithium chloride or a complex of $C_{1-4}$alkyl magnesium bromide with lithium chloride; wherein the $C_{1-4}$alkyl is preferably isopropyl or sec-butyl, more preferably sec-butyl, a known compound or compound prepared by known methods; wherein the complex of di($C_{1-4}$alkyl)magnesium with lithium chloride or the complex of $C_{1-4}$alkyl magnesium chloride with lithium chloride or the complex of $C_{1-4}$alkyl magnesium bromide with lithium chloride is preferably present in an amount in the range of from about 1.0 to 1.5 molar equivalents (relative to the moles of the compound of formula (X-S)), or any range therein more preferably, in an amount of about 1.2 molar equivalents;

in an organic solvent or mixture thereof, such as toluene, THF, hexane, pentane, MTBE, 1,4-dioxane, and the like, preferably a mixture of THF and toluene; at a temperature in the range of from about ambient temperature to about −78° C., or any range therein, preferably at a temperature in the range of from about 2° C. to about 5° C.; to yield the corresponding compound of formula (XI-S), wherein $Q^1$ is the corresponding MgCl or MgBr.

The compound of formula (XI-S) is reacted with a suitably substituted compound of formula (XII-S), wherein Z is a suitably selected oxygen protecting group, for example Z may selected from the group consisting of acetyl, benzyl, benzoyl, pivaloyl, and isobutyryl, preferably Z is acetyl; a known compound or compound prepared by known methods;

wherein the compound of formula (XII-S) is preferably present in an amount in the range of from about 1.0 to about 2.0 molar equivalents, or any range therein, more preferably in an amount in the range of from about 1.0 to about 1.3 molar equivalents, or any range therein;

in an organic solvent or mixture thereof, such as toluene, THF, hexane, pentane, MTBE, 1,4-dioxane, and the like, preferably a mixture of toluene and THF; at a temperature in the range of from about ambient temperature to about −78° C., or any range therein, preferably at about −35° C.; to yield the corresponding compound of formula (XIII-S).

Preferably, the compound of formula (XI-S) is added to a mixture of the compound of formula (XII-S) in an organic solvent or mixture thereof, to yield the compound of formula (XIII-S).

The compound of formula (XIII-S) is reacted with a suitably selected Lewis acid, such as $BF_3.OEt_2$, $BF_3.THF$, aluminum chloride, zinc chloride, iron chloride, and the like, preferably, $BF_3.THF$ or aluminum chloride, more preferably aluminum chloride; wherein the Lewis acid is preferably present in an amount in the range of from about 0.5 to about 10.0 molar equivalents, or any range therein, more preferably, in an amount in the range of from about 0.5 to about 2.5 molar equivalents, most preferably about 0.8 molar equivalents;

in the presence of a suitably selected silane reagent such as $iPr_3SiH$, triethylsilane, tetramethyldisiloxane and the like, preferably triethylsilane or tetramethyldisiloxane, more preferably tetramethyldisiloxane; wherein the silane reagent is preferably present in an amount in the range of from about 1.0 to about 10.0 molar equivalents, or any range therein, more preferably, in an amount in the range of from about 1.0 to about 6.0 molar equivalents, or any range therein, most preferably about 1.0 molar equivalent, wherein, in an embodiment of the present invention, the ratio of the aluminum chloride to the tetramethyldisiloxane is about 1:1.25;

in an organic solvent or mixture thereof such as DCM, DCE, acetonitrile, toluene, and the like, or in a mixture of said organic solvents, preferably in acetonitrile; preferably at a temperature in the range of from about 0° C. to about reflux, or any range therein, more preferably at about 45° C.; to yield the corresponding compound of formula (XIV-S).

The compound of formula (XIV-S) is preferably slurried or dissolved in a solvent, more preferably slurried; and then filtered, preferably filtered at an elevated temperature, to remove impurities and/or byproducts.

The compound of formula (XIV-S) is de-protected according to known methods. For example, the compound of formula (XIV-S) is reacted with a suitably selected base such as LiOH, NaOH, NaOCH$_3$, and the like, preferably NaOCH$_3$; wherein the base is preferably present in an amount in the range of from about 0.1 to about 2.0 molar equivalent, or any range therein, more preferably from about 0.5 to about 1.5 molar equivalents, or any range therein, most preferably about 1.0 molar equivalents; in an organic solvent or mixture thereof, such as methanol, ethanol, THF, and the like, preferably in methanol; preferably at about room temperature; to yield the corresponding compound of formula (I-S).

One skilled in the art will further recognize that, depending on the particular protecting group, Z, other reagents may be used in the de-protection step including, but not limited to, Pd/C, Pd(OH)$_2$, PdCl$_2$, Pd(OAc)$_2$/Et$_3$SiH, and RaNi. These reagents can be employed using various solvent systems and/or additional acid or base combinations known to one of ordinary skill.

The compound of formula (I-S) is preferably isolated and/or recrystallized, according to known methods.

In an embodiment, the present invention is directed to a process for the recrystallization of the compound of formula (I-S) comprising:

STEP A: dissolving the compound of formula (I-S) in an organic solvent such as ethyl acetate, isopropyl acetate, methanol, ethanol and the like, preferably ethyl acetate; then optionally filtering the resulting mixture;

STEP B: heating the mixture of STEP A to a temperature in the range of from about 25° C. to about 45° C., preferably to a temperature in the range of from about 30° C. to about 35° C.; then optionally filtering the resulting mixture;

STEP C: adding water to the mixture prepared in STEP B; wherein the amount of water added is preferably in an amount in the range of from about 1.0 to about 2.0 molar equivalents (relative to the moles of the compound of formula (I-S) used in STEP A), more preferably, the amount of water added is about 1.5 molar equivalents;

STEP D: adding an anti-solvent such as heptane, and the like, preferably heptane, to the mixture prepared in STEP C (wherein the anti-solvent is added to initiate precipitation); wherein the amount of anti-solvent added is preferably an amount sufficient to yield a final volume:volume ratio of organic solvent (as selected in STEP A): anti-solvent of from about 1: to about 1:5, more preferably, an amount sufficient to yield a final volume:volume ratio of about 1:2; to yield a precipitate of the compound of formula (I-S); which precipitate is preferably isolated by filtration and further, preferably dried according to known methods.

In an embodiment of the present invention, the mixture prepared in STEP C is further seeded with previously prepared crystals of the desired polymorph of the compound of formula (I-S).

In another embodiment, the present invention is directed to an alternate process for the recrystallization of the compound of formula (I-S) comprising:

STEP A: dissolving the compound of formula (I-S) in an organic solvent such as ethyl acetate, isopropyl acetate, methanol, ethanol and the like, preferably isopropyl acetate; then optionally filtering the resulting mixture;

STEP B: adding water to the mixture prepared in STEP A; wherein the amount of water added is preferably in an amount in the range of from about 1.0 to about 2.0 molar equivalents (relative to the moles of the compound of formula (I-S) used in STEP A), more preferably, the amount of water added is about 1.5 molar equivalents;

STEP C: heating the mixture of STEP B to a temperature in the range of from about 40° C. to about 65° C., preferably to a temperature in the range of from about 60° C. to about 65° C.; then optionally filtering the resulting mixture;

STEP D: cooling the mixture prepared in STEP C; to yield a precipitate of the compound of formula (I-S); which precipitate is preferably isolated by filtration and further, preferably dried according to known methods.

In an embodiment of the present invention, the mixture prepared in STEP C is further seeded with previously prepared crystals of the desired polymorph of the compound of formula (I-S).

In another embodiment, the present invention is directed to a process for the preparation of a compound of formula (I-K), as outlined in Scheme 3, below.

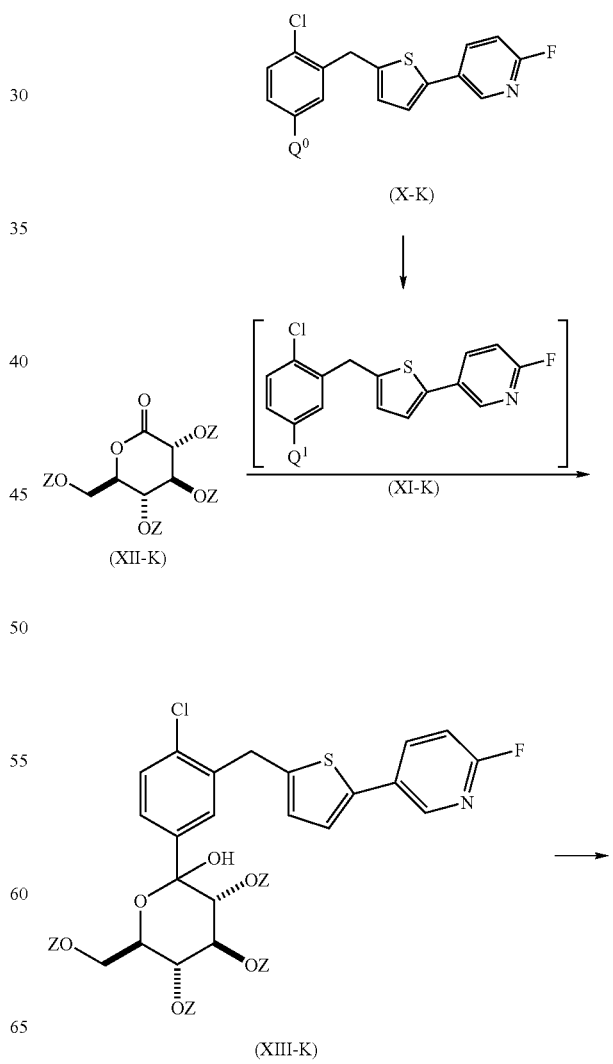

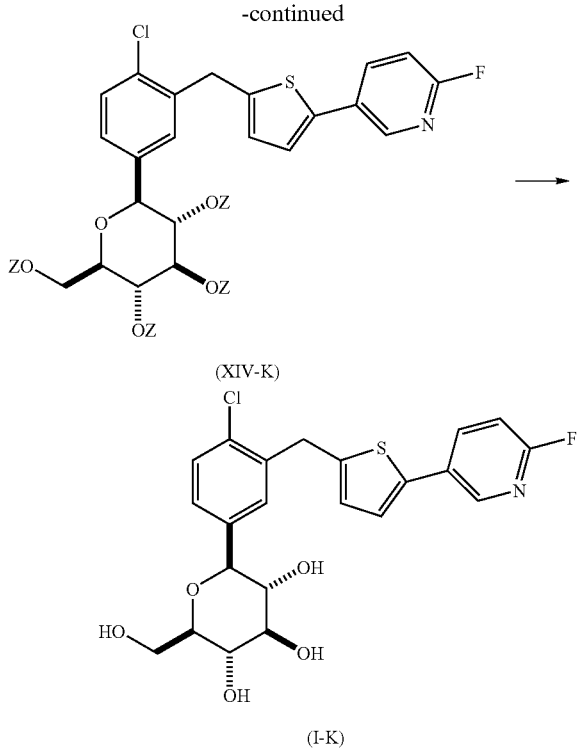

(XIV-K)

(I-K)

Accordingly, a suitably substituted compound of formula (X-K), wherein $Q^0$ is bromo or iodo, a known compound or compound prepared by known methods, is reacted with a complex of di($C_{1-4}$alkyl) magnesium with lithium chloride such as di(sec-butyl)magnesium with lithium chloride, and the like; or a complex $C_{1-4}$alkyl magnesium chloride with lithium chloride or a complex of $C_{1-4}$alkyl magnesium bromide with lithium chloride; wherein the $C_{1-4}$alkyl is preferably isopropyl or sec-butyl, more preferably sec-butyl, a known compound or compound prepared by known methods; wherein the complex of di($C_{1-4}$alkyl)magnesium with lithium chloride or the complex of $C_{1-4}$alkyl magnesium chloride with lithium chloride or the complex of $C_{1-4}$alkyl magnesium bromide with lithium chloride is preferably present in an amount in the range of from about 1.0 to 1.5 molar equivalents (relative to the moles of the compound of formula (X-K)), or any range therein, more preferably, in an amount of about 1.2 molar equivalents;

in an organic solvent or mixture thereof, such as toluene, THF, hexane, pentane, MTBE, 1,4-dioxane, and the like, preferably a mixture of THF and toluene; at a temperature in the range of from about ambient temperature to about −78° C., or any range therein, preferably at a temperature in the range of from about 2° C. to about 5° C.; to yield the corresponding compound of formula (XI-K), wherein $Q^1$ is the corresponding MgCl or MgBr.

The compound of formula (XI-K) is reacted with a suitably substituted compound of formula (XII-K), wherein Z is a suitably selected oxygen protecting group, for example Z may selected from the group consisting of acetyl, benzyl, benzoyl, pivaloyl, and isobutyryl, preferably Z is acetyl; a known compound or compound prepared by known methods;

wherein the compound of formula (XII-K) is preferably present in an amount in the range of from about 1.0 to about 2.0 molar equivalents, or any range therein, more preferably in an amount in the range of from about 1.0 to about 1.3 molar equivalents, or any range therein;

in an organic solvent or mixture thereof, such as toluene, THF, hexane, pentane, MTBE, 1,4-dioxane, and the like, preferably a mixture of toluene and THF; at a temperature in the range of from about ambient temperature to about −78° C., or any range therein, preferably at about −35° C.; to yield the corresponding compound of formula (XIII-K)

Preferably, the compound of formula (XI-K) is added to a mixture of the compound of formula (XII-K) in an organic solvent or mixture thereof, to yield the compound of formula (XIII-K).

The compound of formula (XIII-K) is reacted with a suitably selected Lewis acid, such as $BF_3.OEt_2$, $BF_3.THF$, aluminum chloride, zinc chloride, iron chloride, and the like, preferably, $BF_3.THF$ or aluminum chloride, more preferably aluminum chloride; wherein the Lewis acid is preferably present in an amount in the range of from about 0.5 to about 10.0 molar equivalents, or any range therein, more preferably, in an amount in the range of from about 0.5 to about 2.5 molar equivalents, most preferably about 0.8 molar equivalents;

in the presence of a suitably selected silane reagent such as triisopropylsilane, triethylsilane, tetramethyldisiloxane and the like, preferably triethylsilane or tetramethyldisiloxane, more preferably tetramethyldisiloxane; wherein the silane reagent is preferably present in an amount in the range of from about 1.0 to about 10.0 molar equivalents, or any range therein, more preferably, in an amount in the range of from about 1.0 to about 6.0 molar equivalents, or any range therein, most preferably about 1.0 molar equivalent; wherein, in an embodiment of the present invention, the ratio of the aluminum chloride to the tetramethyldisiloxane is about 1:1.25;

in an organic solvent or mixture thereof such as DCM, DCE, acetonitrile, toluene, and the like, or in a mixture of said organic solvents, preferably in acetonitrile; preferably at a temperature in the range of from about 0° C. to about reflux, or any range therein, more preferably at about 45° C.; to yield the corresponding compound of formula (XIV-K).

The compound of formula (XIV-K) is preferably slurried or dissolved in a solvent, more preferably slurried; and then filtered, preferably filtered at an elevated temperature, to remove impurities and/or byproducts.

The compound of formula (XIV-K) is de-protected according to known methods. For example, the compound of formula (XIV-K) is reacted with a suitably selected base such as LiOH, NaOH, $NaOCH_3$, and the like, preferably $NaOCH_3$; wherein the base is preferably present in an amount in the range of from about 0.1 to about 2.0 molar equivalent, or any range therein, more preferably from about 0.5 to about 1.5 molar equivalents, or any range therein, most preferably about 1.0 molar equivalents; in an organic solvent or mixture thereof, such as methanol, ethanol, THF, and the like, preferably in methanol; preferably at about room temperature; to yield the corresponding compound of formula (I-K).

One skilled in the art will further recognize that, depending on the particular protecting group, Z, other reagents may be used in the de-protection step including, but not limited to, Pd/C, Pd(OH)$_2$, PdCl$_2$, Pd(OAc)$_2$/Et$_3$SiH, and RaNi. These reagents can be employed using various solvent systems and/or additional acid or base combinations known to one of ordinary skill.

The compound of formula (I-K) is preferably isolated and/or recrystallized, according to known methods.

In an embodiment, the present invention is directed to processes for the preparation of the compound of formula (X-S) as outlined in more detail in Scheme 4, below.

Scheme 4

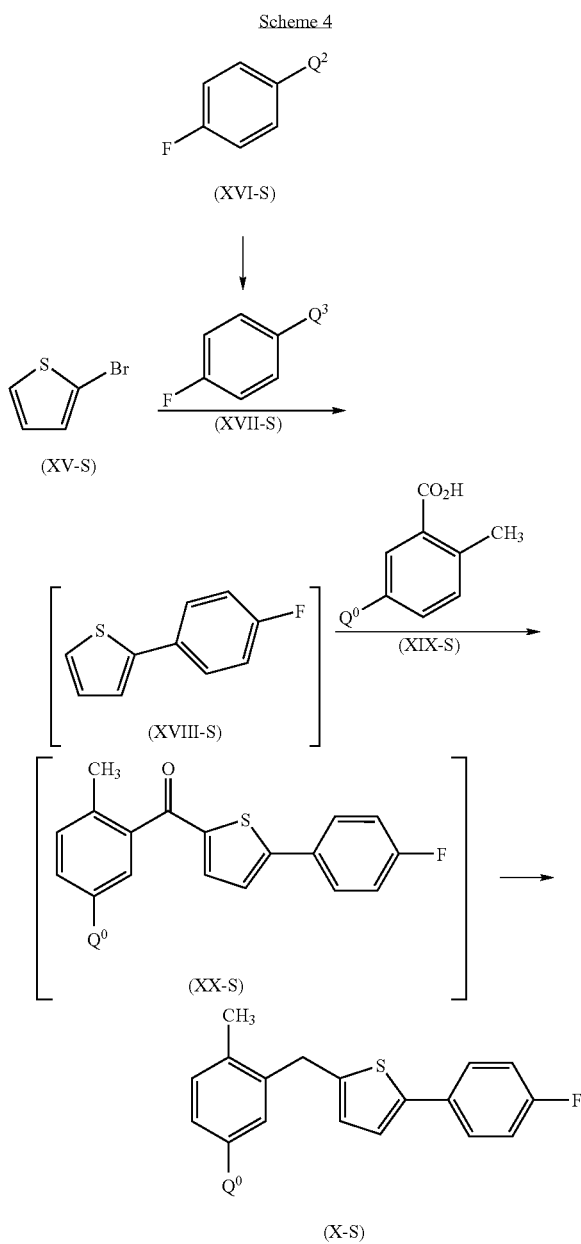

Accordingly, a compound of formula (XV-S), also known as 2-bromothiophene, a known compound or compound prepared by known methods, is reacted with a compound of formula (XVII-S), wherein $Q^3$ is —B(OH)$_2$, a known compound or compound prepared by known methods, under Suzuki coupling conditions, to yield the corresponding compound of formula (XVIII-S), also known as 2-(4-fluorophenyl)thiophene. More particularly, the compound of formula (XV-S) is reacted with the compound of formula (XVII-S), wherein $Q^3$ is —B(OH)$_2$; wherein the compound of formula (XVII-S) is preferably present in an amount in the range of from about 0.5 to about 2.0 molar equivalents, more preferably in an amount in the range of from about 0.9 to about 1.1 molar equivalents;

in the presence of a suitably selected palladium catalyst as Pd(PPh$_3$)$_4$, Pd(OAc)$_2$, PdCl$_2$(PPh$_3$)$_2$, and the like; in the presence of a suitably selected base such as Na$_2$CO$_3$, K$_3$PO$_4$, and the like; in a suitably selected organic solvent such as DME and the like; preferably, at a temperature in the range of from about 60° C. to about 85° C.; to yield the corresponding compound of formula (XVIII-S).

Alternatively, a compound of formula (XVI-S), wherein $Q^2$ is bromo, chloro, iodo, and the like, preferably bromo; is reacted with a suitably selected magnesium reagent such as Mg, isopropyl MgCl, isopropyl MgCl•LiCl, sec-butylMgCl•Li, di-(sec-butyl)Mg, tri-(n-butyl)MgLi, and the like; in a suitably selected organic solvent such as THF, 2-methyl-THF, dibutyl ether, diethyl ether, and the like; to yield the corresponding Grignard derivative, a compound of formula (XVII-S), wherein $Q^3$ is the corresponding Grignard species, more particularly, the corresponding MgBr, MgCl, MgI, or corresponding LiCl adduct (MgBr•LiCl, MgCl•LiCl, MgI•LiCl).

The compound of formula (XVII-S) is then reacted with the compound of formula (XV-S), also known as 2-bromothiophene, a known compound or compound prepared by known methods, wherein the compound of formula (XVII-S) is preferably present in an amount in the range of from about 0.5 to about 2.0 molar equivalents, more preferably in an amount in the range of from about 0.9 to about 1.2 molar equivalents;

in the presence of a suitably selected Ni or Pd catalyst such as NiCl$_2$(dppe), NiCl$_2$(dppp), NiCl$_2$(dppf), Ni(OAc)$_2$/dppe, Pd(OAc)$_2$/dppp, and the like; in a suitably selected organic solvent such as 2-methyl-THF, THF, dibutylether, diethylether, and the like; preferably at a temperature in the range of from about 0° C. to about 60° C.; to yield the corresponding compound of formula (XVIII-S), also known as 2-(4-fluorophenyl)thiophene. Preferably, the compound of formula (XVIII-S) is not isolated.

In an embodiment of the present invention, the compound of formula (XVII-S) $Q^3$ is MgBr, MgCl, MgI, or the corresponding LiCl adduct (more particularly MgBr•LiCl, MgCl•LiCl or MgI•LiCl), is reacted with the compound of formula (XV-S), also known as 2-bromothiophene; wherein the compound of formula (XVII-S) is present in an amount in the range of from about 0.8 to about 3.0 molar equivalent, preferably in an amount in the range of from about 1.0 to about 2.0 molar equivalents, more preferably in an amount in the range of from about 1.05 to about 1.2 molar equivalents;

in the presence of a suitably selected Pd or Ni catalyst, for example Pd(OAc)$_2$, palladium(II) pivalate, tetrakis(triphenylphosphine)palladium(0), bis(acetonitrile)dichloropalladium(II), dichlorobis(triphenylphosphine)palladium(II), [1,1'-bis(diphenylphosphino)ferrocene]dichloropalladium (II) complex with dichloromethane, tris(dibenzylideneacetone)dipalladium(0)-chloroform adduct, palladium(II) chloride, NiCl$_2$(dppe), NiCl$_2$(dppp), NiCl$_2$(dppf), Ni(OAc)$_2$/dppe, NiCl$_2$(PPh$_3$)$_2$, Ni(1,10-phenanthroline)$_2$, NiCl$_2$(1,10-phenanthroline), and Ni(COD)$_2$; wherein the Pd(OAc)$_2$ is preferably present in an amount in the range of from about 0.0001 mol % to about 10 mol % (based on the amount of the compound of formula (XV-S)), more preferably in an amount in the range of from about 0.001 mol % to about 1 mol %, more preferably, in an amount in the range of from about 0.01 mol % to about 0.1 mol %;

optionally in the presence of a suitably selected ligand such as trimethylphosphine, triphenylphosphine, tricyclohexylphosphine, tri(o-tolyl)phosphine, 2-(dicyclohexylphosphino)-2',4',6'-tri-i-propyl-1,1'-biphenyl (XPhos), 2-(dicyclohexylphosphino)-2'-(N,N-dimethylamino)biphenyl, 2-dicyclohexylphosphino-2',6'-di-i-propoxy-1,1'-biphenyl, 2-dicyclohexylphosphino-2',6'-dimethoxy-1,1'-biphenyl, butyldi-1-adamantylphosphine, 2-(di-t-butylphosphino)biphenyl, 2-(dicyclohexylphosphino)biphenyl, (R)-(–)-1-[(S)-

2-(diphenylphosphino)ferrocenyl]ethyldicyclohexylphosphine, 1,2-bis(diphenylphosphino)benzene (dppbenzene), 2,2'-bis(diphenylphosphino)-1,1'-binaphthyl (BINAP), bis(2-diphenylphosphinophenyl)ether (DPEphos), 4,5-bis(diphenylphosphino)-9,9-dimethylxanthene (Xantphos), dppb, dppe, dppf, dppp or t-Bu$_3$P.HBF$_4$, preferably dppf, dppp, t-Bu$_3$P.HBF$_4$, Xantphos, tricyclohexylphosphine, or XPhos, more preferably dppp or Xphos; wherein the ligand is preferably present in an amount in the range of from about 0.0001 mol % to about 10 mol % (based on the amount of the compound of formula (XV-S)), more preferably in an amount in the range of from about 0.001 mol % to about 1 mol %, more preferably, in an amount in the range of from about 0.01 mol % to about 0.1 mol %;

in a suitably selected solvent such as THF, dimethoxyethane, diethyl ether, diisopropyl ether, cyclopentyl methyl ether, tert-butyl methyl ether, dioxane, xylene, and toluene; at lower, ambient, or elevated temperature, preferably at a temperature in the range of from about −20° C. to about 150° C., more preferably at a temperature in the range of from about 30° C. to about 80° C., more preferably at a temperature in the range of from about 40° C. to about 60° C.; to yield the corresponding compound of formula (XVIII-S).

Preferably, the compound of formula (XVII-S) is added slowly, for example, at a rate where the TOF is below 12000, preferably below 2000, to a mixture of the compound of formula (XV-S), catalyst and ligand in a suitably selected solvent.

The compound of formula (XVIII-S) is reacted with a compound of formula (XIX-S), wherein Q$^0$ is bromo or iodo, preferably iodo, a known compound or compound prepared by known methods, wherein the compound of formula (XVIII-S) is preferably present in an amount in the range of from about 0.5 to about 2.0 molar equivalents, more preferably in an amount in the range of from about 0.9 to about 1.1 molar equivalents; in a suitably selected solvent such as dichloromethane, chloroform, and the like; to yield the corresponding compound of formula (XX-S). Preferably, the compound of formula (XX-S) is not isolated.

The compound of formula (XX-S) is reacted with a suitably selected reducing agent such as Et$_3$SiH, tetramethyldisiloxane, NaBH$_4$, and the like; in the presence of a Lewis Acid such as BF$_3$•Et$_2$O, BF$_3$•THF, AlCl$_3$, ZnCl$_2$, FeCl$_3$, and the like; in a suitably selected solvent such as dichloromethane, chloroform, acetonitrile, and the like, or mixture thereof; to yield the corresponding compound of formula (X-S).

In another embodiment, the present invention is directed to processes for the preparation of the compound of formula (X-K) as outlined in more detail in Scheme 5, below.

Scheme 5

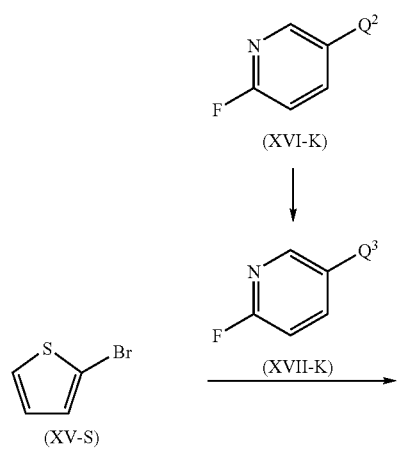

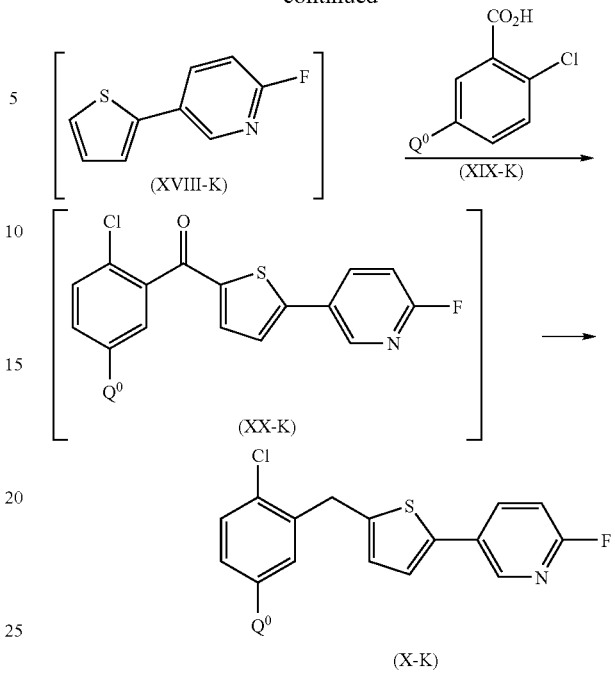

Accordingly, a compound of formula (XV-S), also known as 2-bromothiophene, a known compound or compound prepared by known methods, is reacted with a compound of formula (XVII-K), wherein Q$^3$ is —B(OH)$_2$, a known compound or compound prepared by known methods, under Suzuki coupling conditions, to yield the corresponding compound of formula (XVIII-K), also known as 2-(4-fluorophenyl)thiophene. More particularly, the compound of formula (XV-S) is reacted with the compound of formula (XVII-K), wherein Q$^3$ is —B(OH)$_2$; wherein the compound of formula (XVII-K) is preferably present in an amount in the range of from about 0.5 to about 2.0 molar equivalents, more preferably in an amount in the range of from about 0.9 to about 1.1 molar equivalents;

in the presence of a suitably selected palladium catalyst as Pd(PPh$_3$)$_4$, Pd(OAc)$_2$, PdCl$_2$(PPh$_3$)$_2$, and the like; in the presence of a suitably selected base such as Na$_2$CO$_3$, K$_3$PO$_4$, and the like; in a suitably selected organic solvent such as DME and the like; preferably, at a temperature in the range of from about 60° C. to about 85° C.; to yield the corresponding compound of formula (XVIII-K).

Alternatively, a compound of formula (XVI-K), wherein Q$^2$ is bromo, chloro, iodo, and the like, preferably bromo; is reacted with a suitably selected magnesium reagent such as Mg, isopropyl MgCl, isopropyl MgCl•LiCl, sec-butylMgCl•Li, di-(sec-butyl)Mg, tri-(n-butyl)MgLi, and the like; in a suitably selected organic solvent such as THF, 2-methyl-THF, dibutyl ether, diethyl ether, and the like; to yield the corresponding Grignard derivative, a compound of formula (XVII-K), wherein Q$^3$ is the corresponding Grignard species, more particularly, the corresponding MgBr, MgCl, MgI, or corresponding LiCl adduct (MgBr•LiCl, MgCl•LiCl, MgI•LiCl).

The compound of formula (XVII-K) is then reacted with the compound of formula (XV-S), also known as 2-bromothiophene, a known compound or compound prepared by known methods, wherein the compound of formula (XVII-K) is preferably present in an amount in the range of from about 0.5 to about 2.0 molar equivalents, more preferably in an amount in the range of from about 0.9 to about 1.2 molar equivalents;

in the presence of a suitably selected Ni or Pd catalyst such as $NiCl_2(dppe)$, $NiCl_2(dppp)$, $NiCl_2(dppf)$, $Ni(OAc)_2/dppe$, $Pd(OAc)_2/dppp$, and the like; in a suitably selected organic solvent such as 2-methyl-THF, THF, dibutylether, diethylether, and the like; preferably at a temperature in the range of from about 0° C. to about 60° C.; to yield the corresponding compound of formula (XVIII-K), also known as 2-fluoro-5-(thiophen-2-yl)pyridine. Preferably, the compound of formula (XVIII-K) is not isolated.

In an embodiment of the present invention, the compound of formula (XVII-K) $Q^3$ is MgBr, MgCl, MgI, or the corresponding LiCl adduct (more particularly MgBr•LiCl, MgCl•LiCl or MgI•LiCl), is reacted with the compound of formula (XV-K), also known as 2-bromothiophene; wherein the compound of formula (XVII-K) is present in an amount in the range of from about 0.8 to about 3.0 molar equivalent, preferably in an amount in the range of from about 1.0 to about 2.0 molar equivalents, more preferably in an amount in the range of from about 1.05 to about 1.2 molar equivalents;

in the presence of a suitably selected Pd or Ni catalyst, for example $Pd(OAc)_2$, palladium(II) pivalate, tetrakis(triphenylphosphine)palladium(0), bis(acetonitrile)dichloropalladium(II), dichlorobis(triphenylphosphine)palladium(II), [1,1'-bis(diphenylphosphino)ferrocene]dichloropalladium (II) complex with dichloromethane, tris(dibenzylideneacetone)dipalladium(0)-chloroform adduct, palladium(II) chloride, $NiCl_2(dppe)$, $NiCl_2(dppp)$, $NiCl_2(dppf)$, $Ni(OAc)_2/dppe$, $NiCl_2(PPh_3)_2$, $Ni(1,10$-phenanthroline$)_2$, $NiCl_2(1,10$-phenanthroline), and $Ni(COD)_2$; wherein the $Pd(OAc)_2$ is preferably present in an amount in the range of from about 0.0001 mol % to about 10 mol % (based on the amount of the compound of formula (XV-K)), more preferably in an amount in the range of from about 0.001 mol % to about 1 mol %, more preferably, in an amount in the range of from about 0.01 mol % to about 0.1 mol %;

optionally in the presence of a suitably selected ligand such as trimethylphosphine, triphenylphosphine, tricyclohexylphosphine, tri(o-tolyl)phosphine, 2-(dicyclohexylphosphino)-2',4',6'-tri-i-propyl-1,1'-biphenyl (XPhos), 2-(dicyclohexylphosphino)-2'-(N,N-dimethylamino)biphenyl, 2-dicyclohexylphosphino-2',6'-di-i-propoxy-1,1'-biphenyl, 2-dicyclohexylphosphino-2',6'-dimethoxy-1,1'-biphenyl, butyldi-1-adamantylphosphine, 2-(di-t-butylphosphino)biphenyl, 2-(dicyclohexylphosphino)biphenyl, (R)-(−)-1-[(S)-2-(diphenylphosphino)ferrocenyl]ethyldicyclohexylphosphine, 1,2-bis(diphenylphosphino)benzene (dppbenzene), 2,2'-bis(diphenylphosphino)-1,1'-binaphthyl (BINAP), bis(2-diphenylphosphinophenyl)ether (DPEphos), 4,5-bis(diphenylphosphino)-9,9-dimethylxanthene (Xantphos), dppb, dppe, dppf, dppp or $t\text{-}Bu_3P\cdot HBF_4$, preferably dppf, dppp, $t\text{-}Bu_3P\cdot HBF_4$, Xantphos, tricyclohexylphosphine, or XPhos, more preferably dppp or Xphos; wherein the ligand is preferably present in an amount in the range of from about 0.0001 mol % to about 10 mol % (based on the amount of the compound of formula (XV-S)), more preferably in an amount in the range of from about 0.001 mol % to about 1 mol %, more preferably, in an amount in the range of from about 0.01 mol % to about 0.1 mol %;

in a suitably selected solvent such as THF, dimethoxyethane, diethyl ether, diisopropyl ether, cyclopentyl methyl ether, tert-butyl methyl ether, dioxane, xylene, and toluene; at lower, ambient, or elevated temperature, preferably at a temperature in the range of from about −20° C. to about 150° C., more preferably at a temperature in the range of from about 30° C. to about 80° C., more preferably at a temperature in the range of from about 40° C. to about 60° C.; to yield the corresponding compound of formula (XVIII-K).

Preferably, the compound of formula (XVII-K) is added slowly, for example, at a rate where the TOF is below 12000, preferably below 2000, to a mixture of the compound of formula (XV-K), catalyst and ligand in a suitably selected solvent.

The compound of formula (XVIII-K) is reacted with a compound of formula (XIX-K), wherein $Q^0$ is bromo or iodo, preferably bromo, a known compound or compound prepared by known methods, wherein the compound of formula (XVIII-K) is preferably present in an amount in the range of from about 0.5 to about 2.0 molar equivalents, more preferably in an amount in the range of from about 0.9 to about 1.1 molar equivalents; in a suitably selected solvent such as dichloromethane, chloroform, and the like; to yield the corresponding compound of formula (XX-K). Preferably, the compound of formula (XX-K) is not isolated.

The compound of formula (XX-K) is reacted with a suitably selected reducing agent such as $Et_3SiH$, tetramethyldisiloxane, $NaBH_4$, and the like; in the presence of a Lewis Acid such as $BF_3\cdot Et_2O$, $BF_3\cdot THF$, $AlCl_3$, $ZnCl_2$, $FeCl_3$, and the like; in a suitably selected solvent such as dichloromethane, chloroform, acetonitrile, and the like, or mixture thereof; to yield the corresponding compound of formula (X-K).

The present invention is further directed to a process for the preparation of compounds of formula (IA'), as outlined in Scheme 6, below.

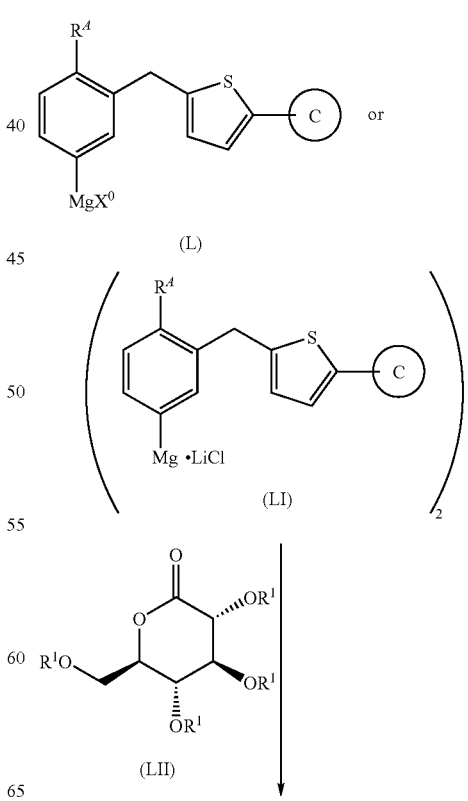

Scheme 6

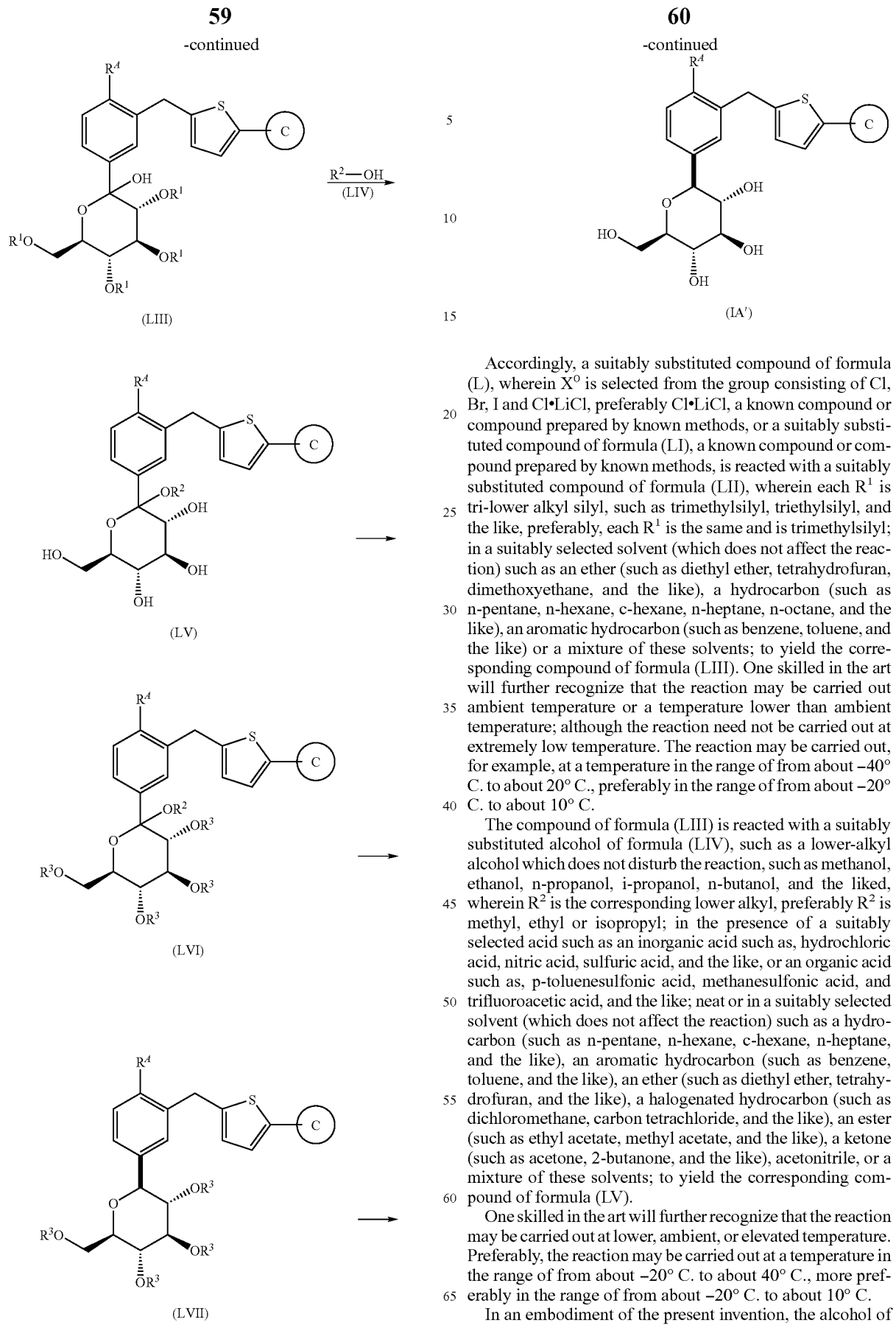

Accordingly, a suitably substituted compound of formula (L), wherein $X^0$ is selected from the group consisting of Cl, Br, I and Cl•LiCl, preferably Cl•LiCl, a known compound or compound prepared by known methods, or a suitably substituted compound of formula (LI), a known compound or compound prepared by known methods, is reacted with a suitably substituted compound of formula (LII), wherein each $R^1$ is tri-lower alkyl silyl, such as trimethylsilyl, triethylsilyl, and the like, preferably, each $R^1$ is the same and is trimethylsilyl; in a suitably selected solvent (which does not affect the reaction) such as an ether (such as diethyl ether, tetrahydrofuran, dimethoxyethane, and the like), a hydrocarbon (such as n-pentane, n-hexane, c-hexane, n-heptane, n-octane, and the like), an aromatic hydrocarbon (such as benzene, toluene, and the like) or a mixture of these solvents; to yield the corresponding compound of formula (LIII). One skilled in the art will further recognize that the reaction may be carried out ambient temperature or a temperature lower than ambient temperature; although the reaction need not be carried out at extremely low temperature. The reaction may be carried out, for example, at a temperature in the range of from about −40° C. to about 20° C., preferably in the range of from about −20° C. to about 10° C.

The compound of formula (LIII) is reacted with a suitably substituted alcohol of formula (LIV), such as a lower-alkyl alcohol which does not disturb the reaction, such as methanol, ethanol, n-propanol, i-propanol, n-butanol, and the liked, wherein $R^2$ is the corresponding lower alkyl, preferably $R^2$ is methyl, ethyl or isopropyl; in the presence of a suitably selected acid such as an inorganic acid such as, hydrochloric acid, nitric acid, sulfuric acid, and the like, or an organic acid such as, p-toluenesulfonic acid, methanesulfonic acid, and trifluoroacetic acid, and the like; neat or in a suitably selected solvent (which does not affect the reaction) such as a hydrocarbon (such as n-pentane, n-hexane, c-hexane, n-heptane, and the like), an aromatic hydrocarbon (such as benzene, toluene, and the like), an ether (such as diethyl ether, tetrahydrofuran, and the like), a halogenated hydrocarbon (such as dichloromethane, carbon tetrachloride, and the like), an ester (such as ethyl acetate, methyl acetate, and the like), a ketone (such as acetone, 2-butanone, and the like), acetonitrile, or a mixture of these solvents; to yield the corresponding compound of formula (LV).

One skilled in the art will further recognize that the reaction may be carried out at lower, ambient, or elevated temperature. Preferably, the reaction may be carried out at a temperature in the range of from about −20° C. to about 40° C., more preferably in the range of from about −20° C. to about 10° C.

In an embodiment of the present invention, the alcohol of formula (LIV) is methanol or ethanol, and the acid is an organic acid such as p-toluenesulfonic acid, methanesulfonic acid or trifluoroacetic acid. In another embodiment of the present invention, the alcohol of formula (LIV) is used as the solvent, thereby running the reaction neat.

The compound of formula (LV) is protected according to known methods, to yield the corresponding compound of formula (LVI), wherein each $R^3$ is a suitably selected oxygen protecting group, preferably each $R^3$ is the same and is acetyl. The protection may be carried out with conventional methods well known to those skilled in the art. For a general description of protecting groups and their use, see T. W. Greene et al., "Protecting Groups in Organic Synthesis", John Wiley & Sons, New York, 1999. The protection reaction may be carried out at lower, ambient, or elevated temperature. Preferably, the reaction is carried out at a temperature in the range of from about −10° C. to about 100° C., more preferably in the range of from about 5° C. to about 35° C.

Preferably, the oxygen protecting group is selected from those conventionally used as oxygen protecting groups. Suitable examples of the oxygen protecting groups include alkanoyl (such as acetyl, and the like), arylalkyl (such as benzyl, tolyl, anisyl, and the like), alkylsilyl (such as trimethylsilyl, t-butyldimethylsilyl, triethylsilyl, and the like). Further, the oxygen protecting group may form acetal or silylacetal together with adjacent hydroxyl group(s). Examples of such protecting groups include alkylidene such as isopropylidene, s-butylidene, benzylidene, or dialkylsilylene such as di-tert-butylsilylene.

The compound of formula (LVI) is reduced, according to known methods, neat or in a suitably selected solvent; to yield the corresponding compound of formula (LVII). One skilled in the art will further recognize that the reaction may be carried out at lower, ambient, or elevated temperature. Preferably, the reduction is carried out at a temperature in the range of from about −40° C. to about 40° C., more preferably in the range of from about 0° C. to about 25° C.; to yield the corresponding compound of formula (LVII).

For example, the compound of formula (LVI) may be reduced by reacting with a suitably selected silane reagent such as a tri-lower alkylsilanes (such as triethylsilane, triisopropylsilane, and the like) or a polyalkyl silanes (such as poly(methylhydrosiloxane), and the like); in the presence of a suitably selected acid, such as a suitably selected Lewis acid (such as boron trifluoride diethyl ether complex, aluminum chloride, titanium tetrachloride, and the like), or suitably selected organic acids (such as trifluoroacetic acid, trifluoromethanesulfonic acid, methanesulfonic acid, and the like); in a suitably selected solvent such as acetonitrile, dichloromethane, a mixture of acetonitrile and dichloromethane, and the like.

Alternatively, the compound of formula (LVI) may be reduced by reacting with a suitably selected borane reagent such as a suitably selected borane complex (such as borane•tetrahydrofuran, pyridine•borane, borane dimethylsulfide, t-butylamine•borane, borane•morpholine, and the like), or a suitably selected borohydride (such as sodium borohydride, sodium triacetoxyborohydride, and the like); in the presence of a suitably selected acid, such as a suitably selected Lewis acid (such as boron trifluoride diethyl ether complex, aluminum chloride, titanium tetrachloride, and the like), or suitably selected organic acids (such as trifluoroacetic acid, trifluoromethanesulfonic acid, methanesulfonic acid, and the like); neat or in a suitable solvent such as an ether such as diethyl ether, tetrahydrofuran, and the like.

Alternatively, the compound of formula (LVI) may be reduced under catalytic reduction conditions, using a suitably selected palladium catalyst such as palladium-carbon, palladium hydroxide, and the like; under a hydrogen atmosphere or in the presence of a suitably selected reducing agent (such as ammonium formate, formic acid, and the like); in a suitable selected solvent such as a carboxylic acid (such as acetic acid, and the like), an alcohol (such as methanol, and ethanol, and the like), or an ester (such as ethyl acetate, and the like).

Preferably, the compound of formula (LVI) is reduced by reacting with a suitably selected silane reagent, more preferably triethylsilane; in the presence of a suitably selected acid, more preferably a Lewis acid, more preferably, boron trifluoride etherate; in a suitably selected solvent, more preferably in acetonitrile.

The compound of formula (LVI) is de-protected according to known methods, to yield the corresponding compound of formula (IA'). More particularly, the compound of formula (LVI) is reacted to remove the oxygen protecting groups, by reduction, hydrolysis, acid treatment, or fluoride treatment. One skilled in the art will recognize that the deprotection reaction can be carried out at lower, ambient, or elevated temperature. Preferably, the de-protection reaction is carried out at a temperature in the range of from about −20° C. to about 150° C., more preferably in the range of from about 20° C. to about 50° C.

In an example, the compound of formula (LVI) is de-protected by reacting with a suitably selected base; such as an alkali metal hydroxides (such as sodium hydroxide, potassium hydroxide, lithium hydroxide, and the like), or an alkali metal alkoxide (such as sodium methoxide, sodium ethoxide, and the like); in a suitably selected solvent such as an ether (such as tetrahydrofuran, dioxane, and the like), alcohol (such as methanol, ethanol, and the like), water, or a mixture of these solvents.

In another example, the compound of formula (LVI) is de-protected by reacting with a suitably selected acid such as hydrochloric acid, p-toluenesulfonic acid, methanesulfonic acid, trifluoroacetic acid, and the like; in a suitably selected solvent such as an alcohol such as methanol, ethanol, and the like.

In another example, the compound of formula (LVI) is de-protected by reacting with a suitably selected fluoride reagent such as hydrogen fluoride, hydrogen fluoride-pyridine, tetrabutylammonium fluoride, and the like; in a suitably selected solvent such as acetic acid, an alcohol such as methanol, or ethanol, acetonitrile, or an ether such as tetrahydrofuran.

In an embodiment of the present invention, the $R^3$ protecting groups on the compound of formula (LVI) are each benzyl. Wherein the compound of formula (LVI), the protecting groups are each benzyl, the compound of formula (LVI) is de-protected by (a) catalytic reduction using a suitably selected metal catalyst (such as palladium-carbon, palladium hydroxide, platinum oxide, rhodium-carbon, and the like) under a hydrogen atmosphere in a suitably selected solvent (such as acetic acid methanol, ethanol, ethyl acetate, and the like); (b) reacting with a suitably selected de-alkylating agent such as boron tribromide, boron trichloride, boron trichloride•dimethylsulfide complex, or iodotrimethylsilane in a suitably selected solvent (such as acetonitrile, dichloromethane, and the like); or by (3) reacting with a suitably selected lower alkylthiol such as ethanethiol in the presence of a suitably selected Lewis acid (such as boron trifluoride diethyl ether complex, and the like) in a suitably selected solvent (such as dichloromethane, and the like).

In an embodiment of the present invention, $R^1$ is trimethylsilyl, $R^2$ is methyl, ethyl or isopropyl, and $R^3$ is acetyl.

Compounds of formula (L) are known compounds or compounds prepared according to known methods. In an example, the compounds of formula (L) may be prepared as outlined in Scheme 7 below.

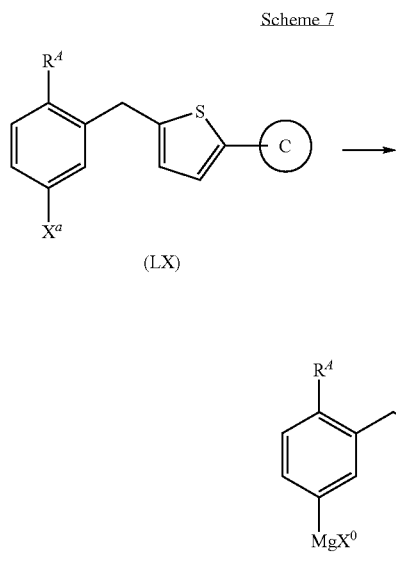

Accordingly, a suitably substituted compound of formula (LX), wherein $X^a$ is bromo or iodo, a known compound or compound prepared by known methods, is reacted with a suitably selected alkylmagnesium halide, such as an alkylmagnesium chloride such as methylmagnesium chloride, i-propylmagnesium chloride, s-butylmagnesium chloride, and the like; an alkylmagnesium bromide such as methylmagnesium bromide, i-propylmagnesium bromide, s-butylmagnesium bromide, and the like; or an alkylmagnesium iodide such as methylmagnesium chloride, i-propylmagnesium chloride, s-butylmagnesium chloride, and the like;

or with a suitably selected alkylmagnesium chloride/lithium chloride reagent such as i-propylmagnesium chloride/lithium chloride, s-butylmagnesium chloride/lithium chloride, and the like; wherein the i-propyl magnesium chloride/lithium chloride is used for the preparation of the compounds of formula (L) wherein $X^0$ is Cl.LiCl; wherein the i-propylmagnesium chloride/lithium chloride is preferably present in an amount in the range of from about 0.95 to about 1.6 molar equivalent, more preferably in an amount in the range of from about 1.05 to about 1.10 molar equivalent;

in a suitably selected solvent (which does not disturb the reaction) such as a suitably selected ether such as tetrahydrofuran, diethyl ether, and the like, to yield the corresponding compound of formula (L).

One skilled in the art will recognize that the compound of formula (LX) may be reacted to yield the corresponding compound of formula (L) at lower, ambient, or elevated temperature. Preferably, the reaction is carried out at a temperature in the range of from about −20° C. to about 40° C., preferably in the range of from about −10° C. to about 10° C.

Compounds of formula (LI) are known compounds or compounds prepared according to known methods. In an example, the compounds of formula (LI) may be prepared as outlined in Scheme 8, below.

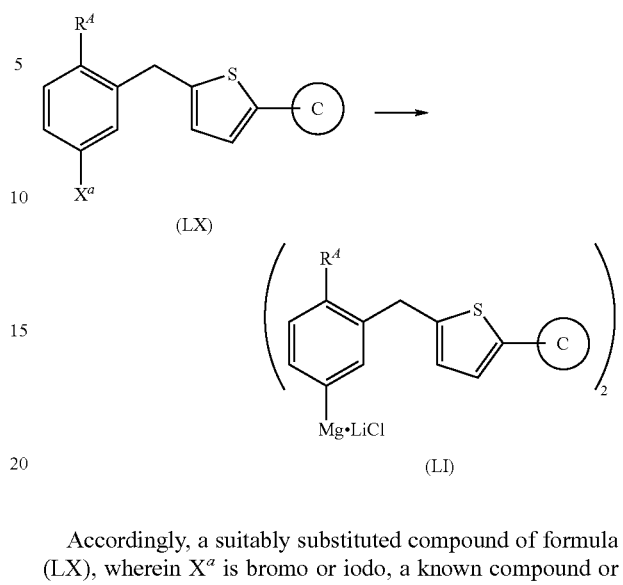

Accordingly, a suitably substituted compound of formula (LX), wherein $X^a$ is bromo or iodo, a known compound or compound prepared by known methods, is reacted with a suitably selected dialkylmagnesium/lithium chloride such as di(i-propyl)magnesium chloride/lithium chloride, di(s-butyl) magnesium chloride/lithium chloride, and the like; in a suitably selected solvent;

One skilled in the art will recognize that compounds of formula (L) and compounds of formula (LI), prepared as described above may be used without further purification.

Compounds of formula (LX) are known compounds or compounds prepared according to known methods. In an example, the compounds of formula (LX) may be prepared as outlined in Scheme 9, below.

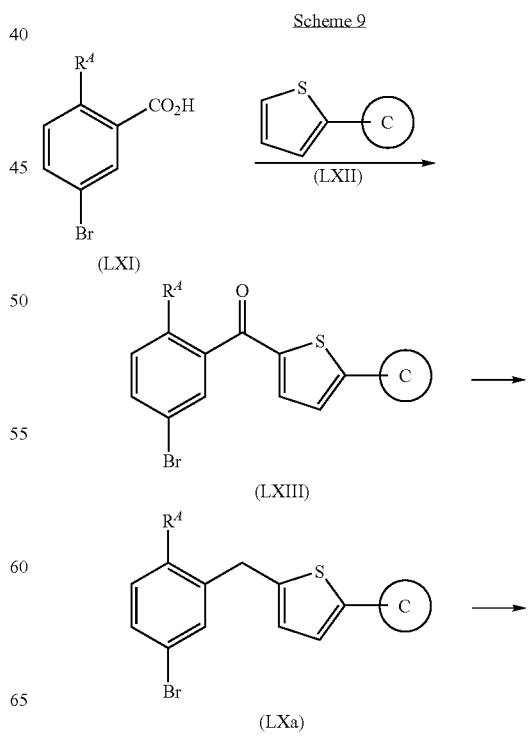

-continued

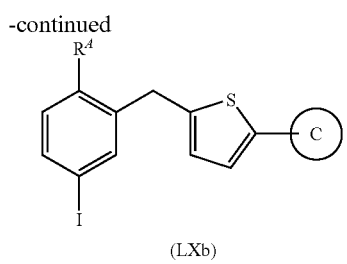

(LXb)

Accordingly, a suitably substituted compound of formula (LXI), a known compound or compound prepared by known methods, is reacted with a suitably substituted compound of formula (LXII), a known compound or compound prepared by known methods, under acylating conditions, to yield the corresponding compound of formula (LXIII).

In an embodiment, the compound of formula (LXI) is reacted with a suitably selected halogenating reagent such as thionyl chloride, oxalyl chloride, and the like; optionally in the presence of a catalytic amount of a suitably selected activator (such as dimethylformamide, and the like); neat or in a suitably selected solvent such as a suitably selected halogenated hydrocarbon such as dichloromethane, chlorobenzene, carbon tetrachloride, and the like; at lower, ambient, or elevated temperature, for example, at a temperature in the range of from about 0° C. to about 50° C.; followed by reaction with the compound of formula (LXIII).

In another embodiment, the compound of formula (LXI) is reacted with a suitably substituted compound of formula (LXII); in the presence of a suitably selected Lewis acid such as $AlCl_3$, $TiCl_4$, $FeCl_3$, and the like, according to known Friedel-Crafts acylation methods; in a suitably selected solvent; such as a hydrocarbon (such as n-pentane, n-hexane, c-hexane, n-heptane, and the like), an ethers (such as diethyl ether, tetrahydrofuran, and the like), a halogenated hydrocarbon (such as dichloromethane, carbon tetrachloride, and the like), an esters (such as ethyl acetate, methyl acetate, and the like) or a mixture of these solvents; at lower, ambient, or elevated temperature, preferably at a temperature of from about 0° C. to about 50° C.

The compound of formula (LXIII) reduced by reacting with a suitably selected reducing agent; according to known methods, to yield the corresponding compound of formula (LXa).

The compound of formula (LXIII) may be reduced by reacting with a suitably selected silane reagent such as a tri-lower alkylsilanes (such as triethylsilane, triisopropylsilane, and the like) or a polyalkyl silanes (such as poly(methylhydrosiloxane), and the like); in the presence of a suitably selected acid, such as a suitably selected Lewis acid (such as boron trifluoride diethyl ether complex, aluminum chloride, titanium tetrachloride, and the like), or suitably selected organic acids (such as trifluoroacetic acid, trifluoromethanesulfonic acid, methanesulfonic acid, and the like); in a suitably selected solvent such as acetonitrile, dichloromethane, a mixture of acetonitrile and dichloromethane, and the like.

Alternatively, the compound of formula (LXIII) may be reduced by reacting with a suitably selected borane reagent such as a suitably selected borane complex (such as borane•tetrahydrofuran, pyridine•borane, borane dimethylsulfide, and t-butylamine•borane, borane•morpholine, and the like), or a suitably selected borohydride (such as sodium borohydride, sodium triacetoxyborohydride, and the like); in the presence of a suitably selected acid, such as a suitably selected Lewis acid (such as boron trifluoride diethyl ether complex, aluminum chloride, titanium tetrachloride, and the like), or suitably selected organic acids (such as trifluoroacetic acid, trifluoromethanesulfonic acid, methanesulfonic acid, and the like); neat or in a suitable solvent such as an ether such as diethyl ether, tetrahydrofuran, and the like.

Alternatively, the compound of formula (LXIII) may be reduced under catalytic reduction conditions, using a suitably selected palladium catalyst such as palladium-carbon, palladium hydroxide, and the like; under a hydrogen atmosphere or in the presence of a suitably selected reducing agent (such as ammonium formate, formic acid, and the like); in a suitable selected solvent such as a carboxylic acid (such as acetic acid), and the like, an alcohol (such as methanol, ethanol, and the like), or an ester (such as ethyl acetate, and the like).

The compound of formula (LXa) may be further, optionally reacted with a suitably selected iodinating reagent such as and alkali metal iodide such as sodium iodide, potassium iodide, and the like; in the presence of a catalytic amount of copper (I) iodide, in a suitably selected solvent such as a halogenated hydrocarbon such as dichloromethane, chlorobenzene, carbon tetrachloride, and the like; at ambient temperature or at an elevated temperature, for example, at a temperature in the range of from about 50° C. to about 150° C.; to yield the corresponding compound of formula (LXb). (See for example, Klapars, A., et al., "Copper-Catalyzed Halogen Exchange in Aryl Halides: An Aromatic Finkelstein Reaction", *J. Am. Chem. Soc.*, (2002), 124(50), pp 14844-14845).

Compounds of formula (LXII) are known compounds or compounds prepared according to known methods. In an example, the compounds of formula (LXII) may be prepared as outlined in Scheme 10, below.

Scheme 10

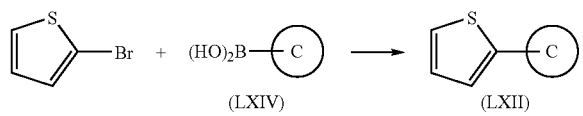

(LXIV)　　　　(LXII)

Accordingly, 2-bromothiophene, a known compound, is reacted with a suitably substituted compound of formula (LXIV), a known compound or compound prepared by known methods;

in the presence of a suitably selected palladium catalyst such as tetrakis(triphenyl-phosphine)palladium(0), palladium(II) acetate, bis(acetonitrile)dichloropalladium(II), dichlorobis(triphenylphosphine)palladium(II), [1,1'-bis(diphenylphosphino)ferrocene]dichloropalladium(II) complex with dichloromethane, tris(dibenzylidene-acetone)dipalladium(0)-chloroform adduct, palladium(II) chloride, and the like; in the presence of a suitably selected base such as an alkali metal carbonate (such as potassium carbonate, sodium carbonate, sodium bicarbonate, and the like), an alkali metal phosphate (such as potassium phosphate tribasic, sodium phosphate, sodium hydrogenphosphate, and the like), an organic base (such as N,N-diisopropylethylamine, and the like) or an alkali metal fluoride (such as cesium fluoride, potassium fluoride, and the like); optionally in the presence of a suitably selected ligand such as tricyclohexylphosphine, tri(o-tolyl)phosphine, and the like; optionally in the presence of a suitably selected additive such as copper(I) iodide, and the like;

in a suitably selected solvent such as and aromatic hydrocarbon (such as benzene, toluene, and the like), an ether (such as tetrahydrofuran, 1,2-dimethoxyethane, 1,4-dioxane, and the like), an amide (such as dimethylformamide, dimethylacetamide, 1,3-dimethyl-2-imidazolidinone, N-methylpyrrolidone, and the like), an alcohol (such as methanol, ethyl alcohol, 2-propanol, and the like), water, or a mixture of these solvents; at ambient temperature or at an elevated temperature, for example, at a temperature in the range of from about 25° C. to about 150° C., preferably in the range of from about 80° C. to about 150° C.; to yield the corresponding compound of formula (LXII).

One skilled in the art will recognize that additional starting compounds and/or reagents are commercially available or may be easily prepared according to conventional methods well known to those skilled in the art.

The present invention further comprises pharmaceutical compositions containing a compound prepared according to any of the processes described herein with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein may contain, per unit dosage unit, e.g., tablet, capsule, powder, injection, suppository, teaspoonful and the like, of from about 0.01 to about 1000 mg or any amount or range therein, and may be given at a dosage of from about 0.01 to about 300 mg/kg/day, or any amount or range therein, preferably from about 0.1 to about 50 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods of treating described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably about 10 to about 500 mg, or any amount or range therein, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound prepared according to any of the processes described herein as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described herein is required.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like. Unless otherwise noted, the identity and/or purity of the products prepared in Examples 1 through 6 was determined by HPLC.

EXAMPLE 1

3(R),4(S),5(R)-triacetoxy-6-{3-[5-(4-fluoro-phenyl)-thiophen-2-ylmethyl]-4-methyl-phenyl}-6-hydroxy-tetrahydro-pyran-2(R)-ylmethyl ester acetic acid

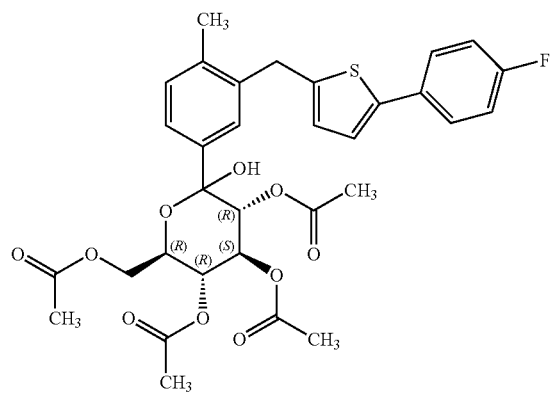

Step A: Preparation of Grignard Reagent 2-(4-Fluoro-phenyl)-5-(5-iodo-2-methyl-benzyl)-thiophene (122.48 g, 0.3 mol) was stirred in toluene (0.75 L/mol) at ambient temperature, then cooled to −10° C. To the resulting mixture was then added, via addition funnel, under argon, over about 45 minutes at −5° C. to −7° C., sec-butyl MgCl.LiCl (ca. 15% in THF; 269.70 g, 0.36 mol) and the resulting dark green solution stirred for 1 hour at between −5° C. and 0° C.

Step B:

3(R),4(S),5(R)-triacetoxy-6-oxo-tetrahydro-pyran-2(R)-ylmethyl ester acetic acid (ca 50% in toluene, 0.39 mol) was diluted with THF (0.25 L/mol) and the resulting mixture cooled to −35° C. To the mixture was then added, via syringe/addition funnel, under argon, over about 1 hour at less than about −35° C., the solution prepared in STEP A above. After 15 minutes of stirring at −35° C., a mixture of acetic acid (23 ml) and water (225 mL) was added over about 5 minutes. The resulting mixture was then allowed to warm to 25° C. The layers of the resulting biphasic mixture were separated, and the upper organic layer was washed twice with water (100 mL). The organic layer was then concentrated by distilling off the solvent to yield a residue. To the residue was then added acetonitrile (420 mL) and the resulting mixture washed with methylcyclohexane (300 mL). The resulting mixture comprised two organic layers which separated quickly. The acetonitrile solution, containing the title compound was then used in the next step without further purification or isolation of the title compound.

EXAMPLE 2

3(R),4(R),5(S)-triacetoxy-6(S)-{3-[5-(4-fluoro-phenyl)-thiophen-2-ylmethyl]-4-methyl-phenyl}-tetrahydro-pyran-2(R)-ylmethyl ester acetic acid

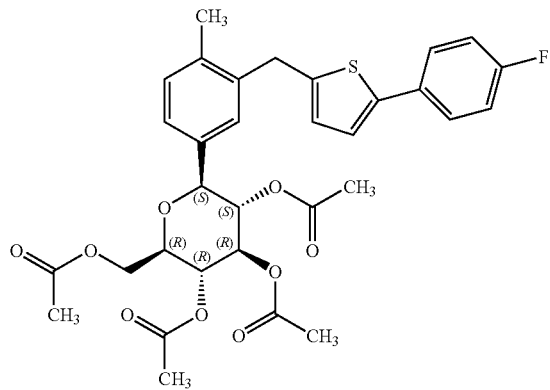

Triethylsilane (87.2 g, 0.75 mol) was added to an acetonitrile solution containing 3(R),4(S),5(R)-triacetoxy-6-{3-[5-(4-fluoro-phenyl)-thiophen-2-ylmethyl]-4-methyl-phenyl}-6-hydroxy-tetrahydro-pyran-2(R)-ylmethyl ester acetic acid (prepared as in Example 1 above, 0.30 mol) and the resulting brownish solution cooled to 2° C. Boron trifluoride etherate (46.84 g, 0.33 mol) was then added over about 30 minutes, via syringe, and the resulting mixture stirred in the ice-water bath for 1 hour. To the resulting mixture was then added 10% w/w aqueous Na₂CO₃ (330 ml), via addition funnel over about 20 minutes. The resulting mixture was then heated until complete dissolution was observed at about 45° C. The layers of the resulting tri-layer mixture were separated, the middle organic layer was allowed to cool to ambient temperature, with stirring for 16 hours, over which time crystallization was observed. The resulting mixture was then cooled in an ice bath to 2° C. and stirred for an additional 4 hours. The precipitate was filtered, washed once with methanol (75 mL) and then a second time with methanol (30 mL). The resulting off-white precipitate was dried at 50° C., in vacuo to yield the title compound.

EXAMPLE 3

3(R),4(S),5(R)-triacetoxy-6-{3-[5-(4-fluoro-phenyl)-thiophen-2-ylmethyl]-4-methyl-phenyl}-6-hydroxy-tetrahydro-pyran-2(R)-ylmethyl ester acetic acid

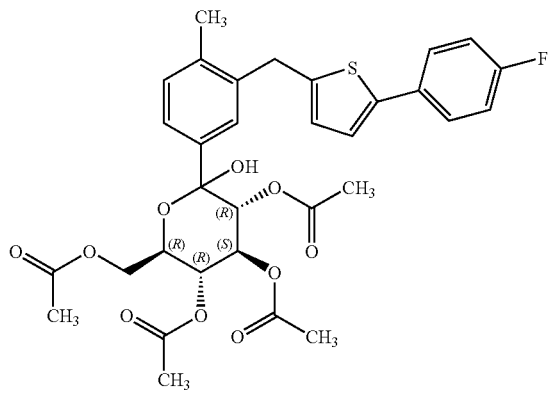

Step A: Preparation of Grignard Reagent 2-(4-Fluoro-phenyl)-5-(5-iodo-2-methyl-benzyl)-thiophene (204.14 g, 0.5 mol) was slurried in toluene (0.3 L/mol) at ambient temperature and the resulting mixture cooled to 2° C. sec-Butyl MgCl.LiCl (ca 15% in THF; 1.2 mol/mol-pure LR) was added via an addition funnel over 1 hour at 2-5° C. The resulting dark brown solution was then stirred at 2° C. for 2 hours.

Step B:

3(R),4(S),5(R)-triacetoxy-6-oxo-tetrahydro-pyran-2(R)-ylmethyl ester acetic acid (ca 50% in toluene, 0.65 mol) was diluted with THF (0.2 l/mol) and the resulting mixture cooled to −40° C. To the mixture was then added, via syringe over ½ hour at −35° to −40° C., the mixture prepared in STEP A above. The resulting mixture was then cooled to −40° C. and stirred for 30 minutes. A mixture of HCl (59.8 mL) in water (100 mL) was then added, at −40° C. over 10 minutes. The resulting mixture was warmed over 15 minutes to 20° C. and then further diluted with water (150 mL). The resulting biphasic mixture was separated and toluene (100 mL) was added to the organic layer. The organic layer was then washed with water (250 mL), the layers separated and the organic layer concentrated on a rotavap, under minimum pressure of 50 mbar, 70° C. to yield the title compound as a residue (which was used in the next synthesis step without further purification).

A sample of the prepared compound was dissolved in deuterated chloroform and the 1H and 13C NMR spectra recorded. A Bruker AVANCE-400 MHz NMR spectrometer equipped with a Bruker 5 mm BBO 400 MHz Z-gradient high resolution probe and running TOPSPIN 2.0 software, was used to collect 1-dimensional proton and carbon spectra.

$^1$H NMR (400 MHz, CHLOROFORM-d) δ ppm 1.82 (s, 3 H) 1.96 (s, 3 H) 2.05 (s, 3 H) 2.07 (s, 3 H) 2.31 (s, 3 H) 3.13 (br. s., 1 H) 4.11 (d, J=3.02 Hz, 2 H) 4.19 (dd, J=12.34, 2.52 Hz, 1 H) 4.31 (dd, J=12.34, 4.28 Hz, 1 H) 4.38-4.43 (m, 1 H) 5.08 (d, J=9.82 Hz, 1 H) 5.27 (t, J=9.82 Hz, 1 H) 5.59 (t, J=9.82 Hz, 1 H) 6.59 (d, J=3.53 Hz, 1 H) 6.98-7.05 (m, 3 H)

7.18 (d, J=7.81 Hz, 1 H) 7.36 (dd, J=7.81, 2.01 Hz, 1 H) 7.39 (d, J=1.76 Hz, 1 H) 7.44-7.48 (m, 2 H)

$^{13}$C NMR (101 MHz, CHLOROFORM-d) δ ppm 19.23 (s, 1 C) 20.35 (s, 1 C) 20.59 (s, 1 C) 20.61 (s, 1 C) 20.73 (s, 1 C) 34.11 (s, 1 C) 62.24 (s, 1 C) 68.64 (s, 1 C) 68.80 (s, 1 C) 71.60 (s, 1 C) 73.59 (s, 1 C) 97.11 (s, 1 C) 115.70 (d, J=22.01 Hz, 2 C) 122.65 (s, 1 C) 124.12 (s, 1 C) 125.90 (s, 1 C) 126.73 (s, 1 C) 127.06 (d, J=8.07 Hz, 2 C) 130.66 (s, 1 C) 130.72 (s, 1 C) 137.68 (s, 1 C) 137.80 (s, 1 C) 138.08 (s, 1 C) 141.62 (s, 1 C) 142.95 (s, 1 C) 162.08 (d, J=246.49 Hz, 1 C) 168.96 (s, 1 C) 169.61 (s, 1 C) 170.16 (s, 1 C) 170.82 (s, 1 C)

EXAMPLE 4

3(R),4(R),5(S)-triacetoxy-6(S)-{-[5-(4-fluoro-phenyl)-thiophen-2-ylmethyl]-4-methyl-phenyl}-tetrahydro-pyran-2(R)-ylmethyl ester acetic acid

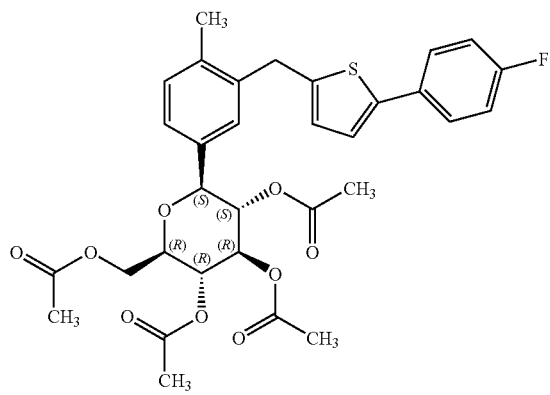

Triethylsilane (132.27 g, 1.14 mol) was added to an acetonitrile solution containing 3(R),4(S),5(R)-triacetoxy-6-{3-[5-(4-fluoro-phenyl)-thiophen-2-ylmethyl]-4-methyl-phenyl}-6-hydroxy-tetrahydro-pyran-2(R)-ylmethyl ester acetic acid (prepared as in Example 3 above, 0.455 mol) and the resulting solution stirred at 22° C. Boron trifluoride-THF complex (76.39 g, 0.55 mol) was added via addition funnel over about 3 minutes to yield a homogeneous dark brown mixture. The mixture was then warmed to 40° C., stirred strongly at 40° C. for 2.5 hours, then cooled to 20° C. Methanol (910 mL) was added to the resulting mixture over 15 minutes and the mixture stirred at 20° C. for 0.5 hours. Aq ammonium hydroxide (31.8 mL) was added to the resulting mixture (at ≤20° C., to a pH 7.2) and then stirred for 16 hours at 20° C. The resulting precipitate was filtered, washed with methanol (3×114 mL), and dried in vacuo at 60° C., to yield the title compound as a solid.

A sample of the prepared compound was dissolved in deuterated DMSO and the 1H and 13C NMR spectra recorded. A Bruker AVANCE-400 MHz NMR spectrometer equipped with a Bruker 5 mm BBO CPDUL 1H/2H-13C Z-GRD high resolution probe and running XWIN-NMR 3.5.6 software, was used to collect 1-dimensional proton and carbon spectra.

$^{1}$H NMR (600 MHz, DMSO-d$_6$) δ ppm 1.72 (s, 3 H) 1.93 (s, 3 H) 1.99 (s, 3 H) 2.02 (s, 3 H) 2.26 (s, 3 H) 4.04-4.09 (m, 2 H) 4.10-4.16 (m, 3 H) 4.65 (d, J=9.82 Hz, 1 H) 4.98 (t, J=9.63 Hz, 1 H) 5.06 (t, J=9.63 Hz, 1 H) 5.36 (t, J=9.63 Hz, 1 H) 6.76 (d, J=3.40 Hz, 1 H) 7.17 (s, 3 H) 7.20 (t, J=8.69 Hz, 2 H) 7.29 (d, J=3.78 Hz, 1 H) 7.58 (dd, J=8.50, 5.48 Hz, 2 H)

$^{13}$C NMR (151 MHz, DMSO-d$_6$) δ ppm 18.81 (s, 1 C) 20.12 (s, 1 C) 20.30 (s, 1 C) 20.42 (s, 1 C) 20.52 (s, 1 C) 33.14 (s, 1 C) 62.34 (s, 1 C) 68.48 (s, 1 C) 72.37 (s, 1 C) 73.44 (s, 1 C) 74.54 (s, 1 C) 77.90 (s, 1 C) 115.91 (d, J=20.86 Hz, 2 C) 123.42 (s, 1 C) 125.37 (s, 1 C) 126.41 (s, 1 C) 126.89 (d, J=8.78 Hz, 2 C) 128.40 (s, 1 C) 130.29 (s, 1 C) 130.48 (d, J=3.29 Hz, 1 C) 134.76 (s, 1 C) 136.21 (s, 1 C) 137.97 (s, 1 C) 140.36 (s, 1 C) 143.32 (s, 1 C) 161.39 (d, J=244.80 Hz, 1 C) 168.42 (s, 1 C) 169.40 (s, 1 C) 169.62 (s, 1 C) 170.08 (s, 1 C)

Melting Point=161.8° C.

EXAMPLE 5

2(S)-{3-[5-(4-Fluoro-phenyl)-thiophen-2-ylmethyl]-4-methyl-phenyl}-6(R)-hydroxymethyl-tetrahydro-pyran-3(R),4(R),5(S)-triol

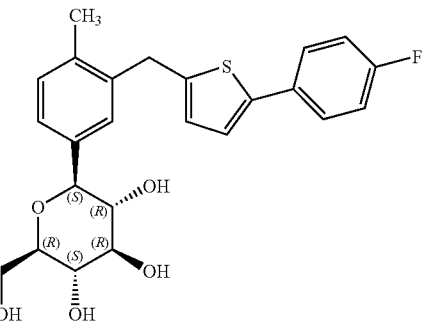

To a 3-necked round bottom flask was added methanol (244.80 mL, 3 L/mol-pure-LR), sodium methoxide (15.31 mL, 81.60 mmol) and 3(R),4(R),5(S)-triacetoxy-6(S)-{3-[5-(4-fluoro-phenyl)-thiophen-2-ylmethyl]-4-methyl-phenyl}-tetrahydro-pyran-2(R)-ylmethyl ester acetic acid (prepared as in for example, Example 4 above; 49.99 g, 81.60 mmol) and the resulting thick homogeneous mixture stirred at 20-25° C. for 1 hour. The resulting mixture was then heated to reflux temperature, about 82 mL of solvent distilled off and then cooled to 2° C. over 30 minutes. To the resulting mixture was added acetic acid (4.68 mL, 81.60 mmol). Water (114 mL) was then added with cooling, over about 15 minutes and the resulting mixture warmed to 22° C. The resulting mixture was seeded with previously prepared material (300 mg), then stirred at 22° C. for 19 hours. Additional water (49 mL) was added over 2.5 hours (to a methanol:water ratio of 50:50), the resulting mixture was cooled to 0° C. over 15 minutes, then stirred at 0° C. for 2 hours. The resulting suspension was filtered, the solid washed with 50:50 mixture of methanol:water (20 mL total), then dried at 50° C., under vacuum for 18 hours, to yield the title compound as a solid.

EXAMPLE 6

Recrystallization of 2(S)-{3-[5-(4-Fluoro-phenyl)-thiophen-2-ylmethyl]-4-methyl-phenyl}-6(R)-hydroxymethyl-tetrahydro-pyran-3(R),4(R),5(S)-triol

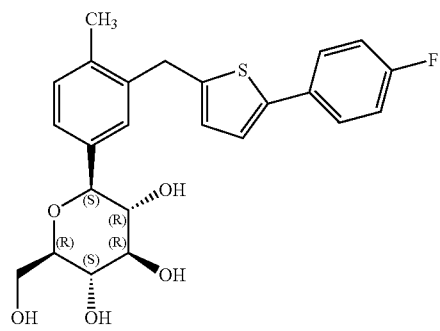

To a 3-necked round bottom flask were added 2(S)-{3-[5-(4-Fluoro-phenyl)-thiophen-2-ylmethyl]-4-methyl-phenyl}-6(R)-hydroxymethyl-tetrahydro-pyran-3(R),4(R),5(S)-triol (25.0 g, 55.15 mmol), isopropyl acetate (also known as 1-methylethyl ester acetic acid; 110 mL) and water (1.25 mL, 69.39 mmol) and the resulting mixture heated to 65° C. To the resulting mixture was then added charcoal (1 NORIT A SUPRA®, 0.5 g) and the mixture stirred at 60-65° C. for 15 minutes. The charcoal was filtered off, then washed with isopropyl acetate (15 mL). The filtrate was cooled to 50° C., seeded with previously prepared material (0.25 g), then stirred at 50° C. for 4 hours. The resulting mixture was then cooled to 0° C. over 12 hours, then stirred at 0°c for 2 hours. The resulting suspension was filtered, the solid washed with isopropyl acetate, then dried at 50° C., under vacuum to yield the title compound as a solid.

A sample of the prepared compound was dissolved in deuterated DMSO and the $^1$H NMR and $^{13}$C NMR spectra recorded. A Bruker AVANCE-600 MHz NMR spectrometer equipped with a Bruker 5 mm CPDUL 1H/2H-13C Z-GRD high resolution probe and running XWIN-NMR 3.5.6 software was used.

$^1$H NMR (600 MHz, DMSO-$d_6$) δ ppm 2.27 (s, 3 H) 3.14-3.17 (m, 1 H) 3.17-3.19 (m, 1 H) 3.20-3.24 (m, 1 H) 3.25-3.29 (m, 1 H) 3.42-3.47 (m, 1 H) 3.68-3.73 (m, 1 H) 3.97 (d, J=9.44 Hz, 1 H) 4.07-4.17 (m, 2 H) 4.44 (t, J=6.04 Hz, 1 H) 4.73 (d, J=5.67 Hz, 1 H) 4.93 (d, J=4.91 Hz, 2 H) 6.80 (d, J=3.78 Hz, 1 H) 7.12 (d, J=7.55 Hz, 1 H) 7.15 (dd, J=7.55, 1.51 Hz, 1 H) 7.20 (t, J=8.69 Hz, 2 H) 7.23 (d, J=1.13 Hz, 1 H) 7.28 (d, J=3.40 Hz, 1 H) 7.57-7.61 (m, 2 H)

$^{13}$C NMR (151 MHz, DMSO-$d_6$) δ ppm 18.81 (s, 1 C) 33.44 (s, 1 C) 61.43 (s, 1 C) 70.42 (s, 1 C) 74.67 (s, 1 C) 78.48 (s, 1 C) 81.21 (s, 1 C) 81.32 (s, 1 C) 115.88 (d, J=21.96 Hz, 2 C) 123.39 (s, 1 C) 126.25 (s, 1 C) 126.36 (s, 1 C) 126.95 (d, J=7.68 Hz, 2 C) 129.06 (s, 1 C) 129.65 (s, 1 C) 130.52 (d, J=3.29 Hz, 1 C) 134.93 (s, 1 C) 137.36 (s, 1 C) 138.24 (s, 1 C) 140.22 (s, 1 C) 143.63 (s, 1 C) 161.37 (d, J=243.70 Hz, 1 C)

EXAMPLE 7

3(R),4(R),5(S)-triacetoxy-6(S)-{3-[5-(4-fluoro-phenyl)-thiophen-2-ylmethyl]-4-methyl-phenyl}-tetrahydro-pyran-2(R)-ylmethyl ester acetic acid

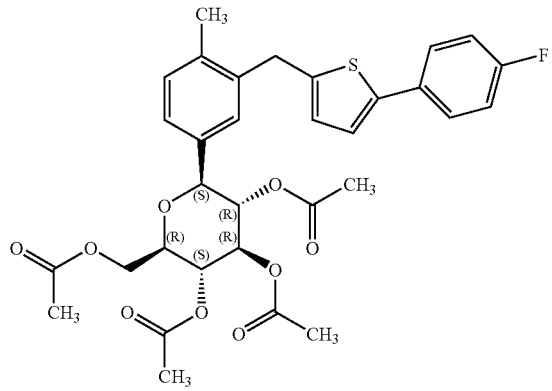

Under a nitrogen atmosphere, acetonitrile (112.50 mL, 88.12 g) was cooled to 2° C. Aluminum trichloride (13.33 g) was added in one portion and the resulting mixture stirred for 15 min, cooling to 15° C. ((CH$_3$)$_2$SiH)$_2$O (22.13 mL, 16379 g) was added in one portion at 15° C. and the resulting mixture stirred for 15 min. To the mixture was then added, at 15° C. over about 3 hours, 3(R),4(S),5(R)-triacetoxy-6-{3-[5-(4-fluoro-phenyl)-thiophen-2-ylmethyl]-4-methyl-phenyl}-6-hydroxy-tetrahydro-pyran-2(R)-ylmethyl ester acetic acid (1.0 equiv. 146.46 MI (145.26 g, 54.10% w/w in acetonitrile)). Following addition, the resulting mixture was stirred at 15° C. for 15 min, then warmed to 45° C. over about 30 min. 4-Methyl-2-pentanone (32.92 mL, 26.29 g) was added to the resulting mixture over about 15 min, which was then allowed to warm to 50° C., and stirred at 50° C. for 1 hour. Aqueous NH$_4$Cl was then added via addition funnel and the resulting mixture warmed to 65° C. over about 15 min, then stirred at 65° C. for 15 min. The resulting layers were separated, with the colorless layer between the organic and aqueous layers kept with the upper organic layer. The organic layer was washed at 65° C. with a solution of ammonium chloride (3.21 g) in water (20.00 mL), and the resulting three layers separated. The organic layer was heated to 65° C. over about 15 min, cooled to 55° C. over 15 min, then seeded with 3(R),4(R),5(S)-triacetoxy-6(S)-{3-[5-(4-fluoro-phenyl)-thiophen-2-ylmethyl]-4-methyl-phenyl}-tetrahydro-pyran-2(R)-ylmethyl ester acetic acid (1.15 g). The resulting mixture was stirred at 55° C. for 6 hours, cooled over about 15 hours to 1° C., then stirred at 1° C. for 5 hours. The resulting precipitate was filtered, washed with methanol (2×, 46.88 mL) and then dried in vacuo at 60° C. to yield the title compound as a solid.

EXAMPLE 8

2(4-Fluorophenyl)-5,5-iodo-2-methylbenzyl)thiophene

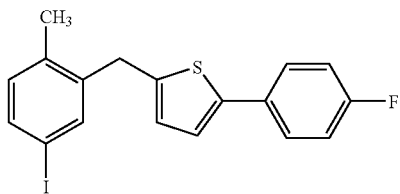 [SMILES: Cc1ccc(I)cc1Cc1ccc(-c2ccc(F)cc2)s1]

The following reactions were carried out under an argon atmosphere.

Step A: 4-Fluoro-phenylmagnesium bromide

2-Me-THF (80 ml, 0.1 L/mole) was added to Mg (19.44 g, 0.8 mol) and the resulting mixture was stirred slowly. 1-Bromo-4-fluoro-benzene (142.8 g, 0.816 mole) was dissolved in 2-Me-THF (200 ml, 0.25 L/mole) and 25 ml of this solution was added to the Mg mixture. The resulting mixture was heated to about 43° C., the remaining 1-bromo-4-fluorobenzene solution was added over about 40 minutes, while maintaining the mixture at reflux temperature. The addition funnel used to add the 1-bromo-4-fluorobenzene was rinsed with 2-methyl-THF (40 mL) and the rinse was added. The resulting mixture was stirred at 90° C. for 1 hour, then cooled to 20° C. to yield a brown-green solution containing 4-fluorophenylmagnesium bromide.

Step B: 2-(4-Fluorophenyl)thiophene

2-Bromothiophene (130.4 g, 0.8 mol) was dissolved in 2-Me-THF (240 ml, 0.3 L/mole) and the resulting mixture cooled to 2° C. NiCl$_2$(dppe) (2.11 g, 4.0 mmol) was added followed by addition, over about 40 min. at ≤30° C., of the 4-fluoro-phenylmagnesium bromide solution prepared as in STEP A above to yield a dark red solution. The solution was then stirred at 22° C. for 1.5 hrs. A solution of acetic acid (91.7 ml, 1.6 mol) in water (240 ml, 0.3 L/mol) was then added and the resulting mixture stirred strongly for 15 min. The resulting layers were separated, the organic layer was washed with water (80 ml, 0.1 L/mol), then concentrated in vacuo at 75° C. to yield 2-(4-fluorophenyl)thiophene as a brown oil.

Step C: 2-(4-fluorophenyl)-5-(5-iodo-2-methylbenzyl) thiophene

DCM (350 ml, 1 L/mol) was added to 91.7 g 5-iodo-2-methylbenzoic acid (91.7 g, 0.35 mol) and the resulting heterogeneous mixture stirred at 22° C. To the resulting mixture was then added thionyl chloride (42.5 g, 0.35 mol) via an addition funnel. The resulting mixture was warmed slowly to reflux temperature (over which time the mixture became a colorless solution and gas evolution was observed), then stirred for 1 hr, then cooled to 2° C. Aluminum chloride granules (56.0 g, 0.42 mol) were added to the resulting mixture, which was then stirred for 15 min at 2° C. A solution of 2-(4-fluorophenyl)thiophene (0.35 mol, 89.7% w/w) in DCM (0.5 L/mol) was then added via addition funnel over 10 minutes, allowing the temperature to rise during addition to 20° C. The resulting mixture was stirred at 20° C. for 2 hrs, then cooled to 2° C. Additional aluminum chloride granules (107.3 g, 0.805 mol) were added and the resulting mixture stirred for 15 min. Acetonitrile (210 ml, 0.6 L/mol) was added via addition funnel over 20 minutes at T≤20° C. Tetramethyldisiloxane (131.6 g, 0.98 mol) was then added via addition funnel over 5 minutes. The resulting mixture was slowly warmed to reflux temperature (42° C.), maintained at reflux for 3 hours, allowed to cool to 22° C. and then stirred for 16 hrs. Water (420 ml, 1.2 L/mol) was added over 30 minutes at T≤35° C. and the resulting mixture stirred strongly for 15 min. The resulting layers were separated, the organic layer washed with water (70 ml, 0.2 L/mol), then concentrated in vacuo at 50° C. to yield the title compound as a residue.

The residue (62.0 g, 0.1 mol theoretically) was suspended in a mixture of ethyl acetate (40 ml) and 2-propanol (50 ml). To the resulting mixture was added charcoal (1.2 g) and the resulting mixture heated to reflux, then stirred at reflux for 15 min. The resulting mixture was filtered warm over a filter aid, the filter washed with ethyl acetate (10 ml) and the combined filtrate and washes cooled to 2° C. over 16 hrs, over which time spontaneous crystallization was observed. The precipitate was filtered, washed with 2-propanol (50 ml) and dried in vacuo at 60° C. to yield 2-(4-fluorophenyl)-5-(5-iodo-2-methylbenzyl)thiophene as a solid.

EXAMPLE 9

5-(5-(5-bromo-2-chlorobenzyl)thiophen-2-yl)-2-fluoropyridine

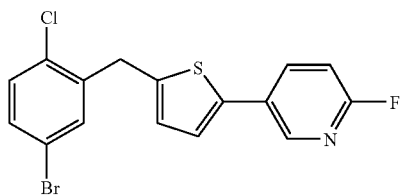 [SMILES: Fc1ccc(-c2ccc(Cc3cc(Br)ccc3Cl)s2)cn1]

Step A: (6-fluoropyridin-3-yl)magnesium bromide

Under a nitrogen atmosphere, 5-bromo-2-fluoropyridine (8.8 g, 50 mmol) was dissolved in dry THF (50 ml). To the resulting mixture was then added sec-butyl MgCl.LiCl (15% in THF, 1.5 equiv.) over about 30 min at room temperature and the resulting mixture stirred at room temperature for 2 hours.

Step B: 2-Fluoro-5-(thiophen-2-yl)pyridine

In a separate reaction vessel, under a nitrogen atmosphere were added $NiCl_2$(dppp) (0.02 equiv, 0.60 g) and THF (50 ml). 2-Bromothiophene (8.1 g, 4.81 ml, 50 mmol, 1 equiv.) was added and the resulting solution stirred for 2 min. To the resulting mixture was then added the mixture prepared in STEP A above, over about 30 min at 0° C., then allowed to warm to room temperature, with stirring. To the resulting mixture was then added diethylether, then cooled to 0° C. and treated with 1N HCl. The resulting mixture was extracted with diethylether (3×), the layers separated, the organic layer dried over $MgSO_4$, then filtered and the filtrate evaporated to yield 2-fluoro-5-(thiophen-2-yl)pyridine as a liquid residue.

Step C: (5-bromo-2-chlorophenyl-1)(5-(6-fluoropyridin-3-yl)thiophen-2-yl)methanone Under a nitrogen atmosphere, 5-bromo-2-chlorobenzoic acid (5.26 g, 22.3 mmol) was added to a mixture of DCM (30 ml) and 1 drop DMF. To the resulting mixture was then added oxalyl chloride (4.26 g, 2.93 ml, 33.5 mmol, 1.5 equiv.), which was then stirred for 2 hrs. The resulting mixture was evaporated to a residue. DCM (30 ml) was added to the residue and the mixture evaporated. This addition of DCM was repeated twice. To the resulting residue was then added, dropwise, $AlCl_3$ (3.6 g, 1.2 equiv.) in DCM (40 ml) and the resulting mixture stirred at room temperature for 2 hrs. The reaction was then quenched with water, the resulting layers separated, and the aqueous layer extracted with DCM. The combined organic fractions were washed with $K_2CO_3$, then dried over $MgSO_4$, filtered and evaporated to yield (5-bromo-2-chlorophenyl)(5-(6-fluoropyridin-3-yl)thiophen-2-yl) methanone as a residue.

Step D: 5-(5(5-bromo-2-Chlorobenzyl)thiophen-2-yl)-2-fluoropyridine

Under a nitrogen atmosphere, (5-bromo-2-chlorophenyl)(5-(6-fluoropyridin-3-yl)thiophen-2-yl)methanone (1.96 g, 4.9 mmol) was dissolved in DCM (12.5 ml). To the resulting mixture was then added acetonitrile (12.5 ml) and $Et_3SiH$ (2.29 ml, 14.3 mmol, 2.9 equiv.), resulting in the formation of a yellow suspension. The suspension was cooled to 0° C., then treated, dropwise with $BF_3.OEt_2$ (13.8 mmol, 1.75 ml, 2.8 equiv.). The resulting mixture was allowed to warm to room temperature overnight. Saturated $Na_2CO_3$ (6 ml) was added, the resulting mixture extracted with chloroform, the resulting phases separated, the organic layer dried over $MgSO_4$ and evaporated to yield a residue. The residue was dissolved in ethyl acetate, then treated with methanol, resulting in the formation of a precipitate, which was filtered, to yield 5-(5-(5-bromo-2-chlorobenzyl)thiophen-2-yl)-2-fluoropyridine as a solid.

EXAMPLE 10

2-(4-Fluorophenyl)thiophene

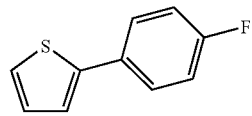 [SMILES: Fc1ccc(-c2cccs2)cc1]

A solution of 2-bromothiophene (233.0 g, 1.43 mol), 4-fluorophenyl boronic acid (200.0 g, 1.43 mol), bis(triphenylphosphine)palladium(II) dichloride (10.0 g, 14.2 mmol) and aqueous $Na_2CO_3$ (454.5 g, 4.3 mol in 1.5 L of $H_2O$) in 1,2-dimethoxyethane (2 L) was stirred at 75-80° C. (internal temperature) for 2 hours. The resulting mixture was cooled to room temperature and then stirred overnight. The solid was separated and discarded. The liquid was washed with water (2×500 mL). The combined aqueous layer was extracted with diethylether (2×500 mL). The combined organic layers were then dried over NaCl, concentrated and purified by flask distillation to yield the title compound as a white solid.

EXAMPLE 11

(3R,4S,5S,6R)-2-(34(5-(4-fluorophenyl)thiophen-2-yl)methyl)-4-methylphenyl)-6-(hydroxymethyl)-2-methoxytetrahydro-2H-pyran-3,4,5-triol

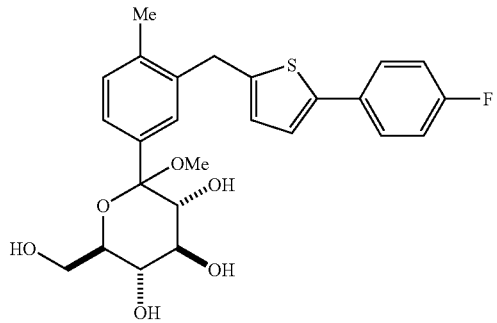 [SMILES: COC1(c2ccc(C)c(Cc3ccc(-c4ccc(F)cc4)s3)c2)O[C@H](CO)[C@@H](O)[C@H](O)[C@H]1O]

To a solution of 2-(5-iodo-2-methylbenzyl)-5-(4-fluorophenyl)thiophene (40.0 g) in anhydrous THF (200 mL) was added a solution of i-propyl magnesium chloride/lithium chloride in THF (14.5 wt %, 76.4 g) dropwise under $N_2$ at 0-5° C. The mixture was stirred for 1 hour at the same temperature, and then the mixture was added dropwise to a solution of 2,3,4,6-tetrakis-O-(trimethylsilyl)-D-glucopyrano-1,5-lactone (54.9 g; see U.S. Pat. No. 6,515,117) in anhydrous THF (80 mL) at 0-5° C. The reaction mixture was stirred for 2 hours and quenched with a solution of methanesulfonic acid (11.3 g) in methanol (400 mL) under cooling. Upon complete addition, the mixture was stirred for 2 hours under cooling, and then was warmed to room temperature and stirred for 4 hours. The mixture was quenched in a solution of $NaHCO_3$ (4.12 g) in $H_2O$ (400 mL) under cooling. The mixture was allowed to warm to room temperature, and then n-heptane was added to the mixture. After phase separation, the aqueous phase was extracted with ethyl acetate and toluene. The combined organic layer was washed with 5% aqueous $NaHCO_3$ solution, dried over anhydrous $MgSO_4$, and filtered to afford a solution of methyl 1-C-(3-{[5-(4-fluorophenyl)-2-thienyl]methyl}-4-methylphenyl)-D-glucopyranoside in ethyl acetate and toluene (assay yield 80% by HPLC; Column: Symmetry C18 4.6 mm×150 mm; Mobile Phase: Phase A, 0.1% TFA in $H_2O$; Phase B, 0.1% TFA in $CH_3CN$).

m/z (APCI), 443 ($M^+$−MeOH).

EXAMPLE 12

(3R,4S,5R,6R)-6-(acetoxymethyl)-2,3-((5-(4-fluorophenyl)thiophen-2-yl)methyl)-4-methylphenyl)-2-methoxytetrahydro-2H-pyran-3,4,5-triyl triacetate

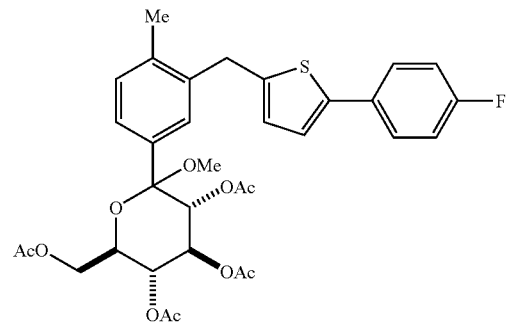 [SMILES: COC1(c2ccc(C)c(Cc3ccc(-c4ccc(F)cc4)s3)c2)O[C@H](COC(C)=O)[C@@H](OC(C)=O)[C@H](OC(C)=O)[C@H]1OC(C)=O]

To a stirred solution of methyl 1-C-(3-{[5-(4-fluorophenyl)-2-thienyl]methyl}-4-methylphenyl)-D-glucopyranoside (net weight 10.54 g) in toluene and ethyl acetate was added N-methylmorpholine (11.9 g) and 4-dimethylaminopyridine (217 mg) at room temperature. The solution was cooled to 0° C. and acetic anhydride (52.7 mL) was added dropwise below 15° C. The reaction mixture was allowed to warm to room temperature and stirred for 15 hours. The mixture was quenched with 28% $NH_3$ aqueous solution (ca. 31.6 mL) while maintaining pH range of 6 to 7. Water was added to the mixture and separated. The organic layer was washed with water and brine, dried over anhydrous $MgSO_4$ and filtered. The filtrate was concentrated in vacuo to give methyl 2,3,4,6-tetra-O-acetyl-1-C-(3-{[5-(4-fluorophenyl)-2-thienyl]methyl}-4-methylphenyl)-D-glucopyranoside (17.59 g) as yellow oil.

m/z (APCI) 660 ($M^+$+$NH_4$).

EXAMPLE 13

(2R,3R,4R,5S,6S)-2-(acetoxymethyl)-6-(3-((5-(4-fluorophenyl)thiophen-2-yl)methyl)-4-methylphenyl)tetrahydro-2H-pyran-3,4,5-triyl triacetate

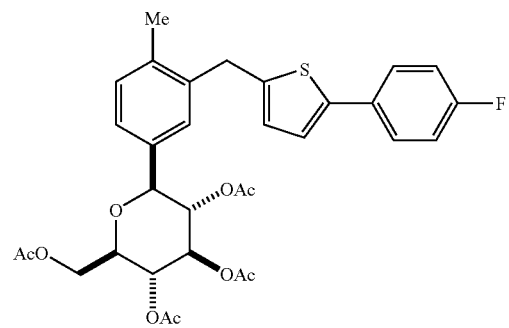

To a stirred solution of the above compound (net weight 14.25 g) in acetonitrile (114 mL) was added triethylsilane (7.74 g) at room temperature. The solution was cooled to 0° C. and boron trifluoride etherate (9.45 g) was added dropwise for 10 minutes. The reaction mixture was stirred at 0° C. for 4 hours. The mixture was quenched in a solution of 10% K₂CO₃ aqueous solution (156.8 mL) under cooling. The mixture was allowed to warm to room temperature and stirred for 15 minutes. After separation, water and ethyl acetate was added to the organic layer. The organic layer was washed with brine, and filtered. The filtrate was concentrated in vacuo. The resulting residue was suspended in ethanol and evaporated (twice). Ethanol was added to the residue and the resulting mixture was stirred for 30 minutes at 50° C., then cooled on an ice-bath. The precipitate was filtered and washed twice with ethanol, then dried to give (1S)-2,3,4,6-tetra-O-acetyl-1,5-anhydro-1-(3-{[5-(4-fluorophenyl)-2-thienyl]methyl}-4-methylphenyl)-D-glucitol (11.12 g) as white crystals.

m/z (APCI) 630 (M⁺+NH₄); mp. 160-170° C.

EXAMPLE 14

(2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol

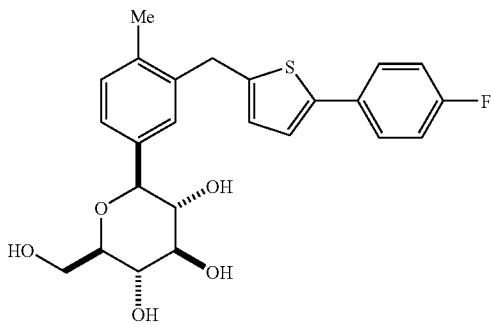

(1S)-2,3,4,6-tetra-O-acetyl-1,5-anhydro-1-(3-{[5-(4-fluorophenyl)-2-thienyl]methyl}-4-methylphenyl)-D-glucitol (5 g) was dissolved in methanol (35 mL) and tetrahydrofuran (25 mL) at room temperature. A solution of LiOH hydrate (192 mg) in water (10 mL) was added dropwise to the mixture for 30 minutes at 20-24° C. After the mixture was stirred for 19 hours at room temperature, the solvent was evaporated in vacuo. The residue was partitioned to ethyl acetate (50 mL) and water (25 mL), stirred for 15 minutes, then the layers were separated. The organic layer was washed with water. The organic layer was dried over Na₂SO₄, filtered using activated carbon pre-coated filter and evaporated. The resulting residue was dissolved in ethyl acetate (11.1 mL) at 40° C., water (241 mL) was added to the mixture at the same temperature. n-Heptane (5.6 mL) was added to the mixture at 40° C., then the mixture was seeded with a slight amount of (1S)-1,5-anhydro-1-(3-{[5-(4-fluorophenyl)-2-thienyl]methyl}-4-methylphenyl)-D-glucitol at same temperature. After stirred for 1 hour at 35° C., n-heptane (2.6 mL) was added slowly to the mixture. The resulting mixture was cooled. The precipitate was filtered and washed with ethyl acetate/n-heptane, then dried to give hemihydrate of (1S)-1,5-anhydro-1-(3-{[5-(4-fluorophenyl)-2-thienyl]methyl}-4-methylphenyl)-D-glucitol (2.93 g) as white crystals.

m/z (APCI) 462 (M⁺+NH₄); mp. 106-107° C.

EXAMPLE 15

2-(4-fluorophenyl)-5(5-iodo-2-methylbenzyl)thiophene

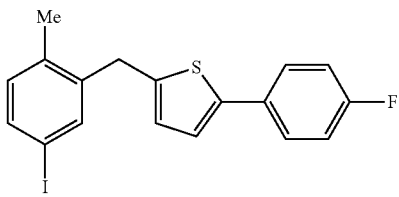 [SMILES: Cc1ccc(I)cc1Cc1ccc(-c2ccc(F)cc2)s1]

2-(5-bromo-2-methylbenzyl)-5-(4-fluorophenyl)thiophene (100 g); (see Nomura S., et al., PCT Publication, WO 2005/012326 A1, published Feb. 10, 2005) was dissolved in toluene (300 mL) at room temperature under N₂ atmosphere. Sodium iodide (83 g), copper (I) iodide (2.64 g), N,N'-dimethyl ethylenediamine (2.94 mL) and diglyme (50 mL) was added to the mixture at room temperature. The reaction mixture was heated to reflux temperature and stirred for 36 hours. Ethyl acetate (300 mL) was added to the mixture at 40° C. and the mixture was filtered using activated carbon pre-coated filter. The filtrate was washed twice with 5% aqueous NH₃ solution (100 mL). The organic layer was washed with water (100 mL) and then evaporated. The resulting residue was suspended in methanol (426 mL) at reflux temperature for 75 minutes. The resulting slurry was cooled to 25° C. and stirred for 1 hour. The precipitate was filtered and washed with methanol, then dried at 50° C. in vacuo to give 2-(5-iodo-2-methylbenzyl)-5-(4-fluorophenyl)thiophene (94.9 g) as white crystals.

m/z (APCI), 409(M⁺+H); mp 109-110° C.; ¹H NMR (400 MHz, CDCl₃); δ 7.54 (d, ⁴J$_{HH}$=1.8 Hz, 1H), 7.45-7.42 (m, 3H), 7.07-6.99 (m, 3H), 6.92 (d, ³J$_{HH}$=6.0 Hz, 1H), 6.66 (d, ³J$_{HH}$=3.6 Hz, 1H), 4.05 (s, 2H), 2.26 (s, 3H).

EXAMPLE 16

2-(4-Fluorophenyl)thiophene

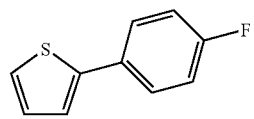 [SMILES: Fc1ccc(-c2cccs2)cc1]

To a stirred solution of 2-bromothiophene (100 g, 613.3 mol) in dry THF (220 mL), at 50° C., under a nitrogen atmosphere were added Pd(OAc)₂ (13.8 mg, 0.06 mmol) and 1,3-bis(diphenylphosphino)propane (25.3 mg, 0.06 mmol). After 5 minutes, 1.05 M 4-fluorophenylmagnesium bromide in THF (613 mL) was added over 6.0 hours (TOF=1750). The resulting mixture was stirred for 1 hour at 60° C., then cooled to 30° C. and slowly poured into a 2M HCl aqueous solution (600 mL) in an ice bath. DCM (300 mL) was added and the resulting mixture was separated, and washed with brine (200 mL). MgSO₄ (20 g) and activated charcoal (10 g) were added and the resulting mixture was stirred. The mixture was then filtered, and the filtrate concentrated to yield the title compound as a residue, which was used without further purification.

EXAMPLE 17

Oral Solid Dosage Form—Prophetic Example

As a specific embodiment of an oral composition, 100 mg of the compound prepared as in Example 5 or Example 6 above, is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A process for the preparation of compounds of formula (I)

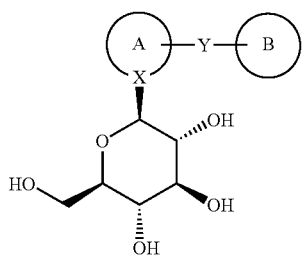

(I)

wherein Ring A and Ring B are one of the following:

(1) Ring A is an optionally substituted unsaturated monocyclic heterocyclic ring, and Ring B is an optionally substituted unsaturated monocyclic heterocyclic ring, an optionally substituted unsaturated fused heterobicyclic ring, or an optionally substituted benzene ring; or (2) Ring A is an optionally substituted benzene ring, and Ring B is an optionally substituted unsaturated monocyclic heterocyclic ring, or an optionally substituted unsaturated fused heterobicyclic ring wherein Y is linked to the heterocyclic ring of the fused heterobicyclic ring; or (3) Ring A is an optionally substituted unsaturated fused heterobicyclic ring, wherein the sugar moiety X-(sugar) and the moiety —Y-(Ring B) are both on the same heterocyclic ring of the fused heterobicyclic ring, and Ring B is an optionally substituted unsaturated monocyclic heterocyclic ring, an optionally substituted unsaturated fused heterobicyclic ring, or an optionally substituted benzene ring;

X is a carbon atom;

Y is —$(CH_2)_n$—; wherein n is 1 or 2;

provided that in Ring A, X is part of an unsaturated bond;

or a pharmaceutically acceptable salt or solvate thereof; comprising

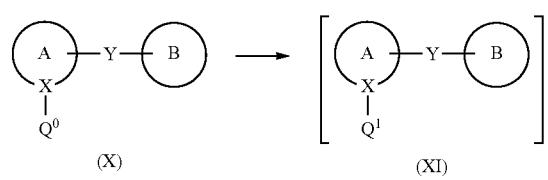

reacting a compound of formula (X) wherein $Q^0$ is bromo or iodo with a complex of di($C_{1-4}$alkyl)magnesium with lithium chloride or a complex of $C_{1-4}$alkyl magnesium chloride with lithium chloride or a complex of $C_{1-4}$alkyl magnesium bromide with lithium chloride; in an organic solvent or mixture thereof; at a temperature in the range of from about ambient temperature to about −78° C.; to yield the corresponding compound of formula (XI), wherein $Q^1$ is the corresponding MgCl or MgBr;

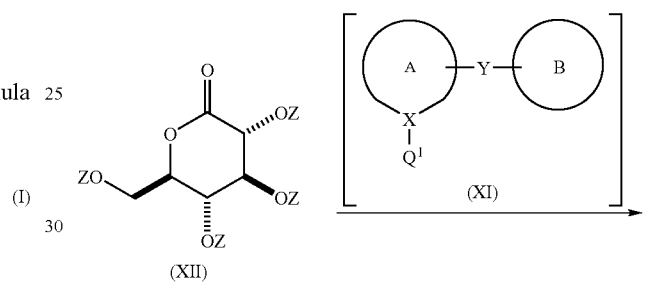

reacting the compound of formula (XI) with a compound of formula (XII), wherein Z is an oxygen protecting group selected from the group consisting of acetyl and pivaloyl; in an organic solvent or mixture thereof; at a temperature in the range of from about ambient temperature to about −78° C.; to yield the corresponding compound of formula (XIII);

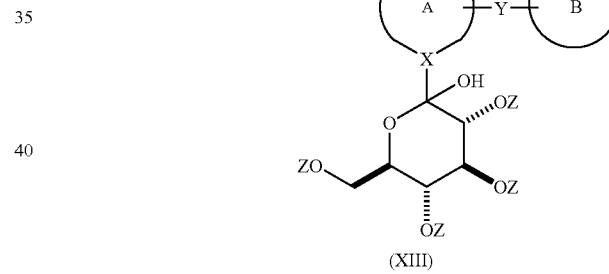

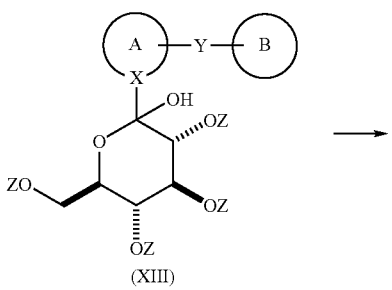

-continued

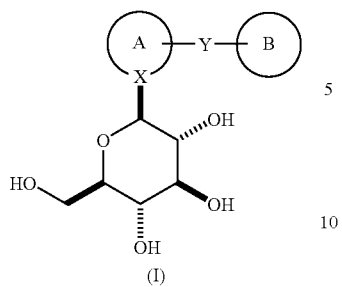

reacting the compound of formula (XIII), to yield the corresponding compound of formula (I).

2. A process as in claim 1, further comprising

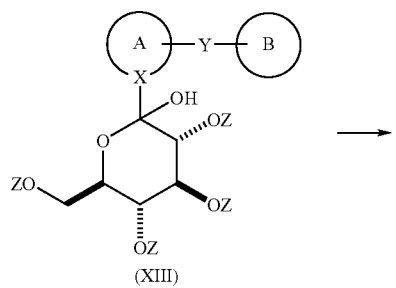

reacting the compound of formula (XIII) with a Lewis acid; in the presence of a trialkylsilane; in an organic solvent or mixture thereof; at a temperature in the range of from about 0° C. to about reflux; to yield the corresponding compound of formula (XIV);

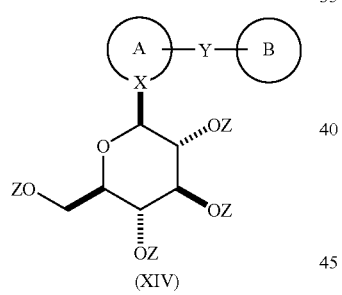

-continued

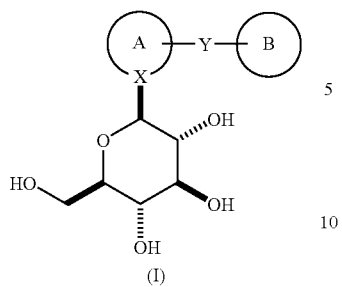

de-protecting the compound of formula (XIV); to yield the corresponding compound of formula (I).

3. A process as in claim 1, wherein

X is a carbon atom;

Ring A is selected from the group consisting of 4-methylphenyl and 4-chlorophenyl;

Y is —$CH_2$— and is bound at the 3-position of Ring A; and

Ring B is selected from the group consisting of 2-(5-(4-fluorophenyl)-thienyl) and 2-(5-(6-fluoro-pyrid-3-yl) thienyl).

4. A process as in claim 1, wherein the compound of formula (X) is reacted with a complex of di($C_{1-4}$alkyl)magnesium with lithium chloride; and wherein the complex of di($C_{1-4}$alkyl)magnesium with lithium chloride is a complex of di(sec-butyl)magnesium with lithium chloride; to yield the corresponding compound of formula (XI) wherein $Q^1$ is MgCl.

5. A process for the preparation of a compound of formula (I-S)

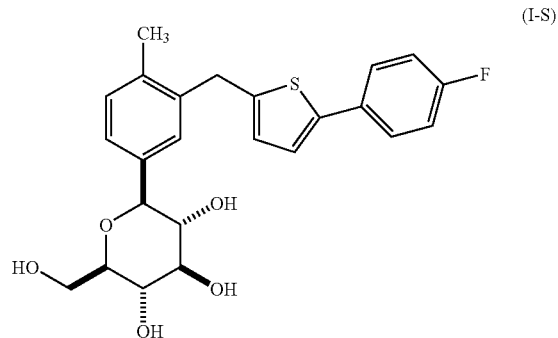

or solvate thereof; comprising

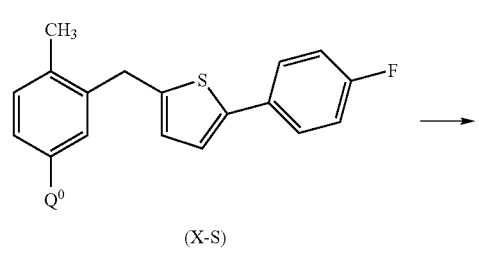

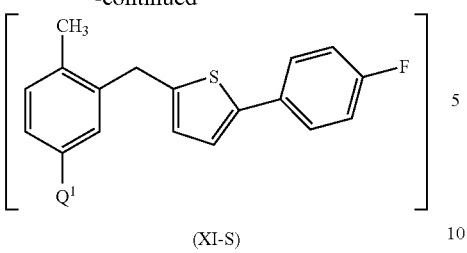

(XI-S)

reacting a compound of formula (X-S) wherein $Q^0$ is bromo or iodo with a complex of di($C_{1-4}$alkyl)magnesium with lithium chloride or complex of $C_{1-4}$alkyl magnesium chloride with lithium chloride or a complex of $C_{1-4}$alkyl magnesium bromide with lithium chloride; in an organic solvent or mixture thereof; at a temperature in the range of from about ambient temperature to about −78° C.; to yield the corresponding compound of formula (XI-S), wherein $Q^1$ is the corresponding MgCl or MgBr;

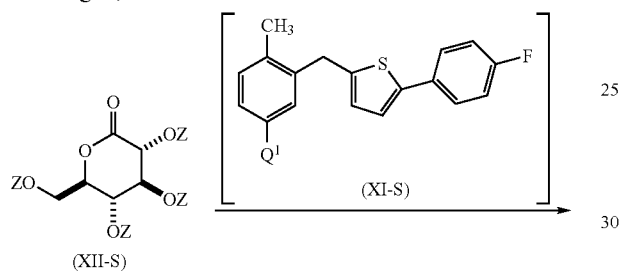

(XII-S)  (XI-S)

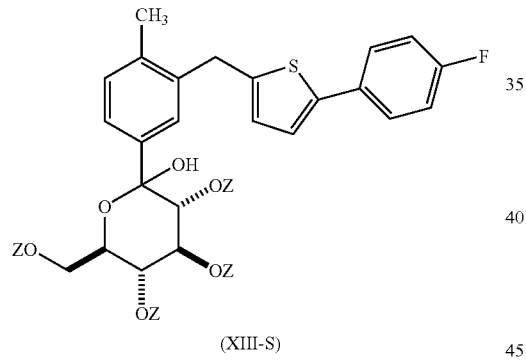

(XIII-S)

reacting the compound of formula (XI-S) with a compound of formula (XII-S), wherein Z is an oxygen protecting group selected from the group consisting of acetyl and pivaloyl; in an organic solvent or mixture thereof; at a temperature in the range of from about ambient temperature to about −78° C.; to yield the corresponding compound of formula (XIII-S);

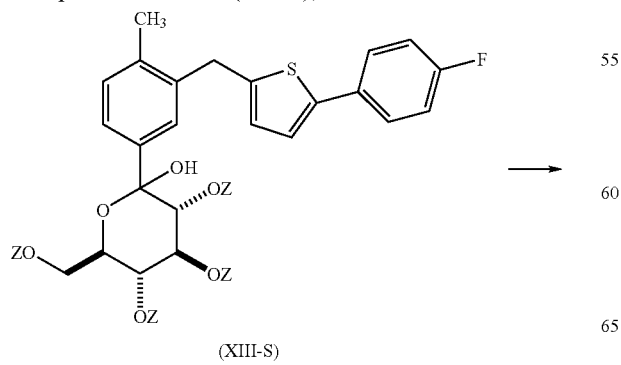

(XIII-S)

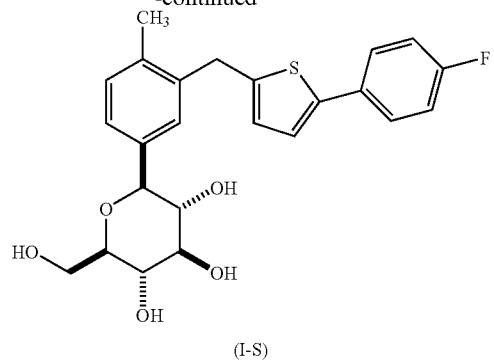

(I-S)

reacting the compound of formula (XIII-S), to yield the corresponding compound of formula (I-S).

6. A process as in claim 5, further comprising

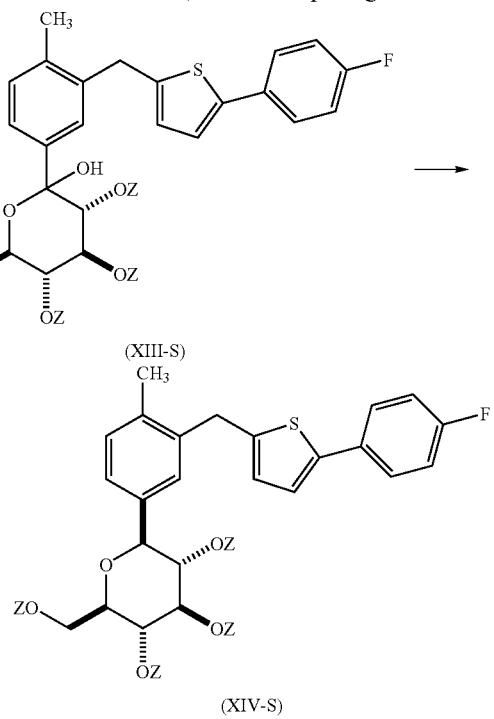

(XIII-S)

(XIV-S)

reacting the compound of formula (XIII-S) with a Lewis acid; in the presence of a silane reagent; in an organic solvent or mixture thereof; at a temperature in the range of from about 0° C. to about reflux; to yield the corresponding compound of formula (XIV-S);

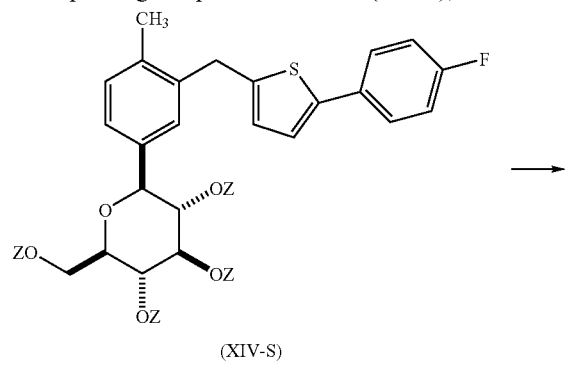

(XIV-S)

-continued

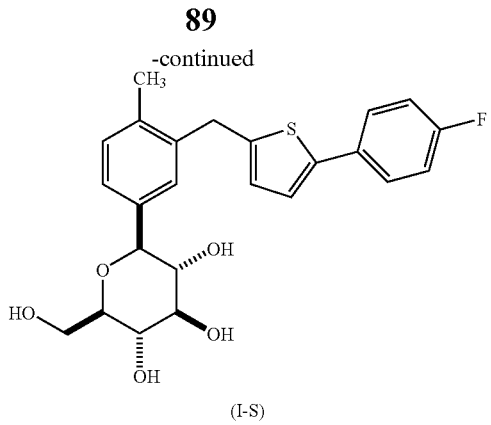
(I-S)

de-protecting the compound of formula (XIV-S); to yield the corresponding compound of formula (I-S).

7. A process as in claim 5, wherein the complex of di($C_{1-4}$ alkyl)magnesium with lithium chloride or the complex of $C_{1-4}$alkyl magnesium chloride with lithium chloride or the complex of $C_{1-4}$alkyl magnesium bromide with lithium chloride is present in an amount in the range of from about 1.0 to about 1.5 molar equivalents.

8. A process as in claim 5, wherein the compound of formula (X-S) is reacted with a complex of di($C_{1-4}$alkyl)magnesium with lithium chloride; and wherein the complex of di($C_{1-4}$alkyl)magnesium with lithium chloride is a complex of di(sec-butyl)magnesium with lithium chloride; to yield the corresponding compound of formula (XI-S) wherein $Q^1$ is MgCl.

9. A process as in claim 8, wherein the complex of di(sec-butyl)magnesium with lithium chloride is present in an amount in the range of from about 1.0 to about 1.5 molar equivalents.

10. A process as in claim 5, wherein Z is acetyl.

11. A process as in claim 5, wherein the compound of formula (XII-S) is present in an amount in the range of from about 1.0 to about 2.0 molar equivalents.

12. A process as in claim 5, wherein, when the compound of formula (XI-S) is reacted with the compound of formula (XII-S), the compound of formula (XI-S) is added to a mixture of the compound of formula (XII-S) in an organic solvent or mixture thereof.

13. A process as in claim 6, wherein the Lewis acid is selected from the group consisting of $BF_3 \cdot OEt_2$, $BF_3 \cdot THF$, aluminum chloride, zinc chloride and iron chloride; and wherein the silane is selected from the group consisting of triethylsilane, triisopropylsilane and tetramethyldisiloxane.

14. A process as in claim 13, wherein the Lewis acid is aluminum chloride and wherein the aluminum chloride is present in an amount in the range of from about 0.5 to about 2.5 molar equivalents.

15. A process as in claim 13, wherein the silane reagent is tetramethyldisiloxane; and wherein the tetramethyldisiloxane is present in an amount in the range of from about 1.0 to about 2.5 molar equivalents.

16. A process as in claim 13, wherein the Lewis acid is aluminum chloride; wherein the silane reagent is tetramethyldisiloxane; and wherein the molar ratio of aluminum chloride to tetramethyldisiloxane is about 1:1.25.

17. The process of claim 5, further comprising recrystallizing compound of formula (I-S)

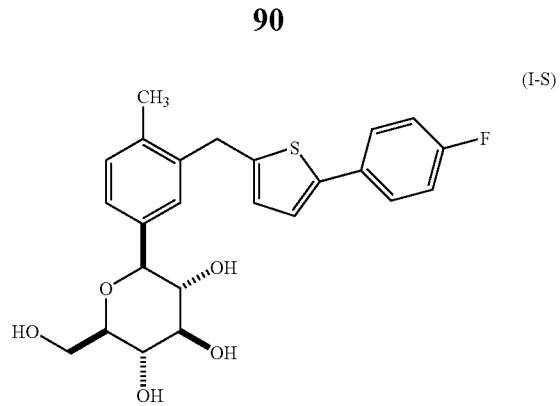
(I-S)

comprising
STEP A: dissolving a compound of formula (I-S) in an organic solvent;
STEP B: heating the mixture of STEP A to a temperature in the range of from about 25° C. to about 45° C.;
STEP C: adding water to the mixture prepared in STEP B; wherein the amount of water added is preferably in an amount in the range of from about 1.0 to about 2.0 molar equivalents;
STEP D: adding an anti-solvent to the mixture prepared in STEP C; to yield a precipitate of the compound of formula (I-S).

18. The process of claim 5, further comprising recrystallizing compound of formula (I-S)

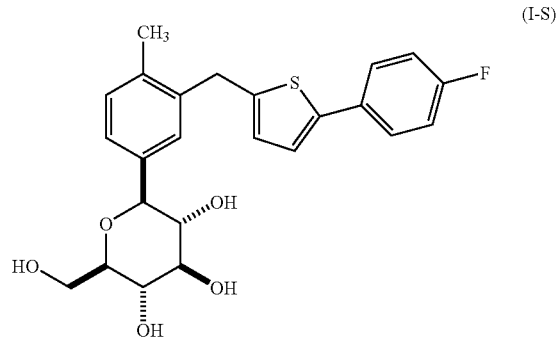
(I-S)

comprising
STEP A: dissolving a compound of formula (I-S) in an organic solvent;
STEP B: adding water to the mixture prepared in STEP A; wherein the amount of water added is preferably in an amount in the range of from about 1.0 to about 2.0 molar equivalents;
STEP C: heating the mixture of STEP B to a temperature in the range of from about 40° C. to about 65° C.;
STEP D: cooling the mixture prepared in STEP C; to yield a precipitate of the compound of formula (I-S).

19. A process for the preparation of a compound of formula (XVIII-S)

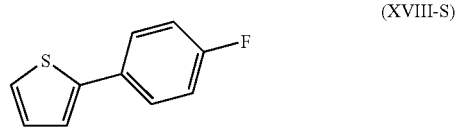 [SMILES: Fc1ccc(-c2cccs2)cc1]
(XVIII-S)

comprising

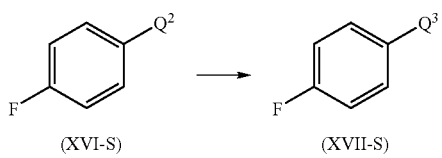

(XVI-S) (XVII-S)

reacting a compound of formula (XVI-S), wherein $Q^2$ is bromo, chloro or iodo, with a magnesium reagent; in an organic solvent; to yield the corresponding compound of formula (XVII-S), wherein $Q^3$ is the corresponding Grignard species;

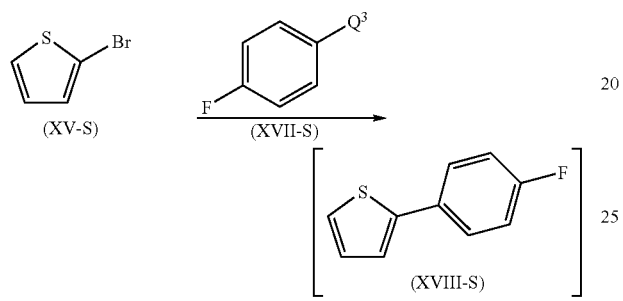

(XV-S) (XVII-S)

(XVIII-S)

reacting a compound of formula (XV-S) with the compound of formula (XVII-S); in the presence of a Ni or Pd catalyst; in an organic solvent to yield the corresponding compound of formula (XVIII-S).

20. A process as in claim 19, wherein $Q^2$ is bromo and wherein $Q^3$ is MgBr.

21. A process as in claim 19, wherein the magnesium reagent is magnesium.

22. A process as in claim 19, wherein the Ni or Pd catalyst is $NiCl_2(dppe)$.

23. A process as in claim 19, wherein the compound of formula (XV-S) is reacted with the compound of formula (XVII-S) in the presence of a ligand.

24. A process as in claim 23, wherein the Ni or Pd catalyst is $Pd(OAc)_2$ and the ligand is 1,3-bis(diphenylphosphino)propane.

25. A process as in claim 19, further comprising

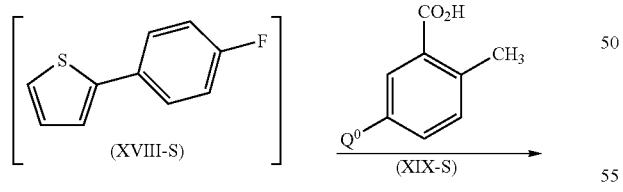

(XVIII-S) (XIX-S)

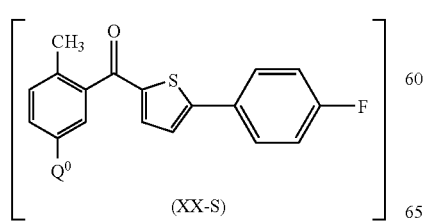

(XX-S)

reacting the compound of formula (XVIII-S) with a compound of formula (XIX-S), wherein $Q^0$ is bromo or iodo; to yield the corresponding compound of formula (XX-S);

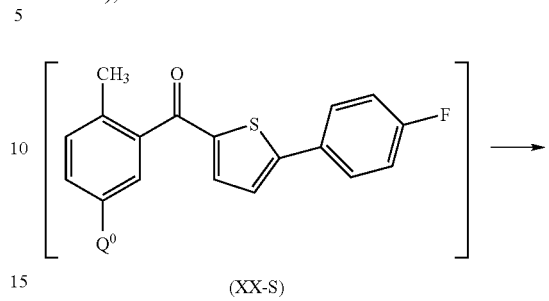

(XX-S)

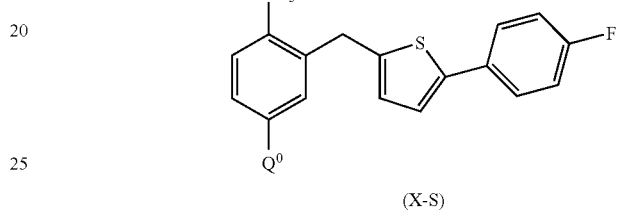

(X-S)

reducing the compound of formula (XX-S); to yield the corresponding compound of formula (X-S).

26. A process as in claim 25, wherein $Q^0$ is iodo.

27. A process for the preparation of a compound of formula (IA')

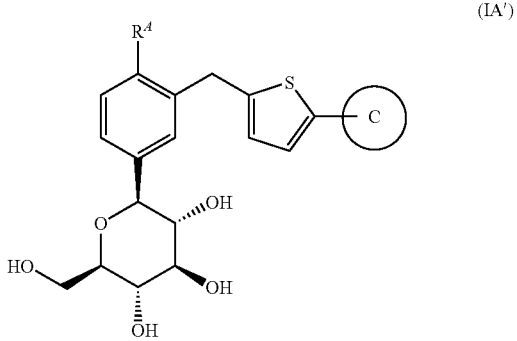

(IA')

wherein $R^A$ is halogen or lower alkyl;

Ring C is phenyl substituted with 1-3 substituents selected from the group consisting of halogen, cyano, lower alkyl, halo-lower alkyl, lower alkoxy, halo-lower alkoxy, methylenedioxy, ethyleneoxy, mono- or di-lower alkylamino, carbamoyl, and mono- or di-lower alkylcarbamoyl;

or heterocyclyl substituted by 1-3 substituents selected from the group consisting of halogen, cyano, lower alkyl, halo-lower alkyl, lower alkoxy, halo-lower alkoxy, mono- or di-lower alkylamino, carbamoyl, and mono- or di-lower alkylcarbamoyl;

or a pharmaceutically acceptable salt thereof; comprising steps of:

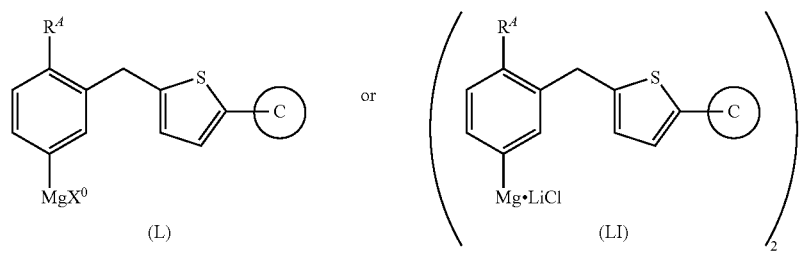

(L) or (LI)$_2$

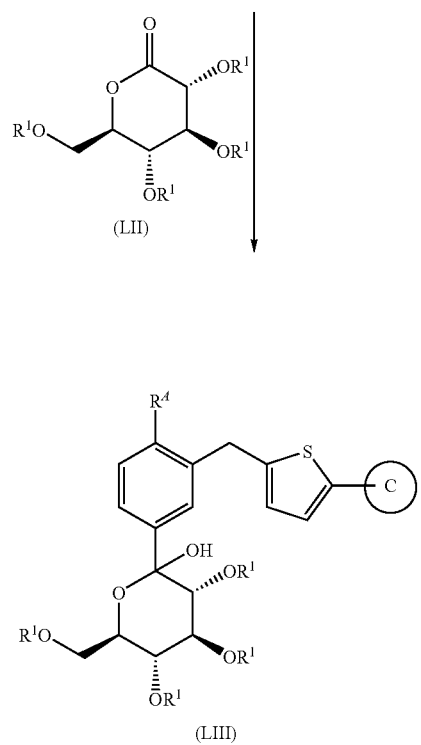

(LII)

(LIII)

reacting a compound of formula (L) wherein $X^0$ is selected from the group consisting of Cl, Br, I and Cl·LiCl or a compound of formula (LI) with a compound of formula (LII), wherein $R^1$ is tri-lower alkyl silyl; to yield the corresponding compound of formula (LIII);

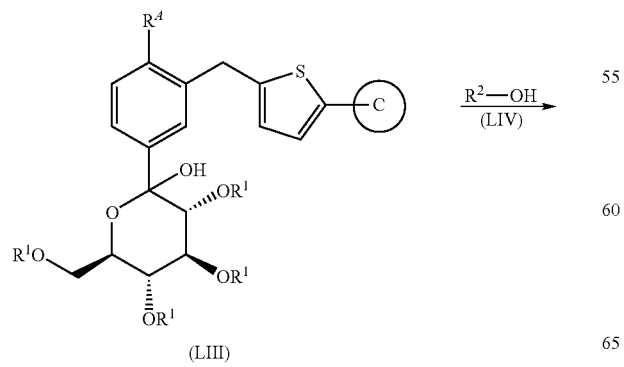

(LIII) $\xrightarrow{\underset{(LIV)}{R^2-OH}}$

-continued

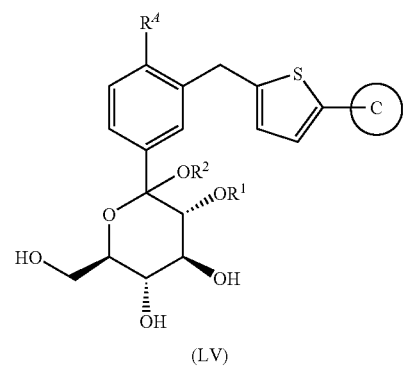

(LV)

reacting the compound of formula (LIII) with an alcohol of formula (LIV), wherein $R^2$ is lower alkyl; in the presence of an acid; to yield the corresponding compound of formula (LV);

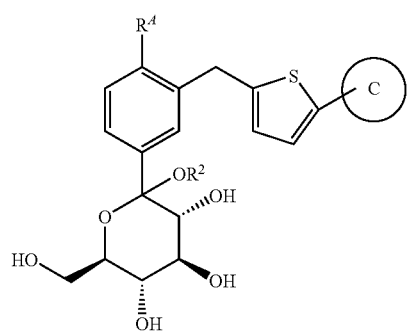

(LV)

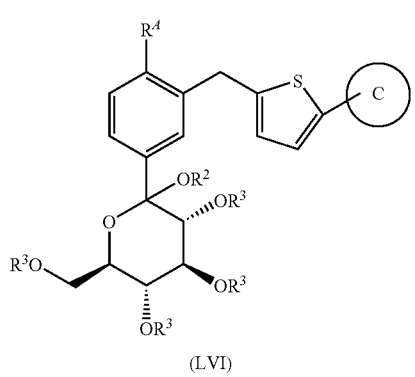

(LVI)

protecting the hydroxyl groups on the compound of formula (LV); to yield the corresponding compound of formula (LVI); wherein each R³ is an oxygen protecting group which is acetyl;

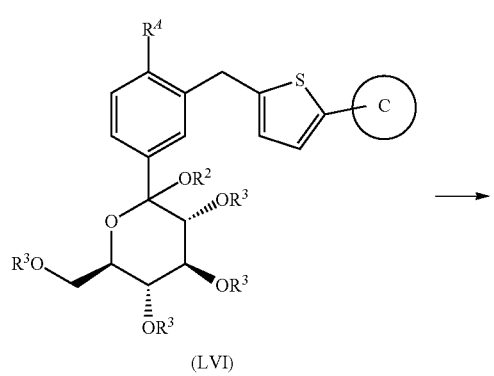

(LVI)

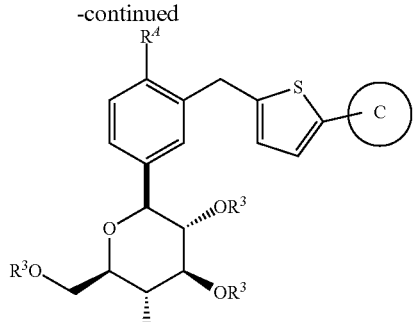

(LVII)

reducing the compound of formula (LVI); to yield the corresponding compound of formula (LVII);

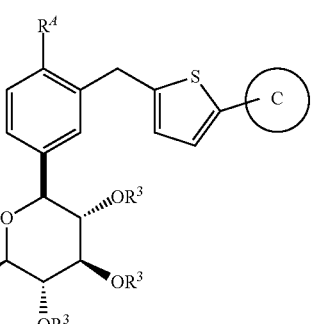

(LVII)

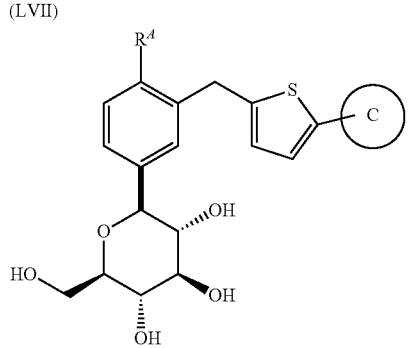

(IA')

removing the oxygen protecting groups of the compound of formula (LVII); to yield the corresponding compound of formula (IA').

28. A process as in claim 27, wherein $R^1$ is trimethylsilyl, $R^2$ is methyl or ethyl, and $R^3$ is acetyl.

29. A process as in claim 27, wherein the alcohol of formula (LIV) is methanol or ethanol and wherein the acid is an organic acid.

30. A process as in claim 27, wherein the compound of formula (LVI) is reduced by reacting with a silane reagent, in the presence of an acid.

31. A process as in claim 27, wherein the silane reagent is a tri-lower alkyl silane and wherein the acid is a Lewis acid.

* * * * *

UNITED STATES PATENT AND TRADEMARK OFFICE
CERTIFICATE OF CORRECTION

PATENT NO. : 9,056,850 B2
APPLICATION NO. : 12/578934
DATED : June 16, 2015
INVENTOR(S) : Filliers et al.

It is certified that error appears in the above-identified patent and that said Letters Patent is hereby corrected as shown below:

In the claims

Column 94
Line 50, Claim 27, delete

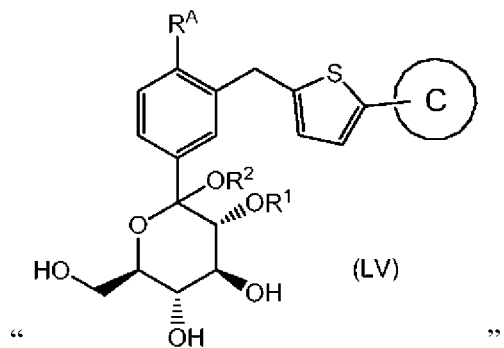

" and insert

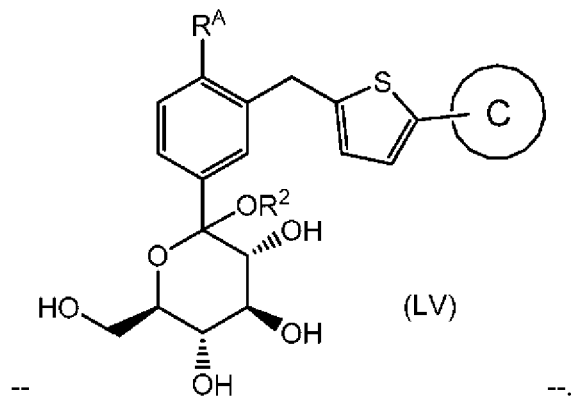

--.

Signed and Sealed this
Twenty-seventh Day of October, 2015

Michelle K. Lee
*Director of the United States Patent and Trademark Office*